(12) United States Patent
Chiba et al.

(10) Patent No.: US 7,312,245 B2
(45) Date of Patent: Dec. 25, 2007

(54) DIAMINE DERIVATIVES, PROCESS FOR PRODUCING THE DIAMINE DERIVATIVES, AND FUNGICIDES CONTAINING THE DIAMINE DERIVATIVES AS AN ACTIVE INGREDIENT

(75) Inventors: Yutaka Chiba, Mobara (JP); Hidenori Daido, Mobara (JP); Tomohisa Akase, Minato-ku (JP); Hirozumi Matsuno, Minato-ku (JP); Junro Kishi, Minato-ku (JP)

(73) Assignee: Mitsui Chemical, Inc., Tokyo (JP)

( * ) Notice: Subject to any disclaimer, the term of this patent is extended or adjusted under 35 U.S.C. 154(b) by 502 days.

(21) Appl. No.: 10/483,956

(22) PCT Filed: Jul. 18, 2002

(86) PCT No.: PCT/JP02/07319

§ 371 (c)(1),
(2), (4) Date: Jan. 16, 2004

(87) PCT Pub. No.: WO03/008372

PCT Pub. Date: Jan. 30, 2003

(65) Prior Publication Data

US 2005/0075512 A1    Apr. 7, 2005

(30) Foreign Application Priority Data

Jul. 18, 2001    (JP)    ............... 2001-218387

(51) Int. Cl.
A61K 31/235    (2006.01)
C07C 229/00    (2006.01)
C07C 271/00    (2006.01)

(52) U.S. Cl. ........................... 514/533; 560/19; 560/32
(58) Field of Classification Search ............... None
See application file for complete search history.

(56) References Cited

U.S. PATENT DOCUMENTS 6,358,960 B1    3/2002    Senokuchi et al.

| | | |
|---|---|---|
| 2003/0229092 A1 | 12/2003 | Ohimeyer et al. |
| 2004/0009982 A1 | 1/2004 | Tohnishi et al. |

FOREIGN PATENT DOCUMENTS

| | | |
|---|---|---|
| EP | 0 648 740 A1 | 4/1995 |
| WO | 99/41231 A1 | 8/1999 |
| WO | 01/05783 | 1/2001 |
| WO | 01/46124 | 6/2001 |
| WO | 01/46152 | 6/2001 |
| WO | WO 01/46152 A1 * | 6/2001 |
| WO | 02/40483 | 5/2002 |

OTHER PUBLICATIONS

Kyne et al, "Enantioselective amino acid recognition using acyclic thiourea receptors", *Journal of the Chemical Society, Perkin Trans 1*, No. 11, pp. 1258-1263 (2001), published by The Royal Society of Chemistry.

* cited by examiner

*Primary Examiner*—Paul A. Zucker
(74) *Attorney, Agent, or Firm*—Buchanan Ingersoll & Rooney PC

(57) ABSTRACT

A fungicide can be provided by using, as an active ingredient, a diamine derivative of the following general formula (1):

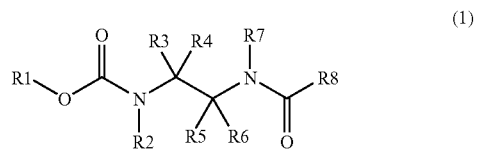

(1)

wherein
R1 to R7 represent a specific substituent such as an alkyl group with 1 to 6 carbon atoms, and R8 represents an aryl group, which may be substituted or a heteroaryl group, which may be substituted.

17 Claims, No Drawings

DIAMINE DERIVATIVES, PROCESS FOR PRODUCING THE DIAMINE DERIVATIVES, AND FUNGICIDES CONTAINING THE DIAMINE DERIVATIVES AS AN ACTIVE INGREDIENT

TECHNICAL FIELD

This invention relates to novel diamine derivatives, a process for producing the diamine derivatives, and a fungicide containing the diamine derivatives as an active ingredient.

BACKGROUND ART

Pest Control plays a significant role in cultivation of paddy rice, and, in particular, various fungicides have been developed and used against rice blast, which is considered to be an important disease injury. These fungicides, however, are not always satisfactory in terms of the desired fungicidal activity and control of the undesirable harmful effects on useful crops. In addition, in recent years, fungi having drug-resistant have emerged due to the frequent use of agricultural and horticultural fungicides, and the existing fungicides do not always exhibit satisfactory fungicidal activity. Furthermore, from the environmental viewpoint, there have been demands for novel fungicides which are safe and capable of controlling harmful fungi at lower concentrations.

DISCLOSURE OF INVENTION

Accordingly, an object of this invention is to provide diamine derivatives, which exhibit excellent effect to control rice blast, but does not injure useful crops.

In order to solve the above-described problems, the present inventors synthesized various novel diamine derivatives and various investigations relating to their fungicidal activities, etc., have been carried out. They have finally found the diamine derivatives, which exhibit excellent effect to control rice blast, but not injure useful crops. As a result the present inventors have completed this invention.

Specifically, this invention include the following embodiments and aspects:

[1] A diamine derivative, represented by the following general formula (1):

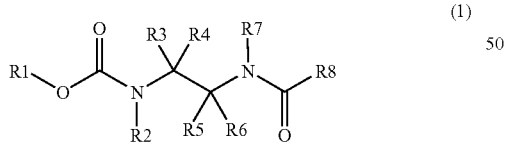

(1)

wherein
R1 represents an alkyl group with 1 to 6 carbon atoms provided that the case is excluded where R1 is a tert-butyl, a cycloalkyl group with 3 to 6 carbon atoms, an alkenyl group with 2 to 6 carbon atoms, a cycloalkenyl group with 3 to 6 carbon atoms, an alkynyl group with 2 to 6 carbon atoms, an arylalkyl group which may be substituted, a heteroarylalkyl group which may be substituted, an aryl group which may be substituted, or a heteroaryl group which may be substituted; R2 and R7 independently represent a hydrogen atom, an alkyl group with 1 to 6 carbon atoms, a cycloalkyl group with 3 to 6 carbon atoms, an alkenyl group with 2 to 6 carbon atoms, a cycloalkenyl group with 3 to 6 carbon atoms, an alkynyl group with 2 to 6 carbon atoms, an arylalkyl group which may be substituted, an aryl group which may be substituted, or an acyl group;

R3 and R4 independently represent a hydrogen atom, an alkyl group with 1 to 6 carbon atoms, a cycloalkyl group with 3 to 6 carbon atoms, an alkenyl group with 2 to 6 carbon atoms, a cycloalkenyl group with 3 to 6 carbon atoms, an alkynyl group with 2 to 6 carbon atoms, an arylalkyl group which may be substituted, a heteroarylalkyl group which may be substituted, an aryl group which may be substituted or a heteroaryl group which may be substituted, or a cycloalkyl group with 3 to 6 carbon atoms including an attached carbon atom;

R5 and R6 independently represent a hydrogen atom, an alkyl group with 1 to 6 carbon atoms, a cycloalkyl group with 3 to 6 carbon atoms, an alkenyl group with 2 to 6 carbon atoms, a cycloalkenyl group with 3 to 6 carbon atoms, an alkynyl group with 2 to 6 carbon atoms, an arylalkyl group which may be substituted, or an aryl group which may be substituted; provided that the case is excluded where R3, R4, R5 and R6 all represent a hydrogen atom or where any one of R3, R4, R5 and R6 represents a methyl group which may be substituted and the others represent a hydrogen atom, and R8 represents an aryl group which may be substituted or a heteroaryl group which may be substituted.

[2] The diamine derivative according to the above section [1], wherein
R1 represents an alkyl group with 1 to 6 carbon atoms provided that the case is excluded where R1 is a tert-butyl, a cycloalkyl group with 3 to 6 carbon atoms, an alkenyl group with 2 to 6 carbon atoms, an arylalkyl group which may be substituted, a heteroarylalkyl group which may be substituted, an aryl group which may be substituted, or a heteroaryl group which may be substituted;

R2 and R7 independently represent a hydrogen atom, an alkyl group with 1 to 6 carbon atoms, a cycloalkyl group with 3 to 6 carbon atoms, an arylalkyl group which may be substituted, an aryl group which may be substituted, or an acyl group;

R3 and R4 independently represent a hydrogen atom, an alkyl group with 1 to 6 carbon atoms, a cycloalkyl group with 3 to 6 carbon atoms, an alkenyl group with 2 to 6 carbon atoms, an arylalkyl group which may be substituted, a heteroarylalkyl group which may be substituted, an aryl group which may be substituted or a heteroaryl group which may be substituted, or a cycloalkyl group with 3 to 6 carbon atoms including an attached carbon atom; and R5 and R6 independently represent a hydrogen atom, an alkyl group with 1 to 6 carbon atoms, a cycloalkyl group with 3 to 6 carbon atoms, an arylalkyl group which may be substituted, or an aryl group which may be substituted; provided that the case is excluded where R3, R4, R5 and R6 all represent a hydrogen atom or where any one of R3, R4, R5 and R6 represents a methyl group which may be substituted and the others represent a hydrogen atom.

[3] The diamine derivative according to the above section [2], wherein
R2 and R7 independently represent a hydrogen atom, an alkyl group with 1 to 6 carbon atoms, or an acyl group;

R3 and R4 independently represent a hydrogen atom, an alkyl group with 1 to 6 carbon atoms, a cycloalkyl group with 3 to 6 carbon atoms, an arylalkyl group which maybe substituted, an aryl group which may be substituted, or a cycloalkyl group with 3 to 6 carbon atoms including an attached carbon atom; and R5 and R6 independently represent a hydrogen atom, an alkyl group with 1 to 6 carbon atoms, an arylalkyl group which may be substituted, or an aryl group which may be substituted; provided that the case is excluded where R3, R4, R5 and R6 all represent a hydrogen atom or where any one of R3, R4, R5 and R6 represents a methyl group which may be substituted and the others represent a hydrogen atom.

[4] The diamine derivative according to the above section [3], wherein R2 and R7 represent a hydrogen atom.

[5] A diamine derivative, represented by the following general formula (9):

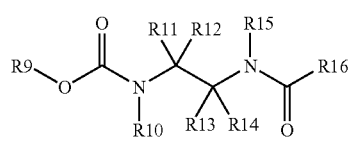
(9)

wherein R9 represents an alkyl group with 1 to 6 carbon atoms, a cycloalkyl group with 3 to 6 carbon atoms, an alkenyl group with 2 to 6 carbon atoms, a cycloalkenyl group with 3 to 6 carbon atoms, an alkynyl group with 2 to 6 carbon atoms, an arylalkyl group which may be substituted, a heteroarylalkyl group which may be substituted, a phenyl group, a phenyl group which is substituted at the fourth position, or a heteroaryl group which may be substituted;

R10 and R15 independently represent a hydrogen atom, an alkyl group with 1 to 6 carbon atoms, a cycloalkyl group with 3 to 6 carbon atoms, an alkenyl group with 2 to 6 carbon atoms, a cycloalkenyl group with 3 to 6 carbon atoms, an alkynyl group with 2 to 6 carbon atoms, an arylalkyl group which may be substituted, an aryl group which may be substituted, or an acyl group;

One of R11 and R12 represents a methyl group, and the other represents a hydrogen atom;

R13 and R14 represent a hydrogen atom, respectively; and

R16 represents a phenyl group, a phenyl group which is substituted at the fourth position, or a heteroaryl group which may be substituted.

[6] The diamine derivative according to the above section [5], wherein

R9 represents an alkyl group with 1 to 6 carbon atoms, a cycloalkyl group with 3 to 6 carbon atoms, an alkenyl group with 2 to 6 carbon atoms, an arylalkyl group which may be substituted, a heteroarylalkyl group which may be substituted, a phenyl group, a phenyl group which is substituted at the fourth position, or a heteroaryl group which may be substituted; and R10 and R15 represent a hydrogen atom, an alkyl group with 1 to 6 carbon atoms, a cycloalkyl group with 3 to 6 carbon atoms, an arylalkyl group which may be substituted, an aryl group which may be substituted, or an acyl group, independently.

[7] The diamine derivative according to the above section [6], wherein R10 and R15 independently represent a hydrogen atom, an alkyl group with 1 to 6 carbon atoms, or an acyl group.

[8] The diamine derivative according to the above section [7], wherein at R10 and R15 represent a hydrogen atom, respectively.

[9] A fungicide, wherein it contains the diamine derivative according to any one of the above sections [1] to [8] as an active ingredient.

[10] A process for producing the diamine derivative according to the above section [1], wherein a compound having the following general formula (2):

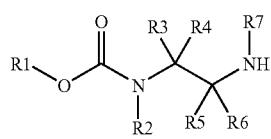
(2)

wherein

R1, R2, R3, R4, R5, R6 and R7 represent the same groups as those of the compounds according to the above section [1], is reacted with a compound having the following general formula (3):

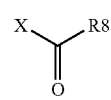
(3)

wherein

R8 represents the same group as that of the compound according to the above section [1], and X represents a leaving group.

[11] A process for producing the diamine derivative according to the above section [1], wherein a compound of the general formula (2) is condensed with a compound having the following general formula (4):

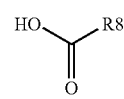
(4)

wherein

R8 represents the same group as that of the compounds according to the above section [1].

[12] A process for producing the diamine derivative according to the above section [1], wherein a compound having the following general formula (5):

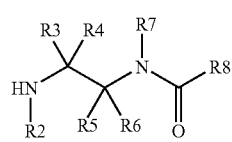
(5)

wherein

R2, R3, R4, R5, R6, R7 and R8 represent the same groups as those of the compound according to the above section [1], is reacted with a compound having the following general formula (6):

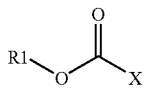
(6)

wherein

R1 represents the same group as that of the compound according to the above section [1], and X represents a leaving group.

[13] A process for producing the diamine derivative according to the above section [5], wherein a compound having the following general formula (10):

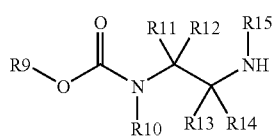
(10)

wherein

R9, R10, R11, R12, R13, R14 and R15 represent the same groups as those of the compounds according to the above section [5], is reacted with a compound having the following general formula (11):

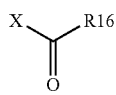
(11)

wherein

R16 represents the same group as that of the compound according to the above section [5], and X represents a leaving group.

[14] A process for producing the diamine derivative according to the above section [5], wherein a compound of the general formula (10) is condensed with a compound having the following general formula (12):

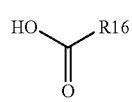
(12)

wherein

R16 represents the same group as that of the compounds according to the above section [5].

[15] A process for producing the diamine derivative according to the above section 5, wherein a compound having the following general formula (13):

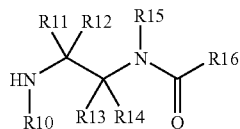
(13)

wherein

R10, R11, R12, R13, R14, R15 and R16 represent the same groups as those of the compound according to the above section [5], is reacted with a compound having the following general formula (14):

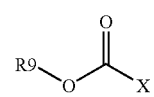
(14)

wherein

R9 represents the same group as that of the compound according to the above section [5], and X represents a leaving group.

BEST MODE FOR CARRYING OUT THE INVENTION

The invention will be described below more in detail.

In the diamine derivatives of the general formulas (1) and (9) and the process for producing the same, examples of the alkyl group with 1 to 6 carbon atoms include methyl, ethyl, propyl, butyl, pentyl, hexyl, allyl, methallyl and propargyl groups; examples of the cycloalkyl group with 3 to 6 carbon atoms include cyclopropyl, cyclobutyl, cyclopentyl and cyclohexyl groups; examples of the alkenyl group with 2 to 6 carbon atoms include vinyl, propenyl, butenyl, pentenyl and hexenyl groups; examples of the cycloalkenyl group with 3 to 6 carbon atoms include cyclopropenyl, cyclobutenyl, cyclopentenyl and cyclohexenyl groups; examples of the alkynyl group with 2 to 6 carbon atoms include ethynyl, propynyl, butynyl, pentynyl and hexynyl groups; examples of the aryl group include phenyl and naphthyl groups; examples of the heteroaryl group include pyridyl, pyrimidyl, thienyl, furanyl, pyrazolyl, imidazolyl, isothiazolyl, isoxazolyl, indolyl, quinolyl, benzofuranyl, benzothienyl, benzoxazolyl, benzoisoxazolyl, benzimidazolyl, benzothiazolyl and benzoisothiazolyl groups; examples of the acyl group include alkylcarbonyl groups such as acetyl group and arylcarbonyl groups such as benzoyl group.

Examples of the substituent(s) of the aryl group and the heteroaryl group include alkyl groups having 1 to 6 carbon atoms such as methyl, ethyl, propyl and butyl groups; cycloalkyl groups having 3 to 6 carbon atoms such as cyclopropyl, cyclobutyl, cyclopentyl and cyclohexyl groups; halogen-substituted alkyl groups having 1 to 4 carbon atoms such as trifluoromethyl, difluoromethyl, bromodifluoromethyl and trifluoroethyl groups; alkoxy groups having 1 to 4 carbon atoms such as methoxy, ethoxy, propoxy and butoxy groups; halogen-substituted alkoxy groups having 1 to 4 carbon atoms such as trifluoromethoxy, difluoromethoxy and trifluoroethoxy groups; alkylthio groups having 1 to 4 carbon atoms such as methylthio, ethylthio, propylthio and butylthio groups; halogen-substituted alkylthio groups having 1 to 4 carbon atoms such as trifluoromethylthio, difluoromethylthio and trifluoroethylthio groups; alkylsulfinyl groups having 1 to 4 carbon atoms such as methanesulfinyl, ethanesulfinyl, propanesulfinyl and butanesulfinyl groups; halogen-substituted alkylsulfinyl groups having 1 to 4 carbon atoms such as trifluoromethanesulfinyl, difluoromethanesulfinyl and trifluoroethanesulfinyl groups; alkyl sulfonyl groups having 1 to 4 carbon atoms such as methanesulfonyl, ethanesulfonyl; propanesulfonyl and butanesulfonyl groups; halogen-substituted alkylsulfonyl groups having 1 to 4 carbon atoms such as trifluoromethanesulfonyl, difluoromethanesulfonyl and trifluoroethanesulfonyl groups, alkylsulfonamide groups having 1 to 4 carbon atoms such as methanesulfonamide, ethanesulfonamide, propanesulfonamide and butanesulfonamide groups; halogen-substituted alkylsulfonamide groups having 1 to 4 carbon atoms such as trifluoromethanesulfonamide, difluoromethanesulfonamide and trifluoroethanesulfonamide groups; halogen atoms such as fluorine, chlorine, bromine and iodine atoms; and acyl groups such as acetyl and benzoyl groups.

The aryl group and the heteroaryl group may be substituted by two or more groups selected from them.

Examples of the methyl group, which may be substituted, include methyl, hydroxymethyl and halomethyl groups.

In the compounds of the general formulas (3), (6), (11) and (14), examples of the leaving groups include halogen atoms such as chlorine atom; alkoxy groups such as methoxy and ethoxy groups; aryloxy groups such as phenoxy group; and imidazole group.

The compounds of the invention represented by the general formulas (1) and (9) are novel. The compounds of formula (1) can be produced by the process shown by the following equation (1):

Equation (1)

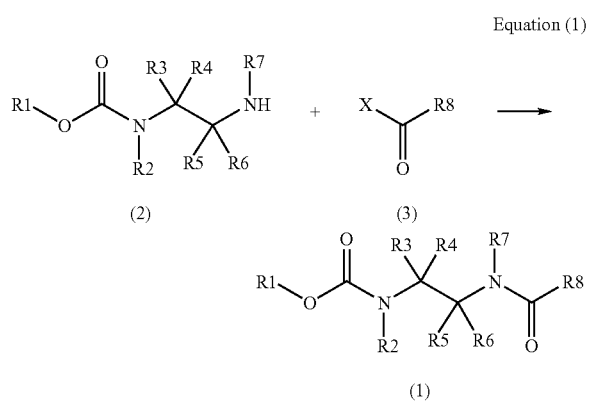

wherein

R1, R2, R3, R4, R5, R6 and R7 have the same definitions as those of the general formula (2), respectively; and R8 and X have the same definitions as those of the general formula (3), respectively.

In the equation (1), a diamine derivative of the general formula (1) can be produced by reacting a diamine derivative of the general formula (2) or its salt with a well known carbonyl compound of the general formula (3) in a reaction containing either no solvent or a solvent(s), and either in the absence of a base(s) or in the presence of base(s).

Examples of the base used in the reaction shown by the equation (1) include alkaline metal hydroxides such as sodium hydroxide and potassium hydroxide; alkaline earth metal hydroxides such as magnesium hydroxide and calcium hydroxide; alkaline metal hydrides such as sodium hydride and potassium hydride; alkaline metal alcoholates such as sodium methoxide and sodium ethoxide; alkaline metal oxides such as sodium oxide; carbonates such as potassium carbonate and sodium carbonate; phosphates such as tripotassium phosphate, tri-sodium phosphate, di-potassium hydrogen phosphate, di-sodium hydrogen phosphate; acetates such as sodium acetate and potassium acetate; organic bases such as pyridine, 4-(dimethylamino)pyridine, triethylamine and 1,8-diazabicyclo[5.4.0]undec-7-ene. At least one base can be used in the above reaction.

The quantity of the base(s) is not particularly limited, and when at least one of the above organic bases is used, it can also be used as a solvent.

Examples of the solvent which may be used in the reaction shown by the equation (1) include water; alcohols such as methanol, ethanol, propanol and butanol; halogenated hydrocarbons such as dichloromethane and chloroform; aromatic hydrocarbons such as benzene, toluene and xylene; aliphatic hydrocarbons such as hexane and heptane; polar aprotic solvents such as dimethylformamide (DMF), dimethylacetamide (DMA), dimethyl sulfoxide (DMSO), 1,3-dimethyl-2-imidazolidinone (DMI) and 1-methyl-2-pyrrolidone (NMP); ethers such as diethyl ether, diisopropyl ether, 1,2-dimethoxyethane (DME), tetrahydrofuran (THF) and dioxane; and nitrites such as acetonitrile and propionitrile.

The chemical equivalent of the carbonyl compound of the general formula (3) to the compound of the general formula (2) is preferably 1 to 2, and more preferably 1 to 1.2.

The reaction temperature and reaction time of the above reaction may be changed over a wide range. Generally, the reaction temperature may be preferably in the range from −20 to 200° C., more preferably from 0 to 100° C., and the reaction time may be preferably in the range from 0.01 to 50 hours, more preferably from 0.1 to 15 hours.

The amine derivatives and the salts thereof of the general formula (2) of the equation (1), other than commercially available ones, can be easily produced by the method such as Gabriel's synthesis; Delepine reaction; well known amine synthesis in which cyano group, amide, imine or oxime is reduced; or synthesis described in Tetrahedron Asymmetry, vol. 11, 1907 (2000).

The compounds of the general formula (3) of the equation (1) can be produced by conventional procedures in which a well known derivative of carboxylic acid of the general formula (4) is reacted with thionyl chloride, oxalyl chloride, phosgene or 1,1'-carbonylbis-1H-imidazole.

The compounds of the general formula (3) of the equation (1) can also be produced by conventional procedures in which a well known derivative of carboxylic acid of the general formula (4) is reacted with alcohol such as methyl alcohol or ethyl alcohol without a catalyst or in the presence of a catalyst.

The compounds of the invention, of the general formula (1), can also be produced by the process shown by the following equation (2).

Equation (2)

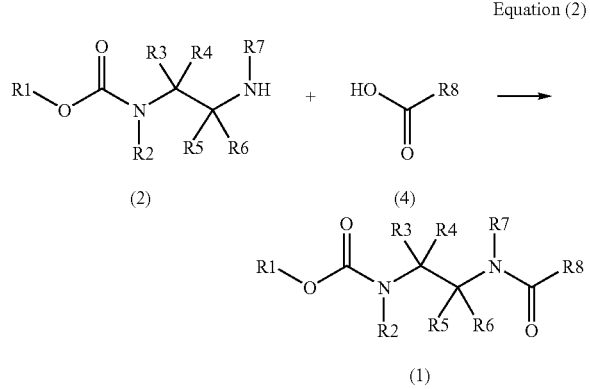

(1)

wherein

R1, R2, R3, R4, R5, R6 and R7 have the same definitions as in the general formula (2), respectively; and R8 has the same definition as that of the general formula (4).

In the equation (2), a diamine derivative of the general formula (1) can be produced by condensing a diamine derivative of the general formula (2) or its salt with a well known derivative of carboxylic acid of the general formula (4), in a reaction containing no solvent or a solvent(s).

Examples of the condensation agents for this case include: N,N'-dicyclohexylcarbodiimide,
1,1'-carbonylbis-1H-imidazole,
1-ethyl-3-(3-dimethylaminopropyl)carbodiimide hydrochloride, 2-chloro-1,3-dimethylimidazorium chloride.

As the quantity of the condensation agent to the compound of the general formula (4), the chemical equivalent of the former to the latter is preferably 1 to 2, more preferably 1 to 1.2.

As the organic solvent(s) for this case, the same solvent(s) as those for the process shown by the equation (1) may be used.

Regarding the quantity of the derivative of carboxylic acid of the general formula (4) to the compound of the general formula (2), the chemical equivalent of the former to the latter is preferably 1 to 2, more preferably 1 to 1.2.

The reaction temperature and reaction time of the above reaction may be changed over a wide range. Generally, the reaction temperature may be preferably in the range from −20 to 200° C., more preferably from 0 to 100° C., and the reaction time may be preferably in the range from 0.01 to 50 hours, more preferably from 0.1 to 15 hours.

The compounds of the invention of the general formula (1), can also be produced by the process shown by the following equation (3):

Equation (3)

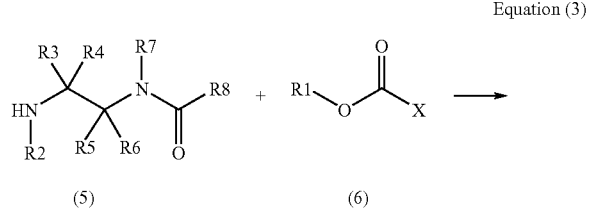

-continued

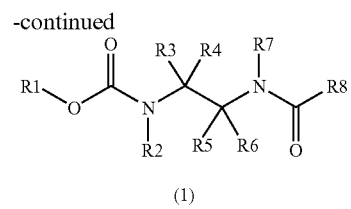

(1)

wherein

R2, R3, R4, R5, R6, R7 and R8 have the same definitions as those of the general formula (5), respectively; and R1 and X have the same definitions as those of the general formula (6), respectively.

In the equation (3), a diamine derivative of the general formula (1) can be produced by reacting a diamine derivative of the general formula (5) or its salt with a well known compound of the general formula (6) in a reaction containing no solvent or a solvent(s), either in the absence of a base(s) or in the presence of a base(s).

In this reaction, the same base(s) as those used in the equation (1) can be used.

The quantity of the bases used is not particularly limited, and when the above organic base(s) is used, they can also be used as a solvent.

As the solvent(s) for this case, the same solvent(s) as those used in the process shown by the equation (1) can be used.

Regarding the quantity of the compounds of the general formula (6) to the diamine derivatives of the general formula (5), the chemical equivalent of the former to the latter is preferably 1 to 2, more preferably 1 to 1.2.

The reaction temperature and reaction time of the above reaction may be changed over a wide range. Generally, the reaction temperature may be preferably in the range from −20 to 200° C., more preferably from 0 to 100° C., and the reaction time may be preferably in the range from 0.01 to 50 hours, more preferably from 0.1 to 15 hours.

The compounds of formula (9) can be produced in the same manners by substituting the compounds (2) to (6) in the reaction equations (1) to (3) with the compounds (10) to (14) mentioned above.

There exist asymmetric carbon atoms in the diamine derivatives of the general formulas (1) and (9), depending on the type of substituent(s), and the derivatives can exist as an optical isomer, diastereoisomer, racemic modification or mixture thereof at an arbitrary rate. The invention embraces all isomers of these types and the mixture thereof.

The agricultural and horticultural fungicides containing the diamine derivatives of the invention represented by the general formulas (1) and (9) as an active ingredient exhibit an excellent effect to control rice blast caused by *Pyricularia oryzae*.

The diamine derivatives of the invention of the general formulas (1) and (9) can be used by combining them with at least one of other fungicides, agricultural chemicals such as insecticides, herbicides and plant growth regulators, soil conditioners, and fertilizer responsive substances. They can be applied in the form of a mixture preparation.

Although the diamine derivatives of the present invention may be used as they are, they are preferably used as a formulation in the form of a composition, which can be obtained by mixing them with a carrier including a solid or liquid diluent. The term "carrier" herein used means a synthetic or natural, inorganic or organic materials which is mixed to help the active ingredient reach the target site and make easier the storage, transportation and handling of the active ingredient compounds.

Examples of the solid carriers suitably used in the invention include clays such as montmorillonite, kaolinite and bentonite; inorganic substances such as diatomaceous earth, clay, talc, vermiculite, plaster, calcium carbonate, silica gel and ammonium sulfide; vegetable organic materials such as soybean flour, sawdust and wheat flour; and urea.

Examples of the liquid carriers suitably used in the invention include aromatic hydrocarbons such as toluene, xylene and cumene; paraffin hydrocarbons such as kerosine and mineral oil; halogenated hydrocarbons such as carbon tetrachloride, chloroform and dichloroethane; ketones such as acetone and methyl ethyl ketone; ethers such as dioxane, tetrahydrofuran and diethylene glycol dimethyl ether; alcohols such as methanol, ethanol, propanol and ethylene glycol; dimethylformamide; dimethyl sulfoxide; and water.

In order to enhance the effectiveness of the compounds of the invention, at least one of the following adjuvants can be used solely or in their combination, according to the object, while taking into account the formulation of the compounds, the site of application, etc.

When aiming at emulsification, dispersion, spreading, moistening, binding and stabilization of the compounds, an adjuvant(s) may be used for the formulation. Examples of the adjuvants include anionic surfactants such as ligninsulfonate, alkylbenzenesulfonate, alkylsulfate ester, polyoxyalkylene alkylsulfate ester and polyoxyalkylene alkylphosphate ester; nonionic surfactants such as polyoxyalkylene alkyl ether, polyoxyalkylene alkylaryl ether, polyoxyalkylene alkylamine, polyoxyalkylene alkylamide, polyoxyalkylene alkyl thioether, polyoxyalkylene fatty ester, glycerol fatty ester, sorbitan fatty ester, polyoxyalkylene sorbitan fatty ester and polyoxypropylene polyoxyethylene block copolymer; lubricants such as calcium stearate and wax; stabilizers such as isopropylhydrodiene phosphate; methyl cellulose; carboxymethyl cellulose; casein; and gum arabic. The adjuvants used are not limited to the above described ones.

The quantity of the compounds of the invention as an active ingredient is generally 0.5 to 20% by weight for dust formulation, 5 to 50% by weight for emulsifiable concentrate, 10 to 90% by weight for wettable powder, 0.1 to 20% by weight for granular, and 10 to 90% by weight for flowable. The quantity of carrier in each formulation is generally 60 to 99% by weight for dust, 40 to 95% by weight for emulsifiable concentrate, 10 to 90% by weight for wettable powder, 80 to 99% by weight for granular, and 10 to 90% by weight for flowable, respectively. The quantity of adjuvant is generally 0.1 to 20% by weight for dust, 1 to 20% by weight for emulsifiable concentrate, 0.1 to 20% by weight for wettable powder, 0.1 to 20% by weight for granular, and 0.1 to 20% by weight for flowable.

EXAMPLES

In the following, the invention will be described in further detail taking several examples and test examples.

Example 1

Preparation of N-(methoxycarbonyl)-N'-benzoyl-1-phenyl-1,2-ethylenediamine (Compound No. 66)

0.22 g of benzoyl chloride was added to 10 ml of a solution of 0.25 g of N-(methoxycarbonyl)-1-phenylethylenediamine and 0.2 g of triethylamine in dichloromethane under ice cooling, and the mixture was stirred for 30 minutes at 5° C. and at room temperature for 3 hours. The reaction mixture was rinsed with water, the organic layer was dried over magnesium sulfate anhydrous, and the residual oily material obtained under a reduced pressure was purified by column chromatography on silica gel (2:1 hexane/ethyl acetate) to obtain 0.28 g of the title compound as colorless crystals.

Example 2

Preparation of N-(4-chlorobenzoyl)-N'-(i-propoxycarbonyl)-3-phenyl-1,2-propanediamine (Compound No. 290)

0.21 g of 1,1'-carbonylbis-1H-imidazole was added to a solution of 0.19 g of 4-chlorobenzoic acid in tetrahydrofuran and stirred for 1 hour at room temperature. Then 5 ml of a solution of 0.25 g of 2-(i-propoxycarbonylamino)-3-phenyl-propylamine in tetrahydrofuran was added to the above solution and stirred at room temperature for 4 hours. The reaction mixture was rinsed with water, the organic layer was dried over magnesium sulfate anhydrous, and the residual oily material obtained under a reduced pressure was purified by column chromatography on silica gel (2:1 hexane/ethyl acetate) to obtain 0.26 g of the title compound as colorless crystals.

Example 3

Preparation of N-(benzyloxycarbonyl)-N'-benzoyl-1-phenyl-1,2-ethylenediamine (Compound No. 636)

0.12 g of triethylamine was added to 10 ml of a solution of 0.25 g of N-benzoyl-2-phenyl-1,2-ethylenediamine hydrochloride and 0.17 g of benzyl chloroformate in dichloromethane under ice cooling, and the mixture was stirred at 5° C. for 30 minutes and at room temperature for 3 hours. The reaction mixture was rinsed with water, the organic layer was dried over magnesium sulfate anhydrous, and the residual oily material obtained under a reduced pressure was purified by column chromatography on silica gel (2:1 hexane/ethyl acetate) to obtain 0.28 g of the title compound as colorless crystals.

Example 4

Preparation of N-(t-butoxycarbonyl)-N'-(4-methylbenzoyl)-1-phenyl-1,2-ethylenediamine (Compound No. 504)

0.24 g of triethylamine was added to a solution of 0.22 g of di-t-butyl dicarbonate and 0.25 g of N-(4-methylbenzoyl)-2-phenyl-1,2-ethylenediamine hydrochloride in dichloromethane under ice cooling, and the mixture was stirred at 5° C. for 1 hour and at room temperature for 3 hours. The reaction mixture was rinsed with water, the organic layer was dried over magnesium sulfate anhydrous, and the residual oily material obtained under a reduced pressure was purified by column chromatography on silica gel (2:1 hexane/ethyl acetate) to obtain 0.24 g of the title compound as colorless crystals.

The compounds of the general formulas (1) and (9) which can be produced in the same manner as in Examples 1 to 4 are shown in Table 1 below. And the physical properties of some of the compounds are shown in Table 2. R17 to R24 in Table 1 are the substitutions shown in the following formula (15):

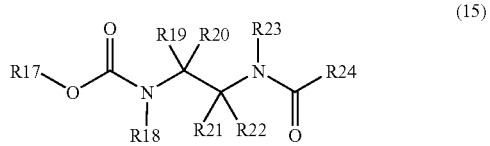

In Table 1, Me represents a methyl group, Et represents an ethyl group, n-Pr represents a normal propyl group, i-Pr represents an isopropyl group, i-Bu represents an isobutyl group, s-Bu represents a secondary butyl group, t-Bu represents a tertiary butyl group, Ph represents a phenyl group, Bn represents a benzyl group, 1-Naph represents a 1-naphtyl group, 2-Naph represents a 2-naphtyl group, c-Pr represents a cyclopropyl group, c-Hex represents a cyclohexyl group, Ac represents an acetyl group, Bz represents a benzoyl group, vinyl represents an ethenyl group, allyl represents a 2-propenyl group, propargyl represents a 2-propynyl group, neopentyl represents a 2,2-dimethylpropyl group, methallyl represents a 2-methyl-2-propenyl group, and 2-thienyl represents a thiophene-2-yl group.

TABLE 1

| Comp. No. | R17 | R18 | R19 | R20 | R21 | R22 | R23 | R24 |
|---|---|---|---|---|---|---|---|---|
| 1 | Me | H | Me | H | H | H | H | Ph |
| 2 | Me | H | Me | H | H | H | H | 2-ClC6H4 |
| 3 | Me | H | Me | Me | H | H | H | 3-ClC6H4 |
| 4 | Me | H | Me | H | H | H | H | 4-ClC6H4 |
| 5 | Me | H | Me | H | H | H | H | 4-MeC6H4 |
| 6 | Me | H | Me | H | H | H | H | 4-t-BuC6H4 |
| 7 | Me | H | Me | H | H | H | H | 1-Naph |
| 8 | Me | H | Me | H | H | H | H | thiophene-2-yl |
| 9 | Me | H | Me | H | H | H | H | pyridine-3-yl |
| 10 | Me | H | Me | Me | H | H | H | 4-ClC6H4 |
| 11 | Me | H | Et | H | H | H | H | Ph |
| 12 | Me | H | Et | H | H | H | H | 2-ClC6H4 |
| 13 | Me | H | Et | H | H | H | H | 3-ClC6H4 |
| 14 | Me | H | Et | H | H | H | H | 4-ClC6H4 |
| 15 | Me | H | Et | H | H | H | H | 4-MeC6H4 |
| 16 | Me | H | Et | H | H | H | H | 4-t-BuC6H4 |
| 17 | Me | H | Et | H | H | H | H | 1-Naph |
| 18 | Me | H | Et | H | H | H | H | thiophene-2-yl |
| 19 | Me | H | Et | H | H | H | H | 2-methyl pyridine-5-yl |
| 20 | Me | H | Et | Me | H | H | H | 4-ClC6H4 |
| 21 | Me | H | n-Pr | H | H | H | H | Ph |
| 22 | Me | H | n-Pr | H | H | H | H | 2-ClC6H4 |
| 23 | Me | H | n-Pr | H | H | H | H | 4-ClC6H4 |
| 24 | Me | H | n-Pr | H | H | H | H | 4-MeC6H4 |
| 25 | Me | H | n-Pr | H | H | H | H | 4-EtC6H4 |
| 26 | Me | H | i-Pr | H | H | H | H | Ph |
| 27 | Me | H | i-Pr | H | H | H | H | 4-ClC6H4 |
| 28 | Me | H | i-Pr | H | H | H | H | 3,4-Cl2C6H3 |
| 29 | Me | H | i-Pr | H | H | H | H | 2-MeC6H4 |
| 30 | Me | H | i-Pr | H | H | H | H | 4-MeC6H4 |
| 31 | Me | H | i-Pr | H | H | H | H | 4-EtC6H4 |
| 32 | Me | H | i-Pr | H | H | H | H | 2-Naph |
| 33 | Me | H | i-Pr | H | H | H | H | 5-methyl thiophene-2-yl |
| 34 | Me | H | i-Pr | H | H | H | H | pyridine-3-yl |
| 35 | Me | H | i-Pr | Me | H | H | H | 4-MeC6H4 |
| 36 | Me | H | s-Bu | H | H | H | H | Ph |
| 37 | Me | H | s-Bu | H | H | H | H | 4-ClC6H4 |
| 38 | Me | H | s-Bu | H | H | H | H | 3,4-Cl2C6H3 |
| 39 | Me | H | s-Bu | H | H | H | H | 2-MeC6H4 |
| 40 | Me | H | s-Bu | H | H | H | H | 4-MeC6H4 |
| 41 | Me | H | s-Bu | H | H | H | H | 4-t-BuC6H4 |
| 42 | Me | H | s-Bu | H | H | H | H | 1-Naph |
| 43 | Me | H | s-Bu | H | H | H | H | thiophene-2-yl |
| 44 | Me | H | s-Bu | H | H | H | H | isothiazole-5-yl |
| 45 | Me | H | s-Bu | Me | H | H | H | 4-CF3C6H4 |
| 46 | Me | H | i-Bu | H | H | H | H | Ph |
| 47 | Me | H | i-Bu | H | H | H | H | 4-ClC6H4 |
| 48 | Me | H | i-Bu | H | H | H | H | 3,4-Cl2C6H3 |
| 49 | Me | H | i-Bu | H | H | H | H | 2-MeC6H4 |
| 50 | Me | H | i-Bu | H | H | H | H | 4-MeC6H4 |
| 51 | Me | H | i-Bu | H | H | H | H | 4-t-BuC6H4 |
| 52 | Me | H | i-Bu | H | H | H | H | 2-Naph |
| 53 | Me | H | i-Bu | H | H | H | H | thiophene-2-yl |
| 54 | Me | H | i-Bu | H | H | H | H | 3-methyl isothiazole-5-yl |
| 55 | Me | H | i-Bu | Me | H | H | H | 4-ClC6H4 |

TABLE 1-continued

| Comp. No. | R17 | R18 | R19 | R20 | R21 | R22 | R23 | R24 |
|---|---|---|---|---|---|---|---|---|
| 56 | Me | H | t-Bu | H | H | H | H | Ph |
| 57 | Me | H | t-Bu | H | H | H | H | 4-ClC6H4 |
| 58 | Me | H | t-Bu | H | H | H | H | 3,4-Cl2C6H3 |
| 59 | Me | H | t-Bu | H | H | H | H | 2-MeC6H4 |
| 60 | Me | H | t-Bu | H | H | H | H | 4-MeC6H4 |
| 61 | Me | H | t-Bu | H | H | H | H | 4-t-BuC6H4 |
| 62 | Me | H | t-Bu | H | H | H | H | 1-Naph |
| 63 | Me | H | t-Bu | H | H | H | H | thiophene-2-yl |
| 64 | Me | H | t-Bu | H | H | H | H | isothiazole-5-yl |
| 65 | Me | H | t-Bu | Me | H | H | H | 4-MeC6H4 |
| 66 | Me | H | Ph | H | H | H | H | Ph |
| 67 | Me | H | Ph | H | H | H | H | 2-ClC6H4 |
| 68 | Me | H | Ph | H | H | H | H | 4-ClC6H4 |
| 69 | Me | H | Ph | H | H | H | H | 4-MeC6H4 |
| 70 | Me | H | Ph | H | H | H | H | 4-EtC6H4 |
| 71 | Me | H | 4-ClC6H4 | H | H | H | H | Ph |
| 72 | Me | H | 4-ClC6H4 | H | H | H | H | 4-CF3C6H4 |
| 73 | Me | H | 4-ClC6H4 | H | H | H | H | 2-MeC6H4 |
| 74 | Me | H | 4-ClC6H4 | H | H | H | H | 4-MeC6H4 |
| 75 | Me | H | 4-ClC6H4 | H | H | H | H | 4-t-BuC6H4 |
| 76 | Me | H | Bn | H | H | H | H | Ph |
| 77 | Me | H | Bn | H | H | H | H | 4-CF3C6H4 |
| 78 | Me | H | Bn | H | H | H | H | 2-MeC6H4 |
| 79 | Me | H | Bn | H | H | H | H | 4-MeC6H4 |
| 80 | Me | H | Bn | H | H | H | H | 4-EtC6H4 |
| 81 | Me | H | -(CH2)2- | | H | H | H | 4-ClC6H4 |
| 82 | Me | H | -(CH2)4- | | H | H | H | 4-ClC6H4 |
| 83 | Et | H | Me | H | H | H | H | Ph |
| 84 | Et | H | Me | H | H | H | H | 2-ClC6H4 |
| 85 | Et | H | Me | H | Me | H | H | 3-ClC6H4 |
| 86 | Et | H | Me | H | H | H | H | 4-ClC6H4 |
| 87 | Et | H | Me | H | H | H | H | 4-MeC6H4 |
| 88 | Et | H | Me | H | H | H | H | 4-t-BuC6H4 |
| 89 | Et | H | Me | H | H | H | H | 1-Naph |
| 90 | Et | H | Me | H | H | H | H | 5-chloro thiophene-2-yl |
| 91 | Et | H | Me | H | H | H | H | pyridine-3-yl |
| 92 | Et | H | Me | Me | H | H | H | 4-ClC6H4 |
| 93 | Et | H | Et | H | H | H | H | Ph |
| 94 | Et | H | Et | H | H | H | H | 2-ClC6H4 |
| 95 | Et | H | Et | H | H | H | H | 3-ClC6H4 |
| 96 | Et | H | Et | H | H | H | H | 4-ClC6H4 |
| 97 | Et | H | Et | H | H | H | H | 4-MeC6H4 |
| 98 | Et | H | Et | H | H | H | H | 4-t-BuC6H4 |
| 99 | Et | H | Et | H | H | H | H | 1-Naph |
| 100 | Et | H | Et | H | H | H | H | thiophene-2-yl |
| 101 | Et | H | Et | H | H | H | H | pyridine-3-yl |
| 102 | Et | H | Et | Me | H | H | H | 4-ClC6H4 |
| 103 | Et | H | i-Pr | H | H | H | H | Ph |
| 104 | Et | H | i-Pr | H | H | H | H | 4-ClC6H4 |
| 105 | Et | H | i-Pr | H | H | H | H | 3,4-Cl2C6H3 |
| 106 | Et | H | i-Pr | H | H | H | H | 2-MeC6H4 |
| 107 | Et | H | i-Pr | H | H | H | H | 4-MeC6H4 |
| 108 | Et | H | i-Pr | H | H | H | H | 4-EtC6H4 |
| 109 | Et | H | i-Pr | H | H | H | H | 2-Naph |
| 110 | Et | H | i-Pr | H | H | H | H | thiophene-2-yl |
| 111 | Et | H | i-Pr | H | H | H | H | 4-chloro pyridine-3-yl |
| 112 | Et | H | i-Pr | Me | H | H | H | 4-MeC6H4 |
| 113 | Et | H | s-Bu | H | H | H | H | Ph |
| 114 | Et | H | s-Bu | H | H | H | H | 4-ClC6H4 |
| 115 | Et | H | s-Bu | H | H | H | H | 3,4-Cl2C6H3 |
| 116 | Et | H | s-Bu | H | H | H | H | 2-MeC6H4 |
| 117 | Et | H | s-Bu | H | H | H | H | 4-MeC6H4 |
| 118 | Et | H | s-Bu | H | H | H | H | 4-t-BuC6H4 |
| 119 | Et | H | s-Bu | H | H | H | H | 1-Naph |
| 120 | Et | H | s-Bu | H | H | H | H | thiophene-2-yl |
| 121 | Et | H | s-Bu | H | H | H | H | isothiazole-5-yl |
| 122 | Et | H | s-Bu | Me | H | H | H | 4-MeC6H4 |
| 123 | Et | H | i-Bu | H | H | H | H | Ph |
| 124 | Et | H | i-Bu | H | H | H | H | 4-ClC6H4 |
| 125 | Et | H | i-Bu | H | H | H | H | 3,4-Cl2C6H3 |
| 126 | Et | H | i-Bu | H | H | H | H | 2-MeC6H4 |
| 127 | Et | H | i-Bu | H | H | H | H | 4-MeC6H4 |
| 128 | Et | H | i-Bu | H | H | H | H | 4-t-BuC6H4 |
| 129 | Et | H | i-Bu | H | H | H | H | 1-Naph |
| 130 | Et | H | i-Bu | H | H | H | H | thiophene-2-yl |

TABLE 1-continued

| Comp. No. | R17 | R18 | R19 | R20 | R21 | R22 | R23 | R24 |
|---|---|---|---|---|---|---|---|---|
| 131 | Et | H | i-Bu | H | H | H | H | isothiazole-5-yl |
| 132 | Et | H | i-Bu | Me | H | H | H | 4-MeC6H4 |
| 133 | Et | H | t-Bu | H | H | H | H | Ph |
| 134 | Et | H | t-Bu | H | H | H | H | 4-ClC6H4 |
| 135 | Et | H | t-Bu | H | H | H | H | 3,4-Cl2C6H3 |
| 136 | Et | H | t-Bu | H | H | H | H | 2-MeC6H4 |
| 137 | Et | H | t-Bu | H | H | H | H | 4-MeC6H4 |
| 138 | Et | H | t-Bu | H | H | H | H | 4-t-BuC6H4 |
| 139 | Et | H | t-Bu | H | H | H | H | 1-Naph |
| 140 | Et | H | t-Bu | H | H | H | H | thiophene-2-yl |
| 141 | Et | H | t-Bu | H | H | H | H | isothiazole-5-yl |
| 142 | Et | H | t-Bu | Me | H | H | H | 4-MeC6H4 |
| 143 | Et | H | Ph | H | H | H | H | Ph |
| 144 | Et | H | Ph | H | H | H | H | 2-ClC6H4 |
| 145 | Et | H | Ph | H | H | H | H | 4-ClC6H4 |
| 146 | Et | H | Ph | H | H | H | H | 4-MeC6H4 |
| 147 | Et | H | Ph | H | H | H | H | 4-EtC6H4 |
| 148 | n-Pr | H | Me | H | H | H | H | Ph |
| 149 | n-Pr | H | Me | H | H | H | H | 2-ClC6H4 |
| 150 | n-Pr | H | Me | Me | H | H | H | 3-ClC6H4 |
| 151 | n-Pr | H | Me | H | H | H | H | 4-ClC6H4 |
| 152 | n-Pr | H | Me | H | H | H | H | 4-MeC6H4 |
| 153 | n-Pr | H | Me | H | H | H | H | 4-t-BuC6H4 |
| 154 | n-Pr | H | Me | H | H | H | H | 1-Naph |
| 155 | n-Pr | H | Me | H | H | H | H | 5-ethyl thiophene-2-yl |
| 156 | n-Pr | H | Me | H | H | H | H | pyridine-3-yl |
| 157 | n-Pr | H | Me | Me | H | H | H | 4-ClC6H4 |
| 158 | n-Pr | H | Et | H | Et | H | H | Ph |
| 159 | n-Pr | H | Et | H | Et | H | H | 2-ClC6H4 |
| 160 | n-Pr | H | Et | H | Et | H | H | 3-ClC6H4 |
| 161 | n-Pr | H | Et | H | Et | H | H | 4-ClC6H4 |
| 162 | n-Pr | H | Et | H | Et | H | H | 4-MeC6H4 |
| 163 | n-Pr | H | Et | H | Et | H | H | 4-t-BuC6H4 |
| 164 | n-Pr | H | Et | H | Et | H | H | 1-Naph |
| 165 | n-Pr | H | Et | H | Et | H | H | thiophene-2-yl |
| 166 | n-Pr | H | Et | H | Et | H | H | pyridine-3-yl |
| 167 | n-Pr | H | Et | Me | Et | H | H | 4-ClC6H4 |
| 168 | n-Pr | H | i-Pr | H | H | H | H | Ph |
| 168 | n-Pr | H | i-Pr | H | H | H | H | 4-ClC6H4 |
| 169 | n-Pr | H | i-Pr | H | H | H | H | 3,4-Cl2C6H3 |
| 170 | n-Pr | H | i-Pr | H | H | H | H | 2-MeC6H4 |
| 171 | n-Pr | H | i-Pr | H | H | H | H | 4-MeC6H4 |
| 172 | n-Pr | H | i-Pr | H | H | H | H | 4-EtC6H4 |
| 173 | n-Pr | H | i-Pr | H | H | H | H | 2-Naph |
| 174 | n-Pr | H | i-Pr | H | H | H | H | thiophene-2-yl |
| 175 | n-Pr | H | i-Pr | H | H | H | H | 5-methyl pyridine-3-yl |
| 176 | n-Pr | H | i-Pr | Me | H | H | H | 4-MeC6H4 |
| 177 | n-Pr | H | s-Bu | H | Me | Me | H | Ph |
| 178 | n-Pr | H | s-Bu | H | Me | Me | H | 4-ClC6H4 |
| 179 | n-Pr | H | s-Bu | H | Me | Me | H | 3,4-Cl2C6H3 |
| 180 | n-Pr | H | s-Bu | H | Me | Me | H | 2-MeC6H4 |
| 181 | n-Pr | H | s-Bu | H | Me | Me | H | 4-MeC6H4 |
| 182 | n-Pr | H | s-Bu | H | Me | Me | H | 4-t-BuC6H4 |
| 183 | n-Pr | H | s-Bu | H | Me | Me | H | 1-Naph |
| 184 | n-Pr | H | s-Bu | H | Me | Me | H | thiophene-2-yl |
| 185 | n-Pr | H | s-Bu | H | Me | Me | H | isothiazole-5-yl |
| 186 | n-Pr | H | s-Bu | Me | Me | Me | H | 4-MeC6H4 |
| 187 | n-Pr | H | i-Bu | H | H | H | H | 4-ClC6H4 |
| 188 | n-Pr | H | i-Bu | H | H | H | H | 3,4-Cl2C6H3 |
| 189 | n-Pr | H | i-Bu | H | H | H | H | 2-MeC6H4 |
| 190 | n-Pr | H | i-Bu | H | H | H | H | 4-MeC6H4 |
| 191 | n-Pr | H | i-Bu | H | H | H | H | 4-t-BuC6H4 |
| 192 | n-Pr | H | i-Bu | H | H | H | H | 1-Naph |
| 193 | n-Pr | H | i-Bu | H | H | H | H | thiophene-2-yl |
| 194 | n-Pr | H | i-Bu | H | H | H | H | isothiazole-5-yl |
| 195 | n-Pr | H | i-Bu | Me | H | H | H | 4-MeC6H4 |
| 196 | n-Pr | H | t-Bu | H | H | H | H | Ph |
| 197 | n-Pr | H | t-Bu | H | H | H | H | 4-ClC6H4 |
| 198 | n-Pr | H | t-Bu | H | H | H | H | 3,4-Cl2C6H3 |
| 199 | n-Pr | H | t-Bu | H | H | H | H | 2-MeC6H4 |
| 200 | n-Pr | H | t-Bu | H | H | H | H | 4-MeC6H4 |
| 201 | n-Pr | H | t-Bu | H | H | H | H | 4-t-BuC6H4 |
| 202 | n-Pr | H | t-Bu | H | H | H | H | 1-Naph |
| 203 | n-Pr | H | t-Bu | H | H | H | H | thiophene-2-yl |
| 204 | n-Pr | H | t-Bu | H | H | H | H | isothiazole-5-yl |

TABLE 1-continued

| Comp. No. | R17 | R18 | R19 | R20 | R21 | R22 | R23 | R24 |
|---|---|---|---|---|---|---|---|---|
| 205 | n-Pr | H | t-Bu | Me | H | H | H | 4-MeC6H4 |
| 206 | n-Pr | H | Ph | H | H | H | H | Ph |
| 207 | n-Pr | H | Ph | H | H | H | H | 2-ClC6H4 |
| 208 | n-Pr | H | Ph | H | H | H | H | 4-ClC6H4 |
| 209 | n-Pr | H | Ph | H | H | H | H | 4-MeC6H4 |
| 210 | n-Pr | H | Ph | H | H | H | H | 4-EtC6H4 |
| 211 | i-Pr | H | Me | H | H | H | H | Ph |
| 212 | i-Pr | H | Me | H | H | H | H | 2-ClC6H4 |
| 213 | i-Pr | H | Me | H | Me | H | H | 3-ClC6H4 |
| 214 | i-Pr | H | Me | H | H | H | H | 4-ClC6H4 |
| 215 | i-Pr | H | Me | H | H | H | H | 4-MeC6H4 |
| 216 | i-Pr | H | Me | H | H | H | H | 4-t-BuC6H4 |
| 217 | i-Pr | H | Me | H | H | H | H | 1-Naph |
| 218 | i-Pr | H | Me | H | H | H | H | thiophene-2-yl |
| 219 | i-Pr | H | Me | H | H | H | H | pyridine-3-yl |
| 220 | i-Pr | H | Me | Me | H | H | H | 4-ClC6H4 |
| 221 | i-Pr | H | Et | H | H | H | H | Ph |
| 222 | i-Pr | H | Et | H | H | H | H | 2-ClC6H4 |
| 223 | i-Pr | H | Et | H | H | H | H | 3-ClC6H4 |
| 224 | i-Pr | H | Et | H | H | H | H | 4-ClC6H4 |
| 225 | i-Pr | H | Et | H | H | H | H | 4-MeC6H4 |
| 226 | i-Pr | H | Et | H | H | H | H | 4-t-BuC6H4 |
| 227 | i-Pr | H | Et | H | H | H | H | 1-Naph |
| 228 | i-Pr | H | Et | H | H | H | H | thiophene-2-yl |
| 229 | i-Pr | H | Et | H | H | H | H | 2-methyl pyridine-5-yl |
| 230 | i-Pr | H | Et | Me | H | H | H | 4-ClC6H4 |
| 231 | i-Pr | H | n-Pr | H | H | H | H | Ph |
| 232 | i-Pr | H | n-Pr | H | H | H | H | 2-ClC6H4 |
| 233 | i-Pr | H | n-Pr | H | H | H | H | 4-ClC6H4 |
| 234 | i-Pr | H | n-Pr | H | H | H | H | 4-MeC6H4 |
| 235 | i-Pr | H | n-Pr | H | H | H | H | 4-EtC6H4 |
| 236 | i-Pr | H | i-Pr | H | H | H | H | Ph |
| 237 | i-Pr | H | i-Pr | H | H | H | H | 4-ClC6H4 |
| 238 | i-Pr | H | i-Pr | H | H | H | H | 3,4-Cl2C6H3 |
| 239 | i-Pr | H | i-Pr | H | H | H | H | 2-MeC6H4 |
| 240 | i-Pr | H | i-Pr | H | H | H | H | 4-MeC6H4 |
| 241 | i-Pr | H | i-Pr | H | H | H | H | 4-EtC6H4 |
| 242 | i-Pr | H | i-Pr | H | H | H | H | 2-Naph |
| 243 | i-Pr | H | i-Pr | H | H | H | H | 5-methyl thiophene-2-yl |
| 244 | i-Pr | H | i-Pr | H | H | H | H | pyridine-3-yl |
| 245 | i-Pr | H | i-Pr | Me | H | H | H | 4-MeC6H4 |
| 246 | i-Pr | H | i-Pr | H | Me | H | H | 4-MeC6H4 |
| 247 | i-Pr | H | i-Pr | H | Me | H | H | 4-ClC6H4 |
| 248 | i-Pr | H | s-Bu | H | H | H | H | 3,4-Cl2C6H3 |
| 249 | i-Pr | H | s-Bu | H | H | H | H | 2-MeC6H4 |
| 250 | i-Pr | H | s-Bu | H | H | H | H | 4-MeC6H4 |
| 251 | i-Pr | H | s-Bu | H | H | H | H | 4-t-BuC6H4 |
| 252 | i-Pr | H | s-Bu | H | H | H | H | 1-Naph |
| 253 | i-Pr | H | s-Bu | H | H | H | H | thiophene-2-yl |
| 254 | i-Pr | H | s-Bu | H | H | H | H | isothiazole-5-yl |
| 255 | i-Pr | H | s-Bu | Me | H | H | H | 4-CF3C6H4 |
| 256 | i-Pr | H | i-Bu | H | H | H | H | Ph |
| 257 | i-Pr | H | i-Bu | H | H | H | H | 4-ClC6H4 |
| 258 | i-Pr | H | i-Bu | H | H | H | H | 3,4-Cl2C6H3 |
| 259 | i-Pr | H | i-Bu | H | H | H | H | 2-MeC6H4 |
| 260 | i-Pr | H | i-Bu | H | H | H | H | 4-MeC6H4 |
| 261 | i-Pr | H | i-Bu | H | H | H | H | 4-t-BuC6H4 |
| 262 | i-Pr | H | i-Bu | H | H | H | H | 2-Naph |
| 263 | i-Pr | H | i-Bu | H | H | H | H | thiophene-2-yl |
| 264 | i-Pr | H | i-Bu | H | H | H | H | 3-methyl isothiazole-5-yl |
| 265 | i-Pr | H | i-Bu | Me | H | H | H | 4-ClC6H4 |
| 266 | i-Pr | H | t-Bu | H | H | H | H | Ph |
| 267 | i-Pr | H | t-Bu | H | H | H | H | 4-ClC6H4 |
| 268 | i-Pr | H | t-Bu | H | H | H | H | 3,4-Cl2C6H3 |
| 269 | i-Pr | H | t-Bu | H | H | H | H | 2-MeC6H4 |
| 270 | i-Pr | H | t-Bu | H | H | H | H | 4-MeC6H4 |
| 271 | i-Pr | H | t-Bu | H | H | H | H | 4-t-BuC6H4 |
| 272 | i-Pr | H | t-Bu | H | H | H | H | 1-Naph |
| 273 | i-Pr | H | t-Bu | H | H | H | H | thiophene-2-yl |
| 274 | i-Pr | H | t-Bu | H | H | H | H | isothiazole-5-yl |
| 275 | i-Pr | H | t-Bu | Me | H | H | H | 4-MeC6H4 |
| 276 | i-Pr | H | Ph | H | H | H | H | Ph |
| 277 | i-Pr | H | Ph | H | H | H | H | 2-ClC6H4 |
| 278 | i-Pr | H | Ph | H | H | H | H | 4-ClC6H4 |

TABLE 1-continued

| Comp. No. | R17 | R18 | R19 | R20 | R21 | R22 | R23 | R24 |
|---|---|---|---|---|---|---|---|---|
| 279 | i-Pr | H | Ph | H | H | H | H | 4-MeC6H4 |
| 280 | i-Pr | H | Ph | H | H | H | H | 4-EtC6H4 |
| 281 | i-Pr | H | 4-ClC6H4 | H | H | H | H | Ph |
| 282 | i-Pr | H | 4-ClC6H4 | H | H | H | H | 4-CF3C6H4 |
| 283 | i-Pr | H | 4-ClC6H4 | H | H | H | H | 2-MeC6H4 |
| 284 | i-Pr | H | 4-ClC6H4 | H | H | H | H | 4-MeC6H4 |
| 285 | i-Pr | H | 4-ClC6H4 | H | H | H | H | 4-t-BuC6H4 |
| 286 | i-Pr | H | Bn | H | H | H | H | Ph |
| 287 | i-Pr | H | Bn | H | H | H | H | 4-CF3C6H4 |
| 288 | i-Pr | H | Bn | H | H | H | H | 2-MeC6H4 |
| 289 | i-Pr | H | Bn | H | H | H | H | 4-MeC6H4 |
| 290 | i-Pr | H | Bn | H | H | H | H | 4-ClC6H4 |
| 291 | i-Pr | H | -(CH2)4- | | H | H | H | 4-ClC6H4 |
| 292 | i-Pr | H | -(CH2)5- | | H | H | H | 4-ClC6H4 |
| 293 | s-Bu | H | Me | H | H | H | H | Ph |
| 294 | s-Bu | H | Me | H | H | H | H | 2-ClC6H4 |
| 295 | s-Bu | H | Me | H | Me | H | H | 3-ClC6H4 |
| 296 | s-Bu | H | Me | H | H | H | H | 4-ClC6H4 |
| 297 | s-Bu | H | Me | H | H | H | H | 4-MeC6H4 |
| 298 | s-Bu | H | Me | H | H | H | H | 4-t-BuC6H4 |
| 299 | s-Bu | H | Me | H | H | H | H | 1-Naph |
| 300 | s-Bu | H | Me | H | H | H | H | 3-methyl thiophene-2-yl |
| 301 | s-Bu | H | Me | H | H | H | H | pyridine-3-yl |
| 302 | s-Bu | H | Me | Me | H | H | H | 4-ClC6H4 |
| 303 | s-Bu | Ac | Et | H | H | H | H | Ph |
| 304 | s-Bu | Ac | Et | H | H | H | H | 2-ClC6H4 |
| 305 | s-Bu | Ac | Et | H | H | H | H | 3-ClC6H4 |
| 306 | s-Bu | Ac | Et | H | H | H | H | 4-ClC6H4 |
| 307 | s-Bu | Ac | Et | H | H | H | H | 4-MeC6H4 |
| 308 | s-Bu | Ac | Et | H | H | H | H | 4-t-BuC6H4 |
| 309 | s-Bu | Ac | Et | H | H | H | H | 1-Naph |
| 310 | s-Bu | Ac | Et | H | H | H | H | thiophene-2-yl |
| 311 | s-Bu | Ac | Et | H | H | H | H | pyridine-3-yl |
| 312 | s-Bu | Ac | Et | Me | H | H | H | 4-ClC6H4 |
| 313 | s-Bu | H | i-Pr | H | H | H | H | Ph |
| 314 | s-Bu | H | i-Pr | H | H | H | H | 4-ClC6H4 |
| 315 | s-Bu | H | i-Pr | H | H | H | H | 3,4-Cl2C6H3 |
| 316 | s-Bu | H | i-Pr | H | H | H | H | 2-MeC6H4 |
| 317 | s-Bu | H | i-Pr | H | H | H | H | 4-MeC6H4 |
| 318 | s-Bu | H | i-Pr | H | H | H | H | 4-EtC6H4 |
| 319 | s-Bu | H | i-Pr | H | H | H | H | 2-Naph |
| 320 | s-Bu | H | i-Pr | H | H | H | H | thiophene-2-yl |
| 321 | s-Bu | H | i-Pr | H | H | H | H | 5-methyl pyridine-3-yl |
| 322 | s-Bu | H | i-Pr | Me | H | H | H | 4-MeC6H4 |
| 323 | s-Bu | H | s-Bu | H | H | H | Bz | Ph |
| 324 | s-Bu | H | s-Bu | H | H | H | Bz | 4-ClC6H4 |
| 325 | s-Bu | H | s-Bu | H | H | H | Bz | 3,4-Cl2C6H3 |
| 326 | s-Bu | H | s-Bu | H | H | H | Bz | 2-MeC6H4 |
| 327 | s-Bu | H | s-Bu | H | H | H | Bz | 4-MeC6H4 |
| 328 | s-Bu | H | s-Bu | H | H | H | Bz | 4-t-BuC6H4 |
| 329 | s-Bu | H | s-Bu | H | H | H | Bz | 1-Naph |
| 330 | s-Bu | H | s-Bu | H | H | H | Bz | thiophene-2-yl |
| 331 | s-Bu | H | s-Bu | H | H | H | Bz | isothiazole-5-yl |
| 332 | s-Bu | H | s-Bu | Me | H | H | Bz | 4-MeC6H4 |
| 333 | s-Bu | H | i-Bu | H | H | H | H | Ph |
| 334 | s-Bu | H | i-Bu | H | H | H | H | 4-ClC6H4 |
| 335 | s-Bu | H | i-Bu | H | H | H | H | 3,4-Cl2C6H3 |
| 336 | s-Bu | H | i-Bu | H | H | H | H | 2-MeC6H4 |
| 337 | s-Bu | H | i-Bu | H | H | H | H | 4-MeC6H4 |
| 338 | s-Bu | H | i-Bu | H | H | H | H | 4-t-BuC6H4 |
| 339 | s-Bu | H | i-Bu | H | H | H | H | 1-Naph |
| 340 | s-Bu | H | i-Bu | H | H | H | H | thiophene-2-yl |
| 341 | s-Bu | H | i-Bu | H | H | H | H | isothiazole-5-yl |
| 342 | s-Bu | H | i-Bu | Me | H | H | H | 4-MeC6H4 |
| 343 | s-Bu | H | t-Bu | H | H | H | H | Ph |
| 344 | s-Bu | H | t-Bu | H | H | H | H | 4-ClC6H4 |
| 345 | s-Bu | H | t-Bu | H | H | H | H | 3,4-Cl2C6H3 |
| 346 | s-Bu | H | t-Bu | H | H | H | H | 2-MeC6H4 |
| 347 | s-Bu | H | t-Bu | H | H | H | H | 4-MeC6H4 |
| 348 | s-Bu | H | t-Bu | H | H | H | H | 4-t-BuC6H4 |
| 349 | s-Bu | H | t-Bu | H | H | H | H | 1-Naph |
| 350 | s-Bu | H | t-Bu | H | H | H | H | thiophene-2-yl |
| 351 | s-Bu | H | t-Bu | H | H | H | H | isothiazole-5-yl |
| 352 | s-Bu | H | t-Bu | Me | H | H | H | 4-MeC6H4 |
| 353 | s-Bu | H | Ph | H | H | H | H | Ph |

TABLE 1-continued

| Comp. No. | R17 | R18 | R19 | R20 | R21 | R22 | R23 | R24 |
|---|---|---|---|---|---|---|---|---|
| 354 | s-Bu | H | Ph | H | H | H | H | 2-ClC6H4 |
| 355 | s-Bu | H | Ph | H | H | H | H | 4-ClC6H4 |
| 356 | s-Bu | H | Ph | H | H | H | H | 4-MeC6H4 |
| 357 | s-Bu | H | Ph | H | H | H | H | 4-EtC6H4 |
| 358 | i-Bu | H | Me | H | H | H | H | Ph |
| 359 | i-Bu | H | Me | H | H | H | H | 2-ClC6H4 |
| 360 | i-Bu | H | Me | Me | H | H | H | 3-ClC6H4 |
| 361 | i-Bu | H | Me | H | H | H | H | 4-ClC6H4 |
| 362 | i-Bu | H | Me | H | H | H | H | 4-MeC6H4 |
| 363 | i-Bu | H | Me | H | H | H | H | 4-t-BuC6H4 |
| 364 | i-Bu | H | Me | H | H | H | H | 1-Naph |
| 365 | i-Bu | H | Me | H | H | H | H | thiophene-2-yl |
| 366 | i-Bu | H | Me | H | H | H | H | pyridine-3-yl |
| 367 | i-Bu | H | Me | Me | H | H | H | 4-ClC6H4 |
| 368 | i-Bu | H | Et | H | H | H | H | Ph |
| 369 | i-Bu | H | Et | H | H | H | H | 2-ClC6H4 |
| 370 | i-Bu | H | Et | H | H | H | H | 3-ClC6H4 |
| 371 | i-Bu | H | Et | H | H | H | H | 4-ClC6H4 |
| 372 | i-Bu | H | Et | H | H | H | H | 4-MeC6H4 |
| 373 | i-Bu | H | Et | H | H | H | H | 4-t-BuC6H4 |
| 374 | i-Bu | H | Et | H | H | H | H | 1-Naph |
| 375 | i-Bu | H | Et | H | H | H | H | thiophene-2-yl |
| 376 | i-Bu | H | Et | H | H | H | H | 2-methyl pyridine-5-yl |
| 377 | i-Bu | H | Et | Me | H | H | H | 4-ClC6H4 |
| 378 | i-Bu | H | n-Pr | H | H | H | H | Ph |
| 379 | i-Bu | H | n-Pr | H | H | H | H | 2-ClC6H4 |
| 380 | i-Bu | H | n-Pr | H | H | H | H | 4-ClC6H4 |
| 381 | i-Bu | H | n-Pr | H | H | H | H | 4-MeC6H4 |
| 382 | i-Bu | H | n-Pr | H | H | H | H | 4-EtC6H4 |
| 383 | i-Bu | H | i-Pr | H | H | H | H | Ph |
| 384 | i-Bu | H | i-Pr | H | H | H | H | 4-ClC6H4 |
| 385 | i-Bu | H | i-Pr | H | H | H | H | 3,4-Cl2C6H3 |
| 386 | i-Bu | H | i-Pr | H | H | H | H | 2-MeC6H4 |
| 387 | i-Bu | H | i-Pr | H | H | H | H | 4-MeC6H4 |
| 388 | i-Bu | H | i-Pr | H | H | H | H | 4-EtC6H4 |
| 389 | i-Bu | H | i-Pr | H | H | H | H | 2-Naph |
| 390 | i-Bu | H | i-Pr | H | H | H | H | 5-methyl thiophene-2-yl |
| 391 | i-Bu | H | i-Pr | H | H | H | H | pyridine-3-yl |
| 392 | i-Bu | H | i-Pr | Me | H | H | H | 4-MeC6H4 |
| 393 | i-Bu | H | s-Bu | H | H | H | H | Ph |
| 394 | i-Bu | H | s-Bu | H | H | H | H | 4-ClC6H4 |
| 395 | i-Bu | H | s-Bu | H | H | H | H | 3,4-Cl2C6H3 |
| 396 | i-Bu | H | s-Bu | H | H | H | H | 2-MeC6H4 |
| 397 | i-Bu | H | s-Bu | H | H | H | H | 4-MeC6H4 |
| 398 | i-Bu | H | s-Bu | H | H | H | H | 4-t-BuC6H4 |
| 399 | i-Bu | H | s-Bu | H | H | H | H | 1-Naph |
| 400 | i-Bu | H | s-Bu | H | H | H | H | thiophene-2-yl |
| 401 | i-Bu | H | s-Bu | H | H | H | H | isothiazole-5-yl |
| 402 | i-Bu | H | s-Bu | Me | H | H | H | 4-CF3C6H4 |
| 403 | i-Bu | H | i-Bu | H | H | H | H | Ph |
| 404 | i-Bu | H | i-Bu | H | H | H | H | 4-ClC6H4 |
| 405 | i-Bu | H | i-Bu | H | H | H | H | 3,4-Cl2C6H3 |
| 406 | i-Bu | H | i-Bu | H | H | H | H | 2-MeC6H4 |
| 407 | i-Bu | H | i-Bu | H | H | H | H | 4-MeC6H4 |
| 408 | i-Bu | H | i-Bu | H | H | H | H | 4-t-BuC6H4 |
| 409 | i-Bu | H | i-Bu | H | H | H | H | 2-Naph |
| 410 | i-Bu | H | i-Bu | H | H | H | H | thiophene-2-yl |
| 411 | i-Bu | H | i-Bu | H | H | H | H | 3-methyl isothiazole-5-yl |
| 412 | i-Bu | H | i-Bu | Me | H | H | H | 4-ClC6H4 |
| 413 | i-Bu | H | t-Bu | H | H | H | H | Ph |
| 414 | i-Bu | H | t-Bu | H | H | H | H | 4-ClC6H4 |
| 415 | i-Bu | H | t-Bu | H | H | H | H | 3,4-Cl2C6H3 |
| 416 | i-Bu | H | t-Bu | H | H | H | H | 2-MeC6H4 |
| 417 | i-Bu | H | t-Bu | H | H | H | H | 4-MeC6H4 |
| 418 | i-Bu | H | t-Bu | H | H | H | H | 4-t-BuC6H4 |
| 419 | i-Bu | H | t-Bu | H | H | H | H | 1-Naph |
| 420 | i-Bu | H | t-Bu | H | H | H | H | thiophene-2-yl |
| 421 | i-Bu | H | t-Bu | H | H | H | H | isothiazole-5-yl |
| 422 | i-Bu | H | t-Bu | Me | H | H | H | 4-MeC6H4 |
| 423 | i-Bu | H | Ph | H | H | H | H | Ph |
| 424 | i-Bu | H | Ph | H | H | H | H | 2-ClC6H4 |
| 425 | i-Bu | H | Ph | H | H | H | H | 4-ClC6H4 |
| 426 | i-Bu | H | Ph | H | H | H | H | 4-MeC6H4 |
| 427 | i-Bu | H | Ph | H | H | H | H | 4-EtC6H4 |

TABLE 1-continued

| Comp. No. | R17 | R18 | R19 | R20 | R21 | R22 | R23 | R24 |
|---|---|---|---|---|---|---|---|---|
| 428 | i-Bu | H | 4-ClC6H4 | H | H | H | H | Ph |
| 429 | i-Bu | H | 4-ClC6H4 | H | H | H | H | 4-CF3C6H4 |
| 430 | i-Bu | H | 4-ClC6H4 | H | H | H | H | 2-MeC6H4 |
| 431 | i-Bu | H | 4-ClC6H4 | H | H | H | H | 4-MeC6H4 |
| 432 | i-Bu | H | 4-ClC6H4 | H | H | H | H | 4-t-BuC6H4 |
| 433 | i-Bu | H | Bn | H | H | H | H | Ph |
| 434 | i-Bu | H | Bn | H | H | H | H | 4-CF3C6H4 |
| 435 | i-Bu | H | Bn | H | H | H | H | 2-MeC6H4 |
| 436 | i-Bu | H | Bn | H | H | H | H | 4-MeC6H4 |
| 437 | i-Bu | H | Bn | H | H | H | H | 4-EtC6H4 |
| 438 | i-Bu | H | -(CH2)4- | | H | H | H | 4-ClC6H4 |
| 439 | i-Bu | H | -(CH2)5- | | H | H | H | 4-ClC6H4 |
| 440 | t-Bu | H | Me | H | H | H | H | Ph |
| 441 | t-Bu | H | Me | H | H | H | H | 2-ClC6H4 |
| 442 | t-Bu | H | Me | H | Et | H | H | 3-ClC6H4 |
| 443 | t-Bu | H | Me | H | H | H | H | 4-ClC6H4 |
| 444 | t-Bu | H | Me | H | H | H | H | 4-MeC6H4 |
| 445 | t-Bu | H | Me | H | H | H | H | 4-t-BuC6H4 |
| 446 | t-Bu | H | Me | H | H | H | H | 1-Naph |
| 447 | t-Bu | H | Me | H | H | H | H | 5-methyl thiophene-2-yl |
| 448 | t-Bu | H | Me | H | H | H | H | pyridine-3-yl |
| 449 | t-Bu | H | Me | Me | H | H | H | 4-ClC6H4 |
| 450 | t-Bu | Me | Et | H | H | H | H | Ph |
| 451 | t-Bu | Me | Et | H | H | H | H | 2-ClC6H4 |
| 452 | t-Bu | Me | Et | H | H | H | H | 3-ClC6H4 |
| 453 | t-Bu | Me | Et | H | H | H | H | 4-ClC6H4 |
| 454 | t-Bu | Me | Et | H | H | H | H | 4-MeC6H4 |
| 455 | t-Bu | Me | Et | H | H | H | H | 4-t-BuC6H4 |
| 456 | t-Bu | Me | Et | H | H | H | H | 1-Naph |
| 457 | t-Bu | Me | Et | H | H | H | H | thiophene-2-yl |
| 458 | t-Bu | Me | Et | H | H | H | H | pyridine-3-yl |
| 459 | t-Bu | Me | Et | Me | H | H | H | 4-ClC6H4 |
| 460 | t-Bu | H | i-Pr | H | H | H | H | Ph |
| 461 | t-Bu | H | i-Pr | H | H | H | H | 4-ClC6H4 |
| 462 | t-Bu | H | i-Pr | H | H | H | H | 3,4-Cl2C6H3 |
| 463 | t-Bu | H | i-Pr | H | H | H | H | 2-MeC6H4 |
| 464 | t-Bu | H | i-Pr | H | H | H | H | 4-MeC6H4 |
| 465 | t-Bu | H | i-Pr | H | H | H | H | 4-EtC6H4 |
| 466 | t-Bu | H | i-Pr | H | H | H | H | 2-Naph |
| 467 | t-Bu | H | i-Pr | H | H | H | H | thiophene-2-yl |
| 468 | t-Bu | H | i-Pr | H | H | H | H | 5-methyl pyridine-3-yl |
| 469 | t-Bu | H | i-Pr | Me | H | H | H | 4-MeC6H4 |
| 470 | t-Bu | H | i-Pr | H | Me | H | H | 4-MeC6H4 |
| 471 | t-Bu | H | i-Pr | H | Me | H | H | 4-ClC6H4 |
| 472 | t-Bu | H | s-Bu | H | H | H | Et | 3,4-Cl2C6H3 |
| 473 | t-Bu | H | s-Bu | H | H | H | Et | 2-MeC6H4 |
| 474 | t-Bu | H | s-Bu | H | H | H | Et | 4-MeC6H4 |
| 475 | t-Bu | H | s-Bu | H | H | H | Et | 4-t-BuC6H4 |
| 476 | t-Bu | H | s-Bu | H | H | H | Et | 1-Naph |
| 478 | t-Bu | H | s-Bu | H | H | H | Et | thiophene-2-yl |
| 479 | t-Bu | H | s-Bu | H | H | H | Et | isothiazole-5-yl |
| 480 | t-Bu | H | s-Bu | Me | H | H | Et | 4-MeC6H4 |
| 481 | t-Bu | H | i-Bu | H | H | H | H | Ph |
| 482 | t-Bu | H | i-Bu | H | H | H | H | 4-ClC6H4 |
| 483 | t-Bu | H | i-Bu | H | H | H | H | 3,4-Cl2C6H3 |
| 484 | t-Bu | H | i-Bu | H | H | H | H | 2-MeC6H4 |
| 485 | t-Bu | H | i-Bu | H | H | H | H | 4-MeC6H4 |
| 486 | t-Bu | H | i-Bu | H | H | H | H | 4-t-BuC6H4 |
| 487 | t-Bu | H | i-Bu | H | H | H | H | 1-Naph |
| 488 | t-Bu | H | i-Bu | H | H | H | H | thiophene-2-yl |
| 489 | t-Bu | H | i-Bu | H | H | H | H | isothiazole-5-yl |
| 490 | t-Bu | H | i-Bu | Me | H | H | H | 4-MeC6H4 |
| 491 | t-Bu | H | t-Bu | H | H | H | H | Ph |
| 492 | t-Bu | H | t-Bu | H | H | H | H | 4-ClC6H4 |
| 493 | t-Bu | H | t-Bu | H | H | H | H | 3,4-Cl2C6H3 |
| 494 | t-Bu | H | t-Bu | H | H | H | H | 2-MeC6H4 |
| 495 | t-Bu | H | t-Bu | H | H | H | H | 4-MeC6H4 |
| 496 | t-Bu | H | t-Bu | H | H | H | H | 4-t-BuC6H4 |
| 497 | t-Bu | H | t-Bu | H | H | H | H | 1-Naph |
| 498 | t-Bu | H | t-Bu | H | H | H | H | thiophene-2-yl |
| 499 | t-Bu | H | t-Bu | H | H | H | H | isothiazole-5-yl |
| 500 | t-Bu | H | t-Bu | Me | H | H | H | 4-MeC6H4 |
| 501 | t-Bu | H | Ph | H | H | H | H | Ph |
| 502 | t-Bu | H | Ph | H | H | H | H | 2-ClC6H4 |
| 503 | t-Bu | H | Ph | H | H | H | H | 4-ClC6H4 |

TABLE 1-continued

| Comp. No. | R17 | R18 | R19 | R20 | R21 | R22 | R23 | R24 |
|---|---|---|---|---|---|---|---|---|
| 504 | t-Bu | H | Ph | H | H | H | H | 4-MeC6H4 |
| 505 | t-Bu | H | Ph | H | H | H | H | 4-EtC6H4 |
| 506 | Ph | H | Me | H | H | H | H | Ph |
| 507 | Ph | H | Me | H | H | H | H | 2-ClC6H4 |
| 508 | Ph | H | Me | Me | H | H | H | 3-ClC6H4 |
| 509 | Ph | H | Me | H | H | H | H | 4-ClC6H4 |
| 510 | Ph | H | Me | H | H | H | H | 4-MeC6H4 |
| 511 | Ph | H | Me | H | H | H | H | 4-t-BuC6H4 |
| 512 | Ph | H | Me | H | H | H | H | 1-Naph |
| 513 | Ph | H | Me | H | H | H | H | 5-methyl thiophene-2-yl |
| 514 | Ph | H | Me | H | H | H | H | pyridine-3-yl |
| 515 | Ph | H | Me | Me | H | H | H | 4-ClC6H4 |
| 516 | Ph | H | Et | H | H | H | H | Ph |
| 517 | Ph | H | Et | H | H | H | H | 2-ClC6H4 |
| 518 | Ph | H | Et | H | H | H | H | 3-ClC6H4 |
| 519 | Ph | H | Et | H | H | H | H | 4-ClC6H4 |
| 520 | Ph | H | Et | H | H | H | H | 4-MeC6H4 |
| 521 | Ph | H | Et | H | H | H | H | 4-t-BuC6H4 |
| 522 | Ph | H | Et | H | H | H | H | 1-Naph |
| 523 | Ph | H | Et | H | H | H | H | thiophene-2-yl |
| 524 | Ph | H | Et | H | H | H | H | pyridine-3-yl |
| 525 | Ph | H | Et | Me | H | H | H | 4-ClC6H4 |
| 526 | Ph | H | i-Pr | H | H | H | H | Ph |
| 527 | Ph | H | i-Pr | H | H | H | H | 4-ClC6H4 |
| 528 | Ph | H | i-Pr | H | H | H | H | 3,4-Cl2C6H3 |
| 529 | Ph | H | i-Pr | H | H | H | H | 2-MeC6H4 |
| 530 | Ph | H | i-Pr | H | H | H | H | 4-MeC6H4 |
| 531 | Ph | H | i-Pr | H | H | H | H | 4-EtC6H4 |
| 532 | Ph | H | i-Pr | H | H | H | H | 2-Naph |
| 533 | Ph | H | i-Pr | H | H | H | H | thiophene-2-yl |
| 534 | Ph | H | i-Pr | H | H | H | H | 5-methyl pyridine-3-yl |
| 535 | Ph | H | i-Pr | Me | H | H | H | 4-MeC6H4 |
| 536 | Ph | H | allyl | H | H | H | H | Ph |
| 537 | Ph | H | allyl | H | H | H | H | 4-ClC6H4 |
| 538 | Ph | H | allyl | H | H | H | H | 3,4-Cl2C6H3 |
| 539 | Ph | H | allyl | H | H | H | H | 2-MeC6H4 |
| 540 | Ph | H | allyl | H | H | H | H | 4-MeC6H4 |
| 541 | Ph | H | allyl | H | H | H | H | 4-t-BuC6H4 |
| 542 | Ph | H | allyl | H | H | H | H | 1-Naph |
| 543 | Ph | H | allyl | H | H | H | H | thiophene-2-yl |
| 544 | Ph | H | allyl | H | H | H | H | isothiazole-5-yl |
| 545 | Ph | H | allyl | Me | H | H | H | 4-MeC6H4 |
| 546 | Ph | H | i-Bu | H | H | H | H | Ph |
| 547 | Ph | H | i-Bu | H | H | H | H | 4-ClC6H4 |
| 548 | Ph | H | i-Bu | H | H | H | H | 3,4-Cl2C6H3 |
| 549 | Ph | H | i-Bu | H | H | H | H | 2-MeC6H4 |
| 550 | Ph | H | i-Bu | H | H | H | H | 4-MeC6H4 |
| 551 | Ph | H | i-Bu | H | H | H | H | 4-t-BuC6H4 |
| 552 | Ph | H | i-Bu | H | H | H | H | 1-Naph |
| 553 | Ph | H | i-Bu | H | H | H | H | thiophene-2-yl |
| 554 | Ph | H | i-Bu | H | H | H | H | isothiazole-5-yl |
| 555 | Ph | H | i-Bu | Me | H | H | H | 4-MeC6H4 |
| 556 | Ph | H | propargyl | H | H | H | H | Ph |
| 557 | Ph | H | propargyl | H | H | H | H | 4-ClC6H4 |
| 558 | Ph | H | propargyl | H | H | H | H | 3,4-Cl2C6H3 |
| 559 | Ph | H | propargyl | H | H | H | H | 2-MeC6H4 |
| 560 | Ph | H | propargyl | H | H | H | H | 4-MeC6H4 |
| 561 | Ph | H | propargyl | H | H | H | H | 4-t-BuC6H4 |
| 562 | Ph | H | propargyl | H | H | H | H | 1-Naph |
| 563 | Ph | H | propargyl | H | H | H | H | thiophene-2-yl |
| 564 | Ph | H | propargyl | H | H | H | H | isothiazole-5-yl |
| 565 | Ph | H | propargyl | Me | H | H | H | 4-MeC6H4 |
| 566 | Ph | H | Ph | H | H | H | H | Ph |
| 567 | Ph | H | Ph | H | H | H | H | 2-ClC6H4 |
| 568 | Ph | H | Ph | H | H | H | H | 4-ClC6H4 |
| 569 | Ph | H | Ph | H | H | H | H | 4-MeC6H4 |
| 570 | Ph | H | Ph | H | H | H | H | 4-EtC6H4 |
| 571 | Bn | H | Me | H | H | H | H | Ph |
| 572 | Bn | H | Me | H | H | H | H | 2-ClC6H4 |
| 573 | Bn | H | Me | H | Me | H | H | 3-ClC6H4 |
| 574 | Bn | H | Me | H | H | H | H | 4-ClC6H4 |
| 575 | Bn | H | Me | H | H | H | H | 4-MeC6H4 |
| 576 | Bn | H | Me | H | H | H | H | 4-t-BuC6H4 |
| 577 | Bn | H | Me | H | H | H | H | 1-Naph |
| 578 | Bn | H | Me | H | H | H | H | thiophene-2-yl |

TABLE 1-continued

| Comp. No. | R17 | R18 | R19 | R20 | R21 | R22 | R23 | R24 |
|---|---|---|---|---|---|---|---|---|
| 579 | Bn | H | Me | H | H | H | H | pyridine-3-yl |
| 580 | Bn | H | Me | Me | H | H | H | 4-ClC6H4 |
| 581 | Bn | H | Et | H | H | H | H | Ph |
| 582 | Bn | H | Et | H | H | H | H | 2-ClC6H4 |
| 583 | Bn | H | Et | H | H | H | H | 3-ClC6H4 |
| 584 | Bn | H | Et | H | H | H | H | 4-ClC6H4 |
| 585 | Bn | H | Et | H | H | H | H | 4-MeC6H4 |
| 586 | Bn | H | Et | H | H | H | H | 4-t-BuC6H4 |
| 587 | Bn | H | Et | H | H | H | H | 1-Naph |
| 588 | Bn | H | Et | H | H | H | H | thiophene-2-yl |
| 589 | Bn | H | Et | H | H | H | H | 4-methyl pyridine-5-yl |
| 590 | Bn | H | Et | Me | H | H | H | 4-ClC6H4 |
| 591 | Bn | H | n-Pr | H | H | H | H | Ph |
| 592 | Bn | H | n-Pr | H | H | H | H | 2-ClC6H4 |
| 593 | Bn | H | n-Pr | H | H | H | H | 4-ClC6H4 |
| 594 | Bn | H | n-Pr | H | H | H | H | 4-MeC6H4 |
| 595 | Bn | H | n-Pr | H | H | H | H | 4-EtC6H4 |
| 596 | Bn | H | i-Pr | H | H | H | H | Ph |
| 597 | Bn | H | i-Pr | H | H | H | H | 4-ClC6H4 |
| 598 | Bn | H | i-Pr | H | H | H | H | 3,4-Cl2C6H3 |
| 599 | Bn | H | i-Pr | H | H | H | H | 2-MeC6H4 |
| 600 | Bn | H | i-Pr | H | H | H | H | 4-MeC6H4 |
| 601 | Bn | H | i-Pr | H | H | H | H | 4-EtC6H4 |
| 602 | Bn | H | i-Pr | H | H | H | H | 2-Naph |
| 603 | Bn | H | i-Pr | H | H | H | H | 5-methyl thiophene-2-yl pyridine-3-yl |
| 604 | Bn | H | i-Pr | H | H | H | H | pyridine-3-yl |
| 605 | Bn | H | i-Pr | Me | H | H | H | 4-MeC6H4 |
| 606 | Bn | H | s-Bu | H | H | H | H | Ph |
| 607 | Bn | H | s-Bu | H | H | H | H | 4-ClC6H4 |
| 608 | Bn | H | s-Bu | H | H | H | H | 3,4-Cl2C6H3 |
| 609 | Bn | H | s-Bu | H | H | H | H | 2-MeC6H4 |
| 610 | Bn | H | s-Bu | H | H | H | H | 4-MeC6H4 |
| 611 | Bn | H | s-Bu | H | H | H | H | 4-t-BuC6H4 |
| 612 | Bn | H | s-Bu | H | H | H | H | 1-Naph |
| 613 | Bn | H | s-Bu | H | H | H | H | thiophene-2-yl |
| 614 | Bn | H | s-Bu | H | H | H | H | isothiazole-5-yl |
| 615 | Bn | H | s-Bu | Me | H | H | H | 4-CF3C6H4 |
| 616 | Bn | H | i-Bu | H | H | H | H | Ph |
| 617 | Bn | H | i-Bu | H | H | H | H | 4-ClC6H4 |
| 618 | Bn | H | i-Bu | H | H | H | H | 3,4-Cl2C6H3 |
| 619 | Bn | H | i-Bu | H | H | H | H | 2-MeC6H4 |
| 620 | Bn | H | i-Bu | H | H | H | H | 4-MeC6H4 |
| 621 | Bn | H | i-Bu | H | H | H | H | 4-t-BuC6H4 |
| 622 | Bn | H | i-Bu | H | H | H | H | 2-Naph |
| 623 | Bn | H | i-Bu | H | H | H | H | thiophene-2-yl |
| 624 | Bn | H | i-Bu | H | H | H | H | 3-methyl isothiazole-5-yl |
| 625 | Bn | H | i-Bu | Me | H | H | H | 4-ClC6H4 |
| 626 | Bn | H | t-Bu | H | H | H | H | Ph |
| 627 | Bn | H | t-Bu | H | H | H | H | 4-ClC6H4 |
| 628 | Bn | H | t-Bu | H | H | H | H | 3,4-Cl2C6H3 |
| 629 | Bn | H | t-Bu | H | H | H | H | 2-MeC6H4 |
| 630 | Bn | H | t-Bu | H | H | H | H | 4-MeC6H4 |
| 631 | Bn | H | t-Bu | H | H | H | H | 4-t-BuC6H4 |
| 632 | Bn | H | t-Bu | H | H | H | H | 1-Naph |
| 633 | Bn | H | t-Bu | H | H | H | H | thiophene-2-yl |
| 634 | Bn | H | t-Bu | H | H | H | H | isothiazole-5-yl |
| 635 | Bn | H | t-Bu | Me | H | H | H | 4-MeC6H4 |
| 636 | Bn | H | Ph | H | H | H | H | Ph |
| 637 | Bn | H | Ph | H | H | H | H | 2-ClC6H4 |
| 638 | Bn | H | Ph | H | H | H | H | 4-ClC6H4 |
| 639 | Bn | H | Ph | H | H | H | H | 4-MeC6H4 |
| 640 | Bn | H | Ph | H | H | H | H | 4-EtC6H4 |
| 641 | Bn | H | 4-MeC6H4 | H | H | H | H | Ph |
| 642 | Bn | H | 4-MeC6H4 | H | H | H | H | 4-CF3C6H4 |
| 643 | Bn | H | 4-MeC6H4 | H | H | H | H | 2-MeC6H4 |
| 644 | Bn | H | 4-MeC6H4 | H | H | H | H | 4-MeC6H4 |
| 645 | Bn | H | 4-MeC6H4 | H | H | H | H | 4-t-BuC6H4 |
| 646 | Bn | H | Bn | H | H | H | H | Ph |
| 647 | Bn | H | Bn | H | H | H | H | 4-CF3C6H4 |
| 648 | Bn | H | Bn | H | H | H | H | 2-MeC6H4 |
| 649 | Bn | H | Bn | H | H | H | H | 4-MeC6H4 |
| 650 | Bn | H | Bn | H | H | H | H | 4-EtC6H4 |
| 651 | Bn | H | -(CH2)4- | | H | H | H | 4-ClC6H4 |
| 652 | Bn | H | -(CH2)5- | | H | H | H | 4-ClC6H4 |

TABLE 1-continued

| Comp. No. | R17 | R18 | R19 | R20 | R21 | R22 | R23 | R24 |
|---|---|---|---|---|---|---|---|---|
| 653 | 2-Naph | H | Me | H | H | H | H | Ph |
| 654 | 2-Naph | H | Me | H | H | H | H | 2-BrC6H4 |
| 655 | 2-Naph | H | Me | Me | H | H | H | 3-BrC6H4 |
| 656 | 2-Naph | H | Me | H | H | H | H | 4-BrC6H4 |
| 657 | 2-Naph | H | Me | H | H | H | H | 4-MeC6H4 |
| 658 | 2-Naph | H | Me | H | H | H | H | 4-t-BuC6H4 |
| 659 | 2-Naph | H | Me | H | H | H | H | 1-Naph |
| 660 | 2-Naph | H | Me | H | H | H | H | 5-methyl thiophene-2-yl |
| 661 | 2-Naph | H | Me | H | H | H | H | pyridine-3-yl |
| 662 | 2-Naph | H | Me | Me | H | H | H | 4-ClC6H4 |
| 663 | 2-Naph | H | Et | H | H | H | H | Ph |
| 664 | 2-Naph | H | Et | H | H | H | H | 2-FC6H4 |
| 665 | 2-Naph | H | Et | H | H | H | H | 3-FC6H4 |
| 666 | 2-Naph | H | Et | H | H | H | H | 4-FC6H4 |
| 667 | 2-Naph | H | Et | H | H | H | H | 4-MeC6H4 |
| 668 | 2-Naph | H | Et | H | H | H | H | 4-t-BuC6H4 |
| 669 | 2-Naph | H | Et | H | H | H | H | 1-Naph |
| 670 | 2-Naph | H | Et | H | H | H | H | thiophene-2-yl |
| 671 | 2-Naph | H | Et | H | H | H | H | pyridine-3-yl |
| 672 | 2-Naph | H | Et | Me | H | H | H | 4-ClC6H4 |
| 673 | 2-Naph | H | i-Pr | H | H | H | H | Ph |
| 674 | 2-Naph | H | i-Pr | H | H | H | H | 4-ClC6H4 |
| 675 | 2-Naph | H | i-Pr | H | H | H | H | 3,4-Cl2C6H3 |
| 676 | 2-Naph | H | i-Pr | H | H | H | H | 2-MeC6H4 |
| 677 | 2-Naph | H | i-Pr | H | H | H | H | 4-MeC6H4 |
| 678 | 2-Naph | H | i-Pr | H | H | H | H | 4-EtC6H4 |
| 679 | 2-Naph | H | i-Pr | H | H | H | H | 2-Naph |
| 680 | 2-Naph | H | i-Pr | H | H | H | H | thiophene-2-yl |
| 681 | 2-Naph | H | i-Pr | H | H | H | H | 5-methyl pyridine-3-yl |
| 682 | 2-Naph | H | i-Pr | Me | H | H | H | 4-MeC6H4 |
| 683 | 2-Naph | H | s-Bu | H | H | H | H | Ph |
| 684 | 2-Naph | H | s-Bu | H | H | H | H | 4-ClC6H4 |
| 685 | 2-Naph | H | s-Bu | H | H | H | H | 3,4-Cl2C6H3 |
| 686 | 2-Naph | H | s-Bu | H | H | H | H | 2-MeC6H4 |
| 687 | 2-Naph | H | s-Bu | H | H | H | H | 4-MeC6H4 |
| 688 | 2-Naph | H | s-Bu | H | H | H | H | 4-t-BuC6H4 |
| 689 | 2-Naph | H | s-Bu | H | H | H | H | 1-Naph |
| 690 | 2-Naph | H | s-Bu | H | H | H | H | thiophene-2-yl |
| 691 | 2-Naph | H | s-Bu | H | H | H | H | isothiazole-5-yl |
| 692 | 2-Naph | H | s-Bu | Me | H | H | H | 4-MeC6H4 |
| 693 | 2-Naph | H | i-Bu | H | H | H | H | Ph |
| 694 | 2-Naph | H | i-Bu | H | H | H | H | 4-ClC6H4 |
| 695 | 2-Naph | H | i-Bu | H | H | H | H | 3,4-Cl2C6H3 |
| 696 | 2-Naph | H | i-Bu | H | H | H | H | 2-MeC6H4 |
| 697 | 2-Naph | H | i-Bu | H | H | H | H | 4-MeC6H4 |
| 698 | 2-Naph | H | i-Bu | H | H | H | H | 4-t-BuC6H4 |
| 699 | 2-Naph | H | i-Bu | H | H | H | H | 1-Naph |
| 700 | 2-Naph | H | i-Bu | H | H | H | H | thiophene-2-yl |
| 701 | 2-Naph | H | i-Bu | H | H | H | H | isothiazole-5-yl |
| 702 | 2-Naph | H | i-Bu | Me | H | H | H | 4-MeC6H4 |
| 703 | 2-Naph | H | c-Hex | H | H | H | H | Ph |
| 704 | 2-Naph | H | c-Hex | H | H | H | H | 4-ClC6H4 |
| 705 | 2-Naph | H | c-Hex | H | H | H | H | 3,4-Cl2C6H3 |
| 706 | 2-Naph | H | c-Hex | H | H | H | H | 2-MeC6H4 |
| 707 | 2-Naph | H | c-Hex | H | H | H | H | 4-MeC6H4 |
| 708 | 2-Naph | H | c-Hex | H | H | H | H | 4-t-BuC6H4 |
| 709 | 2-Naph | H | c-Hex | H | H | H | H | 1-Naph |
| 710 | 2-Naph | H | c-Hex | H | H | H | H | thiophene-2-yl |
| 711 | 2-Naph | H | c-Hex | H | H | H | H | isothiazole-5-yl |
| 712 | 2-Naph | H | c-Hex | Me | H | H | H | 4-MeC6H4 |
| 713 | 2-Naph | H | Ph | H | H | H | H | Ph |
| 714 | 2-Naph | H | Ph | H | H | H | H | 2-ClC6H4 |
| 715 | 2-Naph | H | Ph | H | H | H | H | 4-ClC6H4 |
| 716 | 2-Naph | H | Ph | H | H | H | H | 4-MeC6H4 |
| 717 | 2-Naph | H | Ph | H | H | H | H | 4-EtC6H4 |
| 718 | allyl | H | Me | H | H | H | H | Ph |
| 719 | allyl | H | Me | H | H | H | H | 2-ClC6H4 |
| 720 | allyl | H | Me | Me | H | H | H | 3-ClC6H4 |
| 721 | allyl | H | Me | H | H | H | H | 4-ClC6H4 |
| 722 | allyl | H | Me | H | H | H | H | 4-CNC6H4 |
| 723 | allyl | H | Me | H | H | H | H | 4-t-BuC6H4 |
| 724 | allyl | H | Me | H | H | H | H | 1-Naph |
| 725 | allyl | H | Me | H | H | H | H | 5-methyl thiophene-2-yl |
| 726 | allyl | H | Me | H | H | H | H | pyridine-3-yl |

TABLE 1-continued

| Comp. No. | R17 | R18 | R19 | R20 | R21 | R22 | R23 | R24 |
|---|---|---|---|---|---|---|---|---|
| 727 | allyl | H | Me | Me | H | H | H | 4-CF3C6H4 |
| 728 | allyl | H | Et | H | H | H | H | Ph |
| 729 | allyl | H | Et | H | H | H | H | 2-ClC6H4 |
| 730 | allyl | H | Et | H | H | H | H | 3-ClC6H4 |
| 731 | allyl | H | Et | H | H | H | H | 4-ClC6H4 |
| 732 | allyl | H | Et | H | H | H | H | 4-MeC6H4 |
| 733 | allyl | H | Et | H | H | H | H | 4-t-BuC6H4 |
| 734 | allyl | H | Et | H | H | H | H | 1-Naph |
| 735 | allyl | H | Et | H | H | H | H | thiophene-2-yl |
| 736 | allyl | H | Et | H | H | H | H | pyridine-3-yl |
| 737 | allyl | H | Et | Me | H | H | H | 4-ClC6H4 |
| 738 | allyl | H | i-Pr | H | H | H | H | Ph |
| 739 | allyl | H | i-Pr | H | H | H | H | 4-ClC6H4 |
| 740 | allyl | H | i-Pr | H | H | H | H | 3,4-Cl2C6H3 |
| 741 | allyl | H | i-Pr | H | H | H | H | 2-MeC6H4 |
| 742 | allyl | H | i-Pr | H | H | H | H | 4-MeC6H4 |
| 743 | allyl | H | i-Pr | H | H | H | H | 4-EtC6H4 |
| 744 | allyl | H | i-Pr | H | H | H | H | 2-Naph |
| 745 | allyl | H | i-Pr | H | H | H | H | thiophene-2-yl |
| 746 | allyl | H | i-Pr | H | H | H | H | 5-methyl pyridine-3-yl |
| 747 | allyl | H | i-Pr | Me | H | H | H | 4-MeC6H4 |
| 748 | allyl | H | s-Bu | H | H | H | H | Ph |
| 749 | allyl | H | s-Bu | H | H | H | H | 4-ClC6H4 |
| 750 | allyl | H | s-Bu | H | H | H | H | 3,4-Cl2C6H3 |
| 751 | allyl | H | s-Bu | H | H | H | H | 2-MeC6H4 |
| 752 | allyl | H | s-Bu | H | H | H | H | 4-MeC6H4 |
| 753 | allyl | H | s-Bu | H | H | H | H | 4-t-BuC6H4 |
| 754 | allyl | H | s-Bu | H | H | H | H | 1-Naph |
| 755 | allyl | H | s-Bu | H | H | H | H | thiophene-2-yl |
| 756 | allyl | H | s-Bu | H | H | H | H | isothiazole-5-yl |
| 757 | allyl | H | s-Bu | Me | H | H | H | 4-MeC6H4 |
| 758 | allyl | H | i-Bu | H | H | H | H | Ph |
| 759 | allyl | H | i-Bu | H | H | H | H | 4-ClC6H4 |
| 760 | allyl | H | i-Bu | H | H | H | H | 3,4-Cl2C6H3 |
| 761 | allyl | H | i-Bu | H | H | H | H | 2-MeC6H4 |
| 762 | allyl | H | i-Bu | H | H | H | H | 4-MeC6H4 |
| 763 | allyl | H | i-Bu | H | H | H | H | 4-t-BuC6H4 |
| 764 | allyl | H | i-Bu | H | H | H | H | 1-Naph |
| 765 | allyl | H | i-Bu | H | H | H | H | thiophene-2-yl |
| 766 | allyl | H | i-Bu | H | H | H | H | isothiazole-5-yl |
| 767 | allyl | H | i-Bu | Me | H | H | H | 4-MeC6H4 |
| 768 | allyl | H | t-Bu | H | H | H | H | Ph |
| 769 | allyl | H | t-Bu | H | H | H | H | 4-ClC6H4 |
| 770 | allyl | H | t-Bu | H | H | H | H | 3,4-Cl2C6H3 |
| 771 | allyl | H | t-Bu | H | H | H | H | 2-MeC6H4 |
| 772 | allyl | H | t-Bu | H | H | H | H | 4-MeC6H4 |
| 773 | allyl | H | t-Bu | H | H | H | H | 4-t-BuC6H4 |
| 774 | allyl | H | t-Bu | H | H | H | H | 1-Naph |
| 775 | allyl | H | t-Bu | H | H | H | H | thiophene-2-yl |
| 776 | allyl | H | t-Bu | H | H | H | H | isothiazole-5-yl |
| 777 | allyl | H | t-Bu | Me | H | H | H | 4-MeC6H4 |
| 778 | allyl | H | Ph | H | H | H | H | Ph |
| 779 | allyl | H | Ph | H | H | H | H | 2-ClC6H4 |
| 780 | allyl | H | 4-FC6H4 | H | H | H | H | 4-ClC6H4 |
| 781 | allyl | H | Ph | H | H | H | H | 4-MeC6H4 |
| 782 | allyl | H | 4-BrC6H4 | H | H | H | H | 4-EtC6H4 |
| 783 | propargyl | H | Me | H | H | H | H | Ph |
| 784 | propargyl | H | Me | H | H | H | H | 2-IC6H4 |
| 785 | propargyl | H | Me | H | Me | Me | H | 3-IC6H4 |
| 786 | propargyl | H | Me | H | H | H | H | 4-IC6H4 |
| 787 | propargyl | H | Me | H | H | H | H | 4-MeC6H4 |
| 788 | propargyl | H | Me | H | H | H | H | 4-t-BuC6H4 |
| 789 | propargyl | H | Me | H | H | H | H | 1-Naph |
| 790 | propargyl | H | Me | H | H | H | H | 5-methyl thiophene-2-yl |
| 791 | propargyl | H | Me | H | H | H | H | pyridine-3-yl |
| 792 | propargyl | H | Me | Me | H | H | H | 4-ClC6H4 |
| 793 | propargyl | H | Et | H | H | H | H | Ph |
| 794 | propargyl | H | Et | H | H | H | H | 2-ClC6H4 |
| 795 | propargyl | H | Et | H | H | H | H | 3-ClC6H4 |
| 796 | propargyl | H | Et | H | H | H | H | 4-ClC6H4 |
| 797 | propargyl | H | Et | H | H | H | H | 4-MeC6H4 |
| 798 | propargyl | H | Et | H | H | H | H | 4-t-BuC6H4 |
| 799 | propargyl | H | Et | H | H | H | H | 1-Naph |
| 800 | propargyl | H | Et | H | H | H | H | thiophene-2-yl |
| 801 | propargyl | H | Et | H | H | H | H | pyridine-3-yl |

TABLE 1-continued

| Comp. No. | R17 | R18 | R19 | R20 | R21 | R22 | R23 | R24 |
|---|---|---|---|---|---|---|---|---|
| 802 | propargyl | H | Et | Me | H | H | H | 4-ClC6H4 |
| 803 | propargyl | H | i-Pr | H | H | H | H | Ph |
| 804 | propargyl | H | i-Pr | H | H | H | H | 4-ClC6H4 |
| 805 | propargyl | H | i-Pr | H | H | H | H | 3,4-Cl2C6H3 |
| 806 | propargyl | H | i-Pr | H | H | H | H | 2-MeC6H4 |
| 807 | propargyl | H | i-Pr | H | H | H | H | 4-MeC6H4 |
| 808 | propargyl | H | i-Pr | H | H | H | H | 4-EtC6H4 |
| 809 | propargyl | H | i-Pr | H | H | H | H | 2-Naph |
| 810 | propargyl | H | i-Pr | H | H | H | H | thiophene-2-yl |
| 811 | propargyl | H | i-Pr | H | H | H | H | 5-methyl pyridine-3-yl |
| 812 | propargyl | H | i-Pr | Me | H | H | H | 4-MeC6H4 |
| 813 | propargyl | H | s-Bu | H | H | H | H | Ph |
| 814 | propargyl | H | s-Bu | H | H | H | H | 4-ClC6H4 |
| 815 | propargyl | H | s-Bu | H | H | H | H | 3,4-Cl2C6H3 |
| 816 | propargyl | H | s-Bu | H | H | H | H | 2-MeC6H4 |
| 817 | propargyl | H | s-Bu | H | H | H | H | 4-MeC6H4 |
| 818 | propargyl | H | s-Bu | H | H | H | H | 4-t-BuC6H4 |
| 819 | propargyl | H | s-Bu | H | H | H | H | 1-Naph |
| 820 | propargyl | H | s-Bu | H | H | H | H | thiophene-2-yl |
| 821 | propargyl | H | s-Bu | H | H | H | H | isothiazole-5-yl |
| 822 | propargyl | H | s-Bu | Me | H | H | H | 4-MeC6H4 |
| 823 | propargyl | H | i-Bu | H | H | H | H | Ph |
| 824 | propargyl | H | i-Bu | H | H | H | H | 4-ClC6H4 |
| 825 | propargyl | H | i-Bu | H | H | H | H | 3,4-Cl2C6H3 |
| 826 | propargyl | H | i-Bu | H | H | H | H | 2-MeC6H4 |
| 827 | propargyl | H | i-Bu | H | H | H | H | 4-MeC6H4 |
| 828 | propargyl | H | i-Bu | H | H | H | H | 4-t-BuC6H4 |
| 829 | propargyl | H | i-Bu | H | H | H | H | 1-Naph |
| 830 | propargyl | H | i-Bu | H | H | H | H | thiophene-2-yl |
| 831 | propargyl | H | i-Bu | H | H | H | H | isothiazole-5-yl |
| 832 | propargyl | H | i-Bu | Me | H | H | H | 4-MeC6H4 |
| 833 | propargyl | H | t-Bu | H | H | H | H | Ph |
| 834 | propargyl | H | t-Bu | H | H | H | H | 4-ClC6H4 |
| 835 | propargyl | H | t-Bu | H | H | H | H | 3,4-Cl2C6H3 |
| 836 | propargyl | H | t-Bu | H | H | H | H | 2-MeC6H4 |
| 837 | propargyl | H | t-Bu | H | H | H | H | 4-MeC6H4 |
| 838 | propargyl | H | t-Bu | H | H | H | H | 4-t-BuC6H4 |
| 839 | propargyl | H | t-Bu | H | H | H | H | 1-Naph |
| 840 | propargyl | H | t-Bu | H | H | H | H | thiophene-2-yl |
| 841 | propargyl | H | t-Bu | H | H | H | H | isothiazole-5-yl |
| 842 | propargyl | H | t-Bu | Me | H | H | H | 4-MeC6H4 |
| 843 | propargyl | H | Ph | H | Bn | H | H | Ph |
| 844 | propargyl | H | Ph | H | H | H | H | 2-ClC6H4 |
| 845 | propargyl | H | 4-ClC6H4 | H | H | H | H | 4-ClC6H4 |
| 846 | propargyl | H | Ph | H | H | H | H | 4-MeC6H4 |
| 847 | propargyl | H | 4-MeC6H4 | H | H | H | H | 4-EtC6H4 |
| 848 | c-Pr | H | Me | H | H | H | H | Ph |
| 849 | c-Pr | H | Me | H | H | H | H | 2-ClC6H4 |
| 850 | c-Pr | H | Me | Me | H | H | H | 3-ClC6H4 |
| 851 | c-Pr | H | Me | H | H | H | H | 4-ClC6H4 |
| 852 | c-Pr | H | Me | H | H | H | H | 4-MeC6H4 |
| 853 | c-Pr | H | Me | H | H | H | H | 4-t-BuC6H4 |
| 854 | c-Pr | H | Me | H | H | H | H | 1-Naph |
| 855 | c-Pr | H | Me | H | H | H | H | 5-methyl thiophene-2-yl |
| 856 | c-Pr | H | Me | H | H | H | H | pyridine-3-yl |
| 857 | c-Pr | H | Me | Me | H | H | H | 4-ClC6H4 |
| 858 | c-Pr | H | Et | H | H | H | H | Ph |
| 859 | c-Pr | H | Et | H | H | H | H | 2-ClC6H4 |
| 860 | c-Pr | H | Et | H | H | H | H | 3-ClC6H4 |
| 861 | c-Pr | H | Et | H | H | H | H | 4-ClC6H4 |
| 862 | c-Pr | H | Et | H | H | H | H | 4-MeC6H4 |
| 863 | c-Pr | H | Et | H | H | H | H | 4-t-BuC6H4 |
| 864 | c-Pr | H | Et | H | H | H | H | 1-Naph |
| 865 | c-Pr | H | Et | H | H | H | H | thiophene-2-yl |
| 866 | c-Pr | H | Et | H | H | H | H | pyridine-3-yl |
| 867 | c-Pr | H | Et | Me | H | H | H | 4-ClC6H4 |
| 868 | c-Pr | H | i-Pr | H | H | H | H | Ph |
| 869 | c-Pr | H | i-Pr | H | H | H | H | 4-ClC6H4 |
| 870 | c-Pr | H | i-Pr | H | H | H | H | 3,4-Cl2C6H3 |
| 871 | c-Pr | H | i-Pr | H | H | H | H | 2-MeC6H4 |
| 872 | c-Pr | H | i-Pr | H | H | H | H | 4-MeC6H4 |
| 873 | c-Pr | H | i-Pr | H | H | H | H | 4-EtC6H4 |
| 874 | c-Pr | H | i-Pr | H | H | H | H | 2-Naph |
| 875 | c-Pr | H | i-Pr | H | H | H | H | thiophene-2-yl |

TABLE 1-continued

| Comp. No. | R17 | R18 | R19 | R20 | R21 | R22 | R23 | R24 |
|---|---|---|---|---|---|---|---|---|
| 876 | c-Pr | H | i-Pr | H | H | H | H | 5-methyl pyridine-3-yl |
| 878 | c-Pr | H | i-Pr | Me | H | H | H | 4-MeC6H4 |
| 879 | c-Pr | H | s-Bu | H | H | H | H | Ph |
| 880 | c-Pr | H | s-Bu | H | H | H | H | 4-ClC6H4 |
| 881 | c-Pr | H | s-Bu | H | H | H | H | 3,4-Cl2C6H3 |
| 882 | c-Pr | H | s-Bu | H | H | H | H | 2-MeC6H4 |
| 883 | c-Pr | H | s-Bu | H | H | H | H | 4-MeC6H4 |
| 884 | c-Pr | H | s-Bu | H | H | H | H | 4-t-BuC6H4 |
| 885 | c-Pr | H | s-Bu | H | H | H | H | 1-Naph |
| 886 | c-Pr | H | s-Bu | H | H | H | H | thiophene-2-yl |
| 887 | c-Pr | H | s-Bu | H | H | H | H | isothiazole-5-yl |
| 888 | c-Pr | H | s-Bu | Me | H | H | H | 4-MeC6H4 |
| 889 | c-Pr | H | i-Bu | H | H | H | H | Ph |
| 890 | c-Pr | H | i-Bu | H | H | H | H | 4-ClC6H4 |
| 891 | c-Pr | H | i-Bu | H | H | H | H | 3,4-Cl2C6H3 |
| 892 | c-Pr | H | i-Bu | H | H | H | H | 2-MeC6H4 |
| 893 | c-Pr | H | i-Bu | H | H | H | H | 4-MeC6H4 |
| 894 | c-Pr | H | i-Bu | H | H | H | H | 4-t-BuC6H4 |
| 895 | c-Pr | H | i-Bu | H | H | H | H | 1-Naph |
| 896 | c-Pr | H | i-Bu | H | H | H | H | thiophene-2-yl |
| 897 | c-Pr | H | i-Bu | H | H | H | H | isothiazole-5-yl |
| 898 | c-Pr | H | i-Bu | Me | H | H | H | 4-MeC6H4 |
| 899 | c-Pr | H | t-Bu | H | Bn | H | H | Ph |
| 900 | c-Pr | H | t-Bu | H | H | H | H | 4-ClC6H4 |
| 901 | c-Pr | H | t-Bu | H | H | H | H | 3,4-Cl2C6H3 |
| 902 | c-Pr | H | t-Bu | H | H | H | H | 2-MeC6H4 |
| 903 | c-Pr | H | t-Bu | H | H | H | H | 4-MeC6H4 |
| 904 | c-Pr | H | t-Bu | H | H | H | H | 4-t-BuC6H4 |
| 905 | c-Pr | H | t-Bu | H | H | H | H | 1-Naph |
| 906 | c-Pr | H | t-Bu | H | H | H | H | thiophene-2-yl |
| 907 | c-Pr | H | t-Bu | H | H | H | H | isothiazole-5-yl |
| 908 | c-Pr | H | t-Bu | Me | H | H | H | 4-MeC6H4 |
| 909 | c-Pr | H | Ph | H | H | H | H | Ph |
| 910 | c-Pr | H | Ph | H | H | H | H | 2-ClC6H4 |
| 911 | c-Pr | H | Ph | H | H | H | H | 4-ClC6H4 |
| 912 | c-Pr | H | Ph | H | H | H | H | 4-MeC6H4 |
| 913 | c-Pr | H | Ph | H | H | H | H | 4-EtC6H4 |
| 914 | c-Hex | H | Me | H | H | H | H | Ph |
| 915 | c-Hex | H | Me | H | H | H | H | 2-ClC6H4 |
| 916 | c-Hex | H | Me | H | Et | H | H | 3-ClC6H4 |
| 917 | c-Hex | H | Me | H | H | H | H | 4-ClC6H4 |
| 918 | c-Hex | H | Me | H | H | H | H | 4-MeC6H4 |
| 919 | c-Hex | H | Me | H | H | H | H | 4-t-BuC6H4 |
| 920 | c-Hex | H | Me | H | H | H | H | 1-Naph |
| 921 | c-Hex | H | Me | H | H | H | H | 5-methyl thiophene-2-yl |
| 922 | c-Hex | H | Me | H | H | H | H | pyridine-3-yl |
| 923 | c-Hex | H | Me | Me | H | H | H | 4-ClC6H4 |
| 924 | c-Hex | H | Et | H | H | H | H | Ph |
| 925 | c-Hex | H | Et | H | H | H | H | 2-ClC6H4 |
| 926 | c-Hex | H | Et | H | H | H | H | 3-ClC6H4 |
| 927 | c-Hex | H | Et | H | H | H | H | 4-ClC6H4 |
| 928 | c-Hex | H | Et | H | H | H | H | 4-MeC6H4 |
| 929 | c-Hex | H | Et | H | H | H | H | 4-t-BuC6H4 |
| 930 | c-Hex | H | Et | H | H | H | H | 1-Naph |
| 931 | c-Hex | H | Et | H | H | H | H | thiophene-2-yl |
| 932 | c-Hex | H | Et | H | H | H | H | pyridine-3-yl |
| 933 | c-Hex | H | Et | Me | H | H | H | 4-ClC6H4 |
| 934 | c-Hex | H | i-Pr | H | H | H | H | Ph |
| 935 | c-Hex | H | i-Pr | H | H | H | H | 4-ClC6H4 |
| 936 | c-Hex | H | i-Pr | H | H | H | H | 3,4-Cl2C6H3 |
| 937 | c-Hex | H | i-Pr | H | H | H | H | 2-MeC6H4 |
| 938 | c-Hex | H | i-Pr | H | H | H | H | 4-MeC6H4 |
| 939 | c-Hex | H | i-Pr | H | H | H | H | 4-EtC6H4 |
| 940 | c-Hex | H | i-Pr | H | H | H | H | 2-Naph |
| 941 | c-Hex | H | i-Pr | H | H | H | H | thiophene-2-yl |
| 942 | c-Hex | H | i-Pr | H | H | H | H | 5-methyl pyridine-3-yl |
| 943 | c-Hex | H | i-Pr | Me | H | H | H | 4-MeC6H4 |
| 944 | c-Hex | H | s-Bu | H | H | H | H | Ph |
| 945 | c-Hex | H | s-Bu | H | H | H | H | 4-ClC6H4 |
| 946 | c-Hex | H | s-Bu | H | H | H | H | 3,4-Cl2C6H3 |
| 947 | c-Hex | H | s-Bu | H | H | H | H | 2-MeC6H4 |
| 948 | c-Hex | H | s-Bu | H | H | H | H | 4-MeC6H4 |
| 949 | c-Hex | H | s-Bu | H | H | H | H | 4-t-BuC6H4 |
| 950 | c-Hex | H | s-Bu | H | Ph | H | H | 1-Naph |

TABLE 1-continued

| Comp. No. | R17 | R18 | R19 | R20 | R21 | R22 | R23 | R24 |
|---|---|---|---|---|---|---|---|---|
| 951 | c-Hex | H | s-Bu | H | H | H | H | thiophene-2-yl |
| 952 | c-Hex | H | s-Bu | H | H | H | H | isothiazole-5-yl |
| 953 | c-Hex | H | s-Bu | Me | H | H | H | 4-MeC6H4 |
| 954 | c-Hex | H | i-Bu | H | H | H | H | Ph |
| 955 | c-Hex | H | i-Bu | H | H | H | H | 4-ClC6H4 |
| 956 | c-Hex | H | i-Bu | H | H | H | H | 3,4-Cl2C6H3 |
| 957 | c-Hex | H | i-Bu | H | H | H | H | 2-MeC6H4 |
| 958 | c-Hex | H | i-Bu | H | H | H | H | 4-MeC6H4 |
| 959 | c-Hex | H | i-Bu | H | H | H | H | 4-t-BuC6H4 |
| 960 | c-Hex | H | i-Bu | H | H | H | H | 1-Naph |
| 961 | c-Hex | H | i-Bu | H | H | H | H | thiophene-2-yl |
| 962 | c-Hex | H | i-Bu | H | H | H | H | isothiazole-5-yl |
| 963 | c-Hex | H | i-Bu | Me | H | H | H | 4-MeC6H4 |
| 964 | c-Hex | H | t-Bu | H | H | H | H | Ph |
| 965 | c-Hex | H | t-Bu | H | H | H | H | 4-ClC6H4 |
| 966 | c-Hex | H | t-Bu | H | H | H | H | 3,4-Cl2C6H3 |
| 967 | c-Hex | H | t-Bu | H | H | H | H | 2-MeC6H4 |
| 968 | c-Hex | H | t-Bu | H | H | H | H | 4-MeC6H4 |
| 969 | c-Hex | H | t-Bu | H | H | H | H | 4-t-BuC6H4 |
| 970 | c-Hex | H | t-Bu | H | H | H | H | 1-Naph |
| 971 | c-Hex | H | t-Bu | H | H | H | H | thiophene-2-yl |
| 972 | c-Hex | H | t-Bu | H | H | H | H | isothiazole-5-yl |
| 973 | c-Hex | H | t-Bu | Me | H | H | H | 4-MeC6H4 |
| 974 | c-Hex | H | Ph | H | H | H | H | Ph |
| 975 | c-Hex | H | Ph | H | H | H | H | 2-ClC6H4 |
| 976 | c-Hex | H | Ph | H | H | H | H | 4-ClC6H4 |
| 977 | c-Hex | H | Ph | H | H | H | H | 4-MeC6H4 |
| 978 | c-Hex | H | Ph | H | H | H | H | 4-EtC6H4 |
| 979 | vinyl | H | Me | H | H | H | H | Ph |
| 980 | vinyl | H | Me | H | H | H | H | 2-ClC6H4 |
| 981 | vinyl | H | Me | Me | H | H | H | 3-ClC6H4 |
| 982 | vinyl | H | Me | H | H | H | H | 4-ClC6H4 |
| 983 | vinyl | H | Me | H | H | H | H | 4-MeC6H4 |
| 984 | vinyl | H | Me | H | H | H | H | 4-t-BuC6H4 |
| 985 | vinyl | H | Me | H | H | H | H | 1-Naph |
| 986 | vinyl | H | Me | H | H | H | H | 5-ethyl thiophene-2-yl |
| 987 | vinyl | H | Me | H | H | H | H | pyridine-3-yl |
| 988 | vinyl | H | Me | Me | H | H | H | 4-ClC6H4 |
| 989 | vinyl | H | Et | H | H | H | H | Ph |
| 990 | vinyl | H | Et | H | H | H | H | 2-ClC6H4 |
| 991 | vinyl | H | Et | H | H | H | H | 3-ClC6H4 |
| 992 | vinyl | H | Et | H | H | H | H | 4-ClC6H4 |
| 993 | vinyl | H | Et | H | H | H | H | 4-MeC6H4 |
| 994 | vinyl | H | Et | H | H | H | H | 4-t-BuC6H4 |
| 995 | vinyl | H | Et | H | H | H | H | 1-Naph |
| 996 | vinyl | H | Et | H | H | H | H | thiophene-2-yl |
| 997 | vinyl | H | Et | H | H | H | H | pyridine-3-yl |
| 998 | vinyl | H | Et | Me | H | H | H | 4-ClC6H4 |
| 999 | vinyl | H | i-Pr | H | H | H | H | Ph |
| 1000 | vinyl | H | i-Pr | H | H | H | H | 4-ClC6H4 |
| 1001 | vinyl | H | i-Pr | H | H | H | H | 3,4-Cl2C6H3 |
| 1002 | vinyl | H | i-Pr | H | H | H | H | 2-MeC6H4 |
| 1003 | vinyl | H | i-Pr | H | H | H | H | 4-MeC6H4 |
| 1004 | vinyl | H | i-Pr | H | H | H | H | 4-EtC6H4 |
| 1005 | vinyl | H | i-Pr | H | H | H | H | 2-Naph |
| 1006 | vinyl | H | i-Pr | H | H | H | H | thiophene-2-yl |
| 1007 | vinyl | H | i-Pr | H | H | H | H | 5-methyl pyridine-3-yl |
| 1008 | vinyl | H | i-Pr | Me | H | H | H | 4-MeC6H4 |
| 1009 | vinyl | H | s-Bu | H | H | H | H | 4-ClC6H4 |
| 1010 | vinyl | H | s-Bu | H | H | H | H | 3,4-Cl2C6H3 |
| 1011 | vinyl | H | s-Bu | H | H | H | H | 2-MeC6H4 |
| 1012 | vinyl | H | s-Bu | H | H | H | H | 4-MeC6H4 |
| 1013 | vinyl | H | s-Bu | H | H | H | H | 4-t-BuC6H4 |
| 1014 | vinyl | H | s-Bu | H | H | H | H | 1-Naph |
| 1015 | vinyl | H | s-Bu | H | H | H | H | thiophene-2-yl |
| 1016 | vinyl | H | s-Bu | H | H | H | H | isothiazole-5-yl |
| 1017 | vinyl | H | s-Bu | Me | H | H | H | 4-MeC6H4 |
| 1018 | vinyl | H | i-Bu | H | H | H | H | 4-ClC6H4 |
| 1019 | vinyl | H | i-Bu | H | Ph | H | H | 3,4-Cl2C6H3 |
| 1020 | vinyl | H | i-Bu | H | H | H | H | 2-MeC6H4 |
| 1021 | vinyl | H | i-Bu | H | H | H | H | 4-MeC6H4 |
| 1022 | vinyl | H | i-Bu | H | H | H | H | 4-t-BuC6H4 |
| 1023 | vinyl | H | i-Bu | H | H | H | H | 1-Naph |
| 1024 | vinyl | H | i-Bu | H | H | H | H | thiophene-2-yl |

TABLE 1-continued

| Comp. No. | R17 | R18 | R19 | R20 | R21 | R22 | R23 | R24 |
|---|---|---|---|---|---|---|---|---|
| 1025 | vinyl | H | i-Bu | H | H | H | H | isothiazole-5-yl |
| 1026 | vinyl | H | i-Bu | Me | H | H | H | 4-MeC6H4 |
| 1027 | vinyl | H | t-Bu | H | H | H | H | Ph |
| 1028 | vinyl | H | t-Bu | H | H | H | H | 4-ClC6H4 |
| 1029 | vinyl | H | t-Bu | H | H | H | H | 3,4-Cl2C6H3 |
| 1030 | vinyl | H | t-Bu | H | H | H | H | 2-MeC6H4 |
| 1031 | vinyl | H | t-Bu | H | H | H | H | 4-MeC6H4 |
| 1032 | vinyl | H | t-Bu | H | H | H | H | 4-t-BuC6H4 |
| 1033 | vinyl | H | t-Bu | H | H | H | H | 1-Naph |
| 1034 | vinyl | H | t-Bu | H | H | H | H | Thiophene-2-yl |
| 1035 | vinyl | H | t-Bu | H | H | H | H | Isothiazole-5-yl |
| 1036 | vinyl | H | t-Bu | Me | H | H | H | 4-MeC6H4 |
| 1037 | vinyl | H | Ph | H | H | H | H | Ph |
| 1038 | vinyl | H | Ph | H | H | H | H | 2-ClC6H4 |
| 1039 | vinyl | H | Ph | H | H | H | H | 4-ClC6H4 |
| 1040 | vinyl | H | Ph | H | H | H | H | 4-MeC6H4 |
| 1041 | vinyl | H | Ph | H | H | H | H | 4-EtC6H4 |
| 1042 | 4-MeC6H4CH2 | H | Me | H | H | H | H | Ph |
| 1043 | 4-MeC6H4CH2 | H | Me | H | H | H | H | 2-BrC6H4 |
| 1044 | 4-MeC6H4CH2 | H | Me | H | H | H | H | 3-BrC6H4 |
| 1045 | 4-MeC6H4CH2 | H | Me | H | H | H | H | 4-BrC6H4 |
| 1046 | 4-MeC6H4CH2 | H | Me | H | H | H | H | 4-MeC6H4 |
| 1047 | 4-MeC6H4CH2 | H | i-Pr | H | H | H | H | 2-ClC6H4 |
| 1048 | 4-MeC6H4CH2 | H | i-Pr | H | H | H | H | 3-ClC6H4 |
| 1049 | 4-MeC6H4CH2 | H | i-Pr | H | H | H | H | 4-ClC6H4 |
| 1050 | 4-MeC6H4CH2 | H | i-Pr | H | H | H | H | 4-MeC6H4 |
| 1051 | 4-MeC6H4CH2 | H | i-Pr | H | H | H | H | 4-EtC6H4 |
| 1052 | 4-MeC6H4CH2 | H | i-Bu | H | H | H | H | Ph |
| 1053 | 4-MeC6H4CH2 | H | i-Bu | H | H | H | H | 2-FC6H4 |
| 1054 | 4-MeC6H4CH2 | H | i-Bu | H | H | H | H | 3-FC6H4 |
| 1055 | 4-MeC6H4CH2 | H | i-Bu | H | H | H | H | 4-FC6H4 |
| 1056 | 4-MeC6H4CH2 | H | i-Bu | H | H | H | H | 4-MeC6H4 |
| 1057 | 4-ClC6H4CH2 | H | Me | H | H | H | H | Ph |
| 1058 | 4-ClC6H4CH2 | H | Me | H | H | H | H | 4-ClC6H4 |
| 1059 | 4-ClC6H4CH2 | H | Me | H | H | H | H | 4-MeC6H4 |
| 1060 | 4-ClC6H4CH2 | H | Me | H | H | H | H | thiophene-2-yl |
| 1061 | 4-ClC6H4CH2 | H | Me | H | H | H | H | pyridine-3-yl |
| 1062 | 4-ClC6H4CH2 | H | i-Pr | H | H | H | H | Ph |
| 1063 | 4-ClC6H4CH2 | H | i-Pr | H | H | H | H | 4-ClC6H4 |
| 1064 | 4-ClC6H4CH2 | H | i-Pr | H | H | H | H | 3,4-Cl2C6H3 |
| 1065 | 4-ClC6H4CH2 | H | i-Pr | H | H | H | H | 2-MeC6H4 |
| 1066 | 4-ClC6H4CH2 | H | i-Pr | H | H | H | H | 4-MeC6H4 |
| 1067 | 4-ClC6H4CH2 | H | i-Bu | H | H | H | H | Ph |
| 1068 | 4-ClC6H4CH2 | H | i-Bu | H | H | H | H | 2-MeC6H4 |
| 1069 | 4-ClC6H4CH2 | H | i-Bu | H | H | H | H | 3-MeC6H4 |
| 1070 | 4-ClC6H4CH2 | H | i-Bu | H | H | H | H | 4-MeC6H4 |
| 1071 | 4-ClC6H4CH2 | H | i-Bu | Me | H | H | H | 1-Naph |
| 1072 | PhCH(CH3) | H | Me | H | H | H | H | Ph |
| 1073 | PhCH(CH3) | H | Me | H | H | H | H | 4-ClC6H4 |
| 1074 | PhCH(CH3) | H | Me | H | H | H | H | 4-MeC6H4 |
| 1075 | PhCH(CH3) | H | Me | H | H | H | H | thiophene-2-yl |
| 1076 | PhCH(CH3) | H | Me | H | H | H | H | pyridine-4-yl |
| 1077 | PhCH(CH3) | H | i-Pr | H | H | H | H | Ph |
| 1078 | PhCH(CH3) | H | i-Pr | H | H | H | H | 4-ClC6H4 |
| 1079 | PhCH(CH3) | H | i-Pr | H | H | H | H | 3,4-Cl2C6H3 |
| 1080 | PhCH(CH3) | H | i-Pr | H | H | H | H | 2-MeC6H4 |
| 1081 | PhCH(CH3) | H | i-Pr | Me | H | H | H | 4-MeC6H4 |
| 1082 | PhCH(CH3) | H | i-Bu | H | H | H | H | Ph |
| 1083 | PhCH(CH3) | H | i-Bu | H | H | H | H | 2-ClC6H4 |
| 1084 | PhCH(CH3) | H | i-Bu | H | H | H | H | 3-ClC6H4 |
| 1085 | PhCH(CH3) | H | i-Bu | H | H | H | H | 4-ClC6H4 |
| 1086 | PhCH(CH3) | H | i-Bu | H | H | H | H | 1-Naph |
| 1087 | PhCH(i-Pr) | H | Me | H | H | H | H | Ph |
| 1088 | PhCH(i-Pr) | H | Me | H | H | H | H | 4-ClC6H4 |
| 1089 | PhCH(i-Pr) | H | Me | H | H | H | H | 4-MeC6H4 |
| 1090 | PhCH(i-Pr) | H | Me | H | H | H | H | thiophene-2-yl |
| 1091 | PhCH(i-Pr) | H | Me | H | H | H | H | pyridine-2-yl |
| 1092 | PhCH(i-Pr) | H | i-Pr | H | H | H | H | Ph |
| 1093 | PhCH(i-Pr) | H | i-Pr | H | H | H | H | 4-ClC6H4 |
| 1094 | PhCH(i-Pr) | H | i-Pr | H | H | H | H | 3,4-Cl2C6H3 |
| 1095 | PhCH(i-Pr) | H | i-Pr | H | H | H | H | 2-MeC6H4 |
| 1096 | PhCH(i-Pr) | H | i-Pr | H | H | H | H | 4-MeC6H4 |
| 1097 | PhCH(i-Pr) | H | i-Bu | H | H | H | H | Ph |
| 1098 | PhCH(i-Pr) | H | i-Bu | H | H | H | H | 2-ClC6H4 |

TABLE 1-continued

| Comp. No. | R17 | R18 | R19 | R20 | R21 | R22 | R23 | R24 |
|---|---|---|---|---|---|---|---|---|
| 1099 | PhCH(i-Pr) | H | i-Bu | H | H | H | H | 3-ClC6H4 |
| 1100 | PhCH(i-Pr) | H | i-Bu | H | H | H | H | 4-ClC6H4 |
| 1101 | PhCH(i-Pr) | H | i-Bu | H | H | H | H | 1-Naph |
| 1102 | PhC(CH3)2 | H | Me | H | H | H | H | Ph |
| 1103 | PhC(CH3)2 | H | Me | H | H | H | H | 4-ClC6H4 |
| 1104 | PhC(CH3)2 | H | Me | H | H | H | H | 4-MeC6H4 |
| 1105 | PhC(CH3)2 | H | Me | H | H | H | H | furan-2-yl |
| 1106 | PhC(CH3)2 | H | Me | H | H | H | H | pyridine-4-yl |
| 1107 | PhC(CH3)2 | H | i-Pr | H | H | H | H | Ph |
| 1108 | PhC(CH3)2 | H | i-Pr | H | H | H | H | 4-ClC6H4 |
| 1109 | PhC(CH3)2 | H | i-Pr | H | H | H | H | 3,4-Cl2C6H3 |
| 1110 | PhC(CH3)2 | H | i-Pr | H | H | H | H | 2-MeC6H4 |
| 1111 | PhC(CH3)2 | H | i-Pr | H | H | H | H | 4-MeC6H4 |
| 1112 | PhC(CH3)2 | H | i-Bu | H | H | H | H | Ph |
| 1113 | PhC(CH3)2 | H | i-Bu | H | H | H | H | 2-ClC6H4 |
| 1114 | PbC(CH3)2 | H | i-Bu | H | H | H | H | 3-ClC6H4 |
| 1115 | PhC(CH3)2 | H | i-Bu | H | H | H | H | 4-ClC6H4 |
| 1116 | PhC(CH3)2 | H | i-Bu | H | H | H | H | 2-Naph |
| 1117 | 2-furylmethyl | H | Me | H | H | H | H | Ph |
| 1118 | 2-furylmethyl | H | Me | H | H | H | H | 4-ClC6H4 |
| 1119 | 2-furylmethyl | H | Me | H | H | H | H | 4-MeC6H4 |
| 1120 | 2-furylmethyl | H | Me | H | H | H | H | thiophene-2-yl |
| 1121 | 2-furylmethyl | H | Me | H | H | H | H | pyridine-2-yl |
| 1122 | 2-furylmethyl | H | i-Pr | H | H | H | H | Ph |
| 1123 | 2-furylmethyl | H | i-Pr | H | H | H | H | 4-ClC6H4 |
| 1124 | 2-furylmethyl | H | i-Pr | H | H | H | H | 3,4-Cl2C6H3 |
| 1125 | 2-furylmethyl | H | i-Pr | H | H | H | H | 2-MeC6H4 |
| 1126 | 2-furylmethyl | H | i-Pr | H | H | H | H | 4-MeC6H4 |
| 1127 | 2-furylmethyl | H | i-Bu | H | H | H | H | Ph |
| 1128 | 2-furylmethyl | H | i-Bu | H | H | H | H | 2-ClC6H4 |
| 1129 | 2-furylmethyl | H | i-Bu | H | H | H | H | 3-ClC6H4 |
| 1130 | 2-furylmethyl | H | i-Bu | H | H | H | H | 4-ClC6H4 |
| 1131 | 2-furylmethyl | H | i-Bu | H | H | H | H | 1-Naph |
| 1132 | 3-furylmethyl | H | Me | H | H | H | H | Ph |
| 1133 | 3-furylmethyl | H | Me | H | H | H | H | 4-ClC6H4 |
| 1134 | 3-furylmethyl | H | Me | H | H | H | H | 4-MeC6H4 |
| 1135 | 3-furylmethyl | H | Me | H | H | H | H | furan-2-yl |
| 1136 | 3-furylmethyl | H | Me | H | H | H | H | pyridine-4-yl |
| 1137 | 3-furylmethyl | H | i-Pr | H | H | H | H | Ph |
| 1138 | 3-furylmethyl | H | i-Pr | H | H | H | H | 4-ClC6H4 |
| 1139 | 3-furylmethyl | H | i-Pr | H | H | H | H | 3,4-Cl2C6H3 |
| 1140 | 3-furylmethyl | H | i-Pr | H | H | H | H | 2-MeC6H4 |
| 1141 | 3-furylmethyl | H | i-Pr | H | H | H | H | 4-MeC6H4 |
| 1142 | 3-furylmethyl | H | i-Bu | H | H | H | H | Ph |
| 1143 | 3-furylmethyl | H | i-Bu | H | H | H | H | 2-ClC6H4 |
| 1144 | 3-furylmethyl | H | i-Bu | H | H | H | H | 3-ClC6H4 |
| 1145 | 3-furylmethyl | H | i-Bu | H | H | H | H | 4-ClC6H4 |
| 1146 | 3-furylmethyl | H | i-Bu | H | H | H | H | 2-Naph |
| 1147 | 2-tetrahydrofurylmethyl | H | Me | H | H | H | H | Ph |
| 1148 | 2-tetrahydrofurylmethyl | H | Me | H | H | H | H | 4-ClC6H4 |
| 1149 | 2-tetrahydrofurylmethyl | H | Me | H | H | H | H | 4-MeC6H4 |
| 1150 | 2-tetrahydrofurylmethyl | H | Me | H | H | H | H | thiophene-2-yl |
| 1151 | 2-tetrahydrofurylmethyl | H | Me | H | H | H | H | pyridine-2-yl |
| 1152 | 2-tetrahydrofurylmethyl | H | i-Pr | H | H | H | H | Ph |
| 1153 | 2-tetrahydrofurylmethyl | H | i-Pr | H | H | H | H | 4-ClC6H4 |
| 1154 | 2-tetrahydrofurylmethyl | H | i-Pr | H | H | H | H | 3,4-Cl2C6H3 |
| 1155 | 2-tetrahydrofurylmethyl | H | i-Pr | H | H | H | H | 2-MeC6H4 |
| 1156 | 2-tetrahydrofurylmethyl | H | i-Pr | H | H | H | H | 4-MeC6H4 |
| 1157 | 2-tetrahydrofurylmethyl | H | i-Bu | H | H | H | H | Ph |
| 1158 | 2-tetrahydrofurylmethyl | H | i-Bu | H | H | H | H | 2-ClC6H4 |
| 1159 | 2-tetrahydrofurylmethyl | H | i-Bu | H | H | H | H | 3-ClC6H4 |
| 1160 | 2-tetrahydrofurylmethyl | H | i-Bu | H | H | H | H | 4-ClC6H4 |
| 1161 | 2-tetrahydrofurylmethyl | H | i-Bu | H | H | H | H | 1-Naph |
| 1162 | 2-thienylmethyl | H | Me | H | H | H | H | Ph |
| 1163 | 2-thienylmethyl | H | Me | H | H | H | H | 4-ClC6H4 |
| 1164 | 2-thienylmethyl | H | Me | H | H | H | H | 4-MeC6H4 |
| 1165 | 2-thienylmethyl | H | Me | H | H | H | H | thiophene-2-yl |
| 1166 | 2-thienylmethyl | H | Me | H | H | H | H | pyridine-2-yl |
| 1167 | 2-thienylmethyl | H | i-Pr | H | H | H | H | Ph |
| 1168 | 2-thienylmethyl | H | i-Pr | H | H | H | H | 4-ClC6H4 |
| 1169 | 2-thienylmethyl | H | i-Pr | H | H | H | H | 3,4-Cl2C6H3 |
| 1170 | 2-thienylmethyl | H | i-Pr | H | H | H | H | 2-MeC6H4 |
| 1171 | 2-thienylmethyl | H | i-Pr | H | H | H | H | 4-MeC6H4 |
| 1172 | 2-thienylmethyl | H | i-Bu | H | H | H | H | Ph |
| 1173 | 2-thienylmethyl | H | i-Bu | H | H | H | H | 2-ClC6H4 |
| 1174 | 2-thienylmethyl | H | i-Bu | H | H | H | H | 3-ClC6H4 |
| 1175 | 2-thienylmethyl | H | i-Bu | H | H | H | H | 4-ClC6H4 |

TABLE 1-continued

| Comp. No. | R17 | R18 | R19 | R20 | R21 | R22 | R23 | R24 |
|---|---|---|---|---|---|---|---|---|
| 1176 | 2-thienylmethyl | H | i-Bu | H | H | H | H | 1-Naph |
| 1177 | cyclopropylmethyl | H | Me | H | H | H | H | Ph |
| 1178 | cyclopropylmethyl | H | Me | H | H | H | H | 4-ClC6H4 |
| 1179 | cyclopropylmethyl | H | Me | H | H | H | H | 4-MeC6H4 |
| 1180 | cyclopropylmethyl | H | Me | H | H | H | H | furan-2-yl |
| 1181 | cyclopropylmethyl | H | Me | H | H | H | H | pyridine-4-yl |
| 1182 | cyclopropylmethyl | H | i-Pr | H | H | H | H | Ph |
| 1183 | cyclopropylmethyl | H | i-Pr | H | H | H | H | 4-ClC6H4 |
| 1184 | cyclopropylmethyl | H | i-Pr | H | H | H | H | 3,4-Cl2C6H3 |
| 1185 | cyclopropylmethyl | H | i-Pr | H | H | H | H | 2-MeC6H4 |
| 1186 | cyclopropylmethyl | H | i-Pr | H | H | H | H | 4-MeC6H4 |
| 1187 | cyclopropylmethyl | H | i-Bu | H | H | H | H | Ph |
| 1188 | cyclopropylmethyl | H | i-Bu | H | H | H | H | 2-ClC6H4 |
| 1189 | cyclopropylmethyl | H | i-Bu | H | H | H | H | 3-ClC6H4 |
| 1190 | cyclopropylmethyl | H | i-Bu | H | H | H | H | 4-ClC6H4 |
| 1191 | cyclopropylmethyl | H | i-Bu | H | H | H | H | 2-Naph |
| 1192 | neopentyl | H | Me | H | H | H | H | Ph |
| 1193 | neopentyl | H | Me | H | H | H | H | 4-ClC6H4 |
| 1194 | neopentyl | H | Me | H | H | H | H | 4-MeC6H4 |
| 1195 | neopentyl | H | Me | H | H | H | H | thiophene-2-yl |
| 1196 | neopentyl | H | Me | H | H | H | H | pyridine-2-yl |
| 1197 | neopentyl | H | i-Pr | H | H | H | H | Ph |
| 1198 | neopentyl | H | i-Pr | H | H | H | H | 4-ClC6H4 |
| 1199 | neopentyl | H | i-Pr | H | H | H | H | 3,4-Cl2C6H3 |
| 1200 | neopentyl | H | i-Pr | H | H | H | H | 2-MeC6H4 |
| 1201 | neopentyl | H | i-Pr | H | H | H | H | 4-MeC6H4 |
| 1202 | neopentyl | H | i-Bu | H | H | H | H | Ph |
| 1203 | neopentyl | H | i-Bu | H | H | H | H | 2-ClC6H4 |
| 1204 | neopentyl | H | i-Bu | H | H | H | H | 3-ClC6H4 |
| 1205 | neopentyl | H | i-Bu | H | H | H | H | 4-ClC6H4 |
| 1206 | neopentyl | H | i-Bu | H | H | H | H | 1-Naph |
| 1207 | methallyl | H | Me | H | H | H | H | Ph |
| 1208 | methallyl | H | Me | H | H | H | H | 4-ClC6H4 |
| 1209 | methallyl | H | Me | H | H | H | H | 4-MeC6H4 |
| 1210 | methallyl | H | Me | H | H | H | H | furan-2-yl |
| 1211 | methallyl | H | Me | H | H | H | H | pyridine-4-yl |
| 1212 | methallyl | H | i-Pr | H | H | H | H | Ph |
| 1213 | methallyl | H | i-Pr | H | H | H | H | 4-ClC6H4 |
| 1214 | methallyl | H | i-Pr | H | H | H | H | 3,4-Cl2C6H3 |
| 1215 | methallyl | H | i-Pr | H | H | H | H | 2-MeC6H4 |
| 1216 | methallyl | H | i-Pr | H | H | H | H | 4-MeC6H4 |
| 1217 | methallyl | H | i-Bu | H | H | H | H | Ph |
| 1218 | methallyl | H | i-Bu | H | H | H | H | 2-ClC6H4 |
| 1219 | methallyl | H | i-Bu | H | H | H | H | 3-ClC6H4 |
| 1220 | methallyl | H | i-Bu | H | H | H | H | 4-ClC6H4 |
| 1221 | methallyl | H | i-Bu | H | H | H | H | 2-Naph |
| 1222 | 1,2-dimethylpropyl | H | Me | H | H | H | H | Ph |
| 1223 | 1,2-dimethylpropyl | H | Me | H | H | H | H | 4-ClC6H4 |
| 1224 | 1,2-dimethylpropyl | H | Me | H | H | H | H | 4-MeC6H4 |
| 1225 | 1,2-dimethylpropyl | H | Me | H | H | H | H | thiophene-2-yl |
| 1226 | 1,2-dimethylpropyl | H | Me | H | H | H | H | pyridine-2-yl |
| 1227 | 1,2-dimethylpropyl | H | i-Pr | H | H | H | H | Ph |
| 1228 | 1,2-dimethylpropyl | H | i-Pr | H | H | H | H | 4-ClC6H4 |
| 1229 | 1,2-dimethylpropyl | H | i-Pr | H | H | H | H | 3,4-Cl2C6H3 |
| 1230 | 1,2-dimethylpropyl | H | i-Pr | H | H | H | H | 2-MeC6H4 |
| 1231 | 1,2-dimethylpropyl | H | i-Pr | H | H | H | H | 4-MeC6H4 |
| 1232 | 1,2-dimethylpropyl | H | i-Bu | H | H | H | H | Ph |
| 1233 | 1,2-dimethylpropyl | H | i-Bu | H | H | H | H | 2-ClC6H4 |
| 1234 | 1,2-dimethylpropyl | H | i-Bu | H | H | H | H | 3-ClC6H4 |
| 1235 | 1,2-dimethylpropyl | H | i-Bu | H | H | H | H | 4-ClC6H4 |
| 1236 | 1,2-dimethylpropyl | H | i-Bu | H | H | H | H | 1-Naph |
| 1237 | 4-MeOC6H4CH2 | H | Me | H | H | H | H | Ph |
| 1238 | 4-MeOC6H4CH2 | H | Me | H | H | H | H | 4-ClC6H4 |
| 1239 | 4-MeOC6H4CH2 | H | Me | H | H | H | H | 4-MeC6H4 |
| 1240 | 4-MeOC6H4CH2 | H | Me | H | H | H | H | furan-2-yl |
| 1241 | 4-MeOC6H4CH2 | H | Me | H | H | H | H | pyridine-4-yl |
| 1242 | 4-MeOC6H4CH2 | H | i-Pr | H | H | H | H | Ph |
| 1243 | 4-MeOC6H4CH2 | H | i-Pr | H | H | H | H | 4-ClC6H4 |
| 1244 | 4-MeOC6H4CH2 | H | i-Pr | H | H | H | H | 3,4-Cl2C6H3 |
| 1245 | 4-MeOC6H4CH2 | H | i-Pr | H | H | H | H | 2-MeC6H4 |
| 1246 | 4-MeOC6H4CH2 | H | i-Pr | H | H | H | H | 4-MeC6H4 |
| 1247 | 4-MeOC6H4CH2 | H | i-Bu | H | H | H | H | Ph |
| 1248 | 4-MeOC6H4CH2 | H | i-Bu | H | H | H | H | 2-ClC6H4 |
| 1249 | 4-MeOC6H4CH2 | H | i-Bu | H | H | H | H | 3-ClC6H4 |
| 1250 | 4-MeOC6H4CH2 | H | i-Bu | H | H | H | H | 4-ClC6H4 |
| 1251 | 4-MeOC6H4CH2 | H | i-Bu | H | H | H | H | 2-Naph |
| 1252 | 2-(methylthio)ethyl | H | Me | H | H | H | H | Ph |

TABLE 1-continued

| Comp. No. | R17 | R18 | R19 | R20 | R21 | R22 | R23 | R24 |
|---|---|---|---|---|---|---|---|---|
| 1253 | 2-(methylthio)ethyl | H | Me | H | H | H | H | 4-ClC6H4 |
| 1254 | 2-(methylthio)ethyl | H | Me | H | H | H | H | 4-MeC6H4 |
| 1255 | 2-(methylthio)ethyl | H | Me | H | H | H | H | thiophene-2-yl |
| 1256 | 2-(methylthio)ethyl | H | Me | H | H | H | H | pyridine-2-yl |
| 1257 | 2-(methylthio)ethyl | H | i-Pr | H | H | H | H | Ph |
| 1258 | 2-(methylthio)ethyl | H | i-Pr | H | H | H | H | 4-ClC6H4 |
| 1259 | 2-(methylthio)ethyl | H | i-Pr | H | H | H | H | 3,4-Cl2C6H3 |
| 1260 | 2-(methylthio)ethyl | H | i-Pr | H | H | H | H | 2-MeC6H4 |
| 1261 | 2-(methylthio)ethyl | H | i-Pr | H | H | H | H | 4-MeC6H4 |
| 1262 | 2-(methylthio)ethyl | H | i-Bu | H | H | H | H | Ph |
| 1263 | 2-(methylthio)ethyl | H | i-Bu | H | H | H | H | 2-ClC6H4 |
| 1264 | 2-(methylthio)ethyl | H | i-Bu | H | H | H | H | 3-ClC6H4 |
| 1265 | 2-(methylthio)ethyl | H | i-Bu | H | H | H | H | 4-ClC6H4 |
| 1266 | 2-(methylthio)ethyl | H | i-Bu | H | H | H | H | 1-Naph |
| 1267 | 2-(methanesulfonyl)ethyl | H | Me | H | H | H | H | Ph |
| 1268 | 2-(methanesulfonyl)ethyl | H | Me | H | H | H | H | 4-ClC6H4 |
| 1269 | 2-(methanesulfonyl)ethyl | H | Me | H | H | H | H | 4-MeC6H4 |
| 1270 | 2-(methanesulfonyl)ethyl | H | Me | H | H | H | H | furan-2-yl |
| 1271 | 2-(methanesulfonyl)ethyl | H | Me | H | H | H | H | pyridine-4-yl |
| 1272 | 2-(methanesulfonyl)ethyl | H | i-Pr | H | H | H | H | Ph |
| 1273 | 2-(methanesulfonyl)ethyl | H | i-Pr | H | H | H | H | 4-ClC6H4 |
| 1274 | 2-(methanesulfonyl)ethyl | H | i-Pr | H | H | H | H | 3,4-Cl2C6H3 |
| 1275 | 2-(methanesulfonyl)ethyl | H | i-Pr | H | H | H | H | 2-MeC6H4 |
| 1276 | 2-(methanesulfonyl)ethyl | H | i-Pr | H | H | H | H | 4-MeC6H4 |
| 1277 | 2-(methanesulfonyl)ethyl | H | i-Bu | H | H | H | H | Ph |
| 1278 | 2-(methanesulfonyl)ethyl | H | i-Bu | H | H | H | H | 2-ClC6H4 |
| 1279 | 2-(methanesulfonyl)ethyl | H | i-Bu | H | H | H | H | 3-ClC6H4 |
| 1280 | 2-(methanesulfonyl)ethyl | H | i-Bu | H | H | H | H | 4-ClC6H4 |
| 1281 | 2-(methanesulfonyl)ethyl | H | i-Bu | H | H | H | H | 2-Naph |
| 1282 | 2-thienyl | H | Me | H | H | H | H | Ph |
| 1283 | 2-thienyl | H | Me | H | H | H | H | 4-ClC6H4 |
| 1284 | 2-thienyl | H | Me | H | H | H | H | 4-MeC6H4 |
| 1285 | 2-thienyl | H | Me | H | H | H | H | thiophene-2-yl |
| 1286 | 2-thienyl | H | Me | H | H | H | H | pyridine-2-yl |
| 1287 | 2-thienyl | H | i-Pr | H | H | H | H | Ph |
| 1288 | 2-thienyl | H | i-Pr | H | H | H | H | 4-ClC6H4 |
| 1289 | 2-thienyl | H | i-Pr | H | H | H | H | 3,4-Cl2C6H3 |
| 1290 | 2-thienyl | H | i-Pr | H | H | H | H | 2-MeC6H4 |
| 1291 | 2-thienyl | H | i-Pr | H | H | H | H | 4-MeC6H4 |
| 1292 | 2-thienyl | H | i-Bu | H | H | H | H | Ph |
| 1293 | 2-thienyl | H | i-Bu | H | H | H | H | 2-ClC6H4 |
| 1294 | 2-thienyl | H | i-Bu | H | H | H | H | 3-ClC6H4 |
| 1295 | 2-thienyl | H | i-Bu | H | H | H | H | 4-ClC6H4 |
| 1296 | 2-thienyl | H | i-Bu | H | H | H | H | 1-Naph |

TABLE 2

Analytical data

| Comp. No. | Analytical data |
|---|---|
| 4 | $^1$H NMR(CDCl$_3$, ppm): 1.15(3H, d, J = 6.1 Hz), 3.46–3.61(2H, m), 3.63(3H, s), 3.66–3.72(1H, m), 4.86(1H, d, J = 8.5 Hz), 6.86(1H, br-s), 7.41(2H, d, J = 8.1 Hz), 7.74(2H, d, J = 8.1 Hz). |
| 26 | $^1$H NMR(CDCl$_3$, ppm): 1.00(6H, t, J = 8.1 Hz), 1.85–1.89(1H, m), 3.46–3.61(2H, m), 3.63(3H, s), 3.66–3.72(1H, m), 4.86(1H, d, J = 8.5 Hz), 6.86(1H, br-s), 7.39–7.49 (3H, m), 7.79(2H, d, J = 7.1 Hz). |
| 30 | $^1$H NMR(CDCl$_3$, ppm): 1.00(6H, t, J = 8.1 Hz), 1.85–1.89(1H, m), 2.39(3H, s), 3.46–3.61(2H, m), 3.63(3H, s), 3.66–3.72(1H, m), 4.86(1H, d, J = 8.5 Hz), 6.86(1H, br-s), 7.23(2H, d, J = 8.1 Hz), 7.68(2H, d, J = 8.1 Hz). |
| 66 | $^1$H NMR(CDCl$_3$, ppm): 3.46–3.61(2H, m), 3.63(3H, s), 3.66–3.72(1H, m), 4.86(1H, d, J = 8.5 Hz), 6.86(1H, br-s), 7.23–7.41(5H, m), 7.39–7.49(3H, m), 7.79 1(2H, d, J = 7.1 Hz). |
| 215 | $^1$H NMR(CDCl$_3$, ppm): 1.14(3H, d, J = 6.1 Hz), 1.22(3H, d, J = 6.8 Hz), 1.24(3H, d, J = 6.8 Hz), 2.39(3H, s), 3.48–3.53(2H, m), 3.96–3.99(1H, m), 4.79(1H, br-s), 4.84–4.91(1H, m), 7.23(2H, d, J = 8.1 Hz), 7.70(2H, d, J = 8.1 Hz). |
| 216 | $^1$H NMR(CDCl$_3$, ppm): 1.14(3H, d, J = 6.1 Hz), 1.22(3H, d, J = 6.8 Hz), 1.24(3H, d, J = 6.8 Hz), 1.32(9H, s), 3.48–3.53(2H, m), 3.96–3.99(1H, m), 4.79(1H, br-s), 4.84–4.91(1H, m), 7.23(2H, d, J = 8.1 Hz), 7.70(2H, d, J = 8.1 Hz). |
| 236 | $^1$H NMR(CDCl$_3$, ppm): 1.01(6H, t, J = 7.1 Hz), 1.09(3H, d, J = 6.1 Hz), 1.22(3H, d, J = 6.1 Hz), 1.85–1.89(1H, m), 3.48–3.61(2H, m), 3.68–3.74(1H, m), 4.12(1H, d, J = 7.3 Hz), 4.73–4.89(1H, m), 7.06(1H, br-s), 7.40–7.50(3H, m), 7.80(2H, d, J = 7.1 Hz). |

TABLE 2-continued

Analytical data

| Comp. No. | Analytical data |
|---|---|
| 237 | ¹H NMR(CDCl₃, ppm): 1.00(3H, d, J = 6.8 Hz), 1.01(3H, d, J = 6.8 Hz), 1.11(3H, d, J = 6.1 Hz), 1.23(3H, d, J = 6.1 Hz), 1.85–1.90(1H, m), 3.50–3.54(2H, m), 3.67–3.73 (1H, m), 4.73(1H, d, J = 8.8 Hz), 4.83–4.90(1H, m), 7.21(1H, br-s), 7.40(2H, d, J = 8.5 Hz), 7.75(2H, d, J = 8.5 Hz). |
| 238 | ¹H NMR(CDCl₃, ppm): 1.01(6H, t, J = 6.8 Hz), 1.14(3H, d, J = 6.3 Hz), 1.24(3H, d, J = 6.3 Hz), 1.85–1.90(1H, m), 3.50–3.53(2H, m), 3.67–3.72(1H, m), 4.75(1H, d, J = 8.3 Hz), 4.86–4.92(1H, m), 7.35(1H, br-s), 7.50(1H, d, J = 8.3 Hz), 7.62(1H, d, J = 8.3 Hz), 7.94(1H, s). |
| 239 | ¹H NMR(CDCl₃, ppm): 0.98(3H, d, J = 6.8 Hz), 1.00(3H, d, J = 6.8 Hz), 1.17(3H, d, J = 6.3 Hz), 1.21(3H, d, J = 6.3 Hz), 1.83–1.88(1H, m), 2.44(3H, s), 3.41–3.47(1H, m), 3.56–3.70(2H, m), 4.77(1H, d, J = 8.5 Hz), 4.82–4.88(1H, m), 6.29(1H br-s), 7.16–7.35(4H, m). |
| 240 | ¹H NMR(CDCl₃, ppm): 0.99(3H, d, J = 7.3 Hz), 1.01(3H, d, J = 7.3 Hz), 1.10(3H, d, J = 6.1 Hz), 1.21(3H, d, J = 6.1 Hz), 1.84–1.88(1H, m), 2.38(3H, s), 3.47–3.60(2H, m), 3.67–3.73(1H, m), 4.75(1H, d, J = 8.5 Hz), 4.83–4.89(1H, m), 6.99(1H, br-s), 7.22 (2H, d, J = 8.1 Hz), 7.69(2H, d, J = 8.1 Hz). |
| 241 | ¹H NMR(CDCl₃, ppm): 1.00(6H, t, J = 7.3 Hz), 1.09(3H, d, J = 6.2 Hz), 1.21–1.26(6H, m), 1.82–1.90(1H, m), 2.68(2H, q, J = 7.6 Hz), 3.46–3.62(2H, m), 3.68–3.76(1H, m), 4.74(1H, d, J = 8.8 Hz), 4.87–4.90(1H, m), 6.99(1H, d, J = 8.1 Hz), 7.24(2H, d, J = 8.5 Hz), 7.72(2H, d, J = 8.5 Hz). |
| 242 | ¹H NMR(CDCl₃, ppm): 1.03(6H, t, J = 6.8 Hz), 1.09(3H, d, J = 6.1 Hz), 1.22(3H, d, J = 6.1 Hz), 1.87–1.92(1H, m), 3.54–3.67(2H, m), 3.74–3.78(1H, m), 4.77(1H, d, J = 8.5 Hz), 4.86–4.92(1H, m), 7.23(1H, br-s), 7.51–7.58(2H, m), 7.86–7.94(4H, m), 8.34(1H, s). |
| 243 | ¹H NMR(CDCl₃, ppm): 0.97–1.00(6H, m), 1.11(3H, d, J = 6.3 Hz), 1.22(3H, d, J = 6.3 Hz), 1.80–1.90(1H, m), 2.50(3H, s), 3.44–3.57(2H, m), 3.66–3.73(1H, m), 4.76(1H, d, J = 8.5 Hz), 4.87–4.90(1H, m), 6.71(1H, d, J = 3.7 Hz), 6.87(1H, br-s), 7.30(1H, d, J = 3.7 Hz) |
| 245 | ¹H NMR(CDCl₃, ppm): 0.93(3H, d, J = 7.1 Hz), 0.95(3H, d, J = 7.1 Hz), 1.15(3H, s), 1.23(6H, d, J = 6.3 Hz), 2.35–2.40(4H, m), 3.60(1H, dd, J = 5.1 Hz, 14.2 Hz), 3.82 (1H, dd, J = 5.9 Hz, 14.2 Hz), 4.72(1H, br-s), 4.87–4.93(1H, m), 7.24(2H, d, J = 8.1 Hz), 7.76(2H, d, J = 8.1 Hz). |
| 246 | ¹H NMR(CDCl₃, ppm): 1.00–1.03(6H, m), 1.17(3H, d, J = 6.6 Hz), 1.26(6H, d, J = 6.3 Hz), 1.65–1.69(1H, m), 2.39(3H, s), 3.51–3.56(1H, m), 4.33–4.37(1H, m), 4.56(1H, d, J = 8.0 Hz), 4.92–5.00(1H, m), 7.23(2H, d, J = 8.3 Hz), 7.30(1H, br-s), 7.72(2H, d, J = 8.3 Hz). |
| 247 | ¹H NMR(CDCl₃, ppm): 0.99–1.03(6H, m), 1.18(3H, d, J = 6.6 Hz), 1.26(6H, d, J = 6.3 Hz), 1.62–1.67(1H, m), 3.50–3.54(1H, m), 4.33–4.35(1H, m), 4.53(1H, d, J = 8.0 Hz), 4.91–4.98(1H, m), 7.22(2H, d, J = 8.3 Hz), 7.31(1H, br-s), 7.74(2H, d, J = 8.3 Hz). |
| 279 | ¹H NMR(CDCl₃, ppm): 1.15–1.26(6H, m), 2.40(3H, s), 3.25–3.30(1H, m), 3.42–3.50 (1H, m), 4.82–4.90(1H, m), 4.92–4.98(1H, m), 5.60(1H, d, J = 7.1 Hz), 6.84(1H, br-s), 7.22–7.40(7H, m), 7.67(2H, d, J = 7.8 Hz). |
| 284 | ¹H NMR(CDCl₃, ppm): 1.13–1.19(6H, m), 2.40(3H, m), 3.70–3.80(2H, m), 4.82–4.92 (2H, m), 5.80(1H, d, J = 7.1 Hz), 6.65(1H, br-s), 7.21–7.29(4H, m), 7.34(2H, d, J = 8.1 Hz), 7.65(2H, d, J = 8.1 Hz).<br>M⁺: 375. |
| 289 | ¹H NMR(CDCl₃, ppm): 1.12(3H, d, J = 6.1 Hz), 1.18(3H, d, J = 6.1 Hz), 2.38(3H, s), 2.80–2.86(1H, m), 2.92–2.98(1H, m), 3.49–3.56(2H, m), 4.07–4.15(1H, m), 4.81–4.88(1H, m), 4.95(1H, d, J = 7.3 Hz), 6.88(1H, br-s), 7.20–7.27(5H, m), 7.31 (2H, d, J = 8.1 Hz), 7.65(2H, d, J = 8.1 Hz). |
| 290 | ¹H NMR(CDCl₃, ppm): 1.12(3H, d, J = 6.1 Hz), 1.18(3H, d, J = 6.1 Hz), 1.20–1.25(3H, m), 2.67(2H, q, J = 7.6 Hz), 2.80–2.86(1H, m), 2.92–2.98(1H, m), 3.49–3.56(2H, m), 4.07–4.15(1H, m), 4.81–4.88(1H, m), 4.95(1H, d, J = 7.3 Hz), 6.88(1H, br-s), 7.20–7.27(5H, m), 7.31(2H, d, J = 8.1 Hz), 7.65(2H, d, J = 8.1 Hz). |
| 384 | ¹H NMR(CDCl₃, ppm): 0.85(3H, d, J = 6.6 Hz), 0.86(3H, d, J = 6.6 Hz), 1.01(6H, t, J = 6.6 Hz), 1.79–1.89(1H, m), 3.47–3.71(3H, m), 3.80(2H, d, J = 6.8 Hz), 4.82(1H, d, J = 8.3 Hz), 6.92(br-s), 7.41(2H, d, J = 8.3 Hz), 7.76(2H, d, J = 8.3 Hz). |
| 387 | ¹H NMR(CDCl₃, ppm): 0.84(3H, d, J = 6.8 Hz), 0.85(3H, d, J = 6.8 Hz), 1.06(6H, d, J = 6.8 Hz), 1.63–1.89(2H, m), 2.39(3H, s), 3.46–3.74(3H, m), 3.80(2H, d, J = 6.6 Hz), 4.82(1H, d, J = 8.8 Hz), 6.92(1H, br-s), 7.22(2H, d, J = 7.8 Hz), 7.68(2H, d, J = 7.8 Hz). |
| 464 | ¹H NMR(CDCl₃, ppm): 1.00(6H, t, J = 6.8 Hz), 1.39(9H, s), 1.82–1.87(1H, m), 2.38 (3H, s), 3.46–3.53(2H, m), 3.65–3.69(1H, m), 4.65(1H, d, J = 8.5 Hz), 7.04(1H, br-s), 7.21(2H, d, J = 8.1 Hz), 7.70(2H, d, J = 8.1 Hz). |
| 469 | ¹H NMR(CDCl₃, ppm): 0.92(3H, d, J = 6.8 Hz), 0.94(3H, d, J = 6.8 Hz), 1.13(3H, s), 2.37–2.41(4H, m), 3.57(1H, dd, J = 5.6 Hz), 13.7 Hz), 3.81(1H, dd, J = 5.6 Hz), 13.7 Hz), 4.62(1H, br-s), 7.24(2H, d, J = 8.1 Hz), 7.77(2H, d, J = 8.1 Hz), 8.17(1H, br-s). |
| 470 | ¹H NMR(CDCl₃, ppm): 1.00–1.03(6H, m), 1.17(3H, d, J = 6.6 Hz), 1.49(9H, s), 1.58–1.67(1H, m), 3.47–3.53(1H, m), 4.33–4.35(1H, m), 4.51(1H, d,, J = 8.0 Hz), 7.23(2H, d, J = 8.3 Hz), 7.38(1H, br-s), 7.73(2H, d, J = 8.3 Hz). |
| 471 | ¹H NMR(CDCl₃, ppm): 1.00–1.03(6H, m), 1.16(3H, d, J = 6.6 Hz), 1.49(9H, s), 1.59–1.68(1H, m), 2.38(3H, s), 3.46–3.52(1H, m), 4.33–4.35(1H, m), 4.51(1H, d, J = 8.0 Hz), 7.21(2H, d, J = 8.3 Hz), 7.36(1H, br-s), 7.72(2H, d, J = 8.3 Hz). |

TABLE 2-continued

Analytical data

| Comp. No. | Analytical data |
|---|---|
| 504 | $^1$H NMR(CDCl$_3$, ppm): 1.40(9H, s), 2.40(3H, s), 3.25–3.30(1H, m), 3.42–3.50(1H, m), 4.82–4.90(1H, m), 5.60(1H, d, J = 7.1 Hz), 6.84(1H, br-s), 7.22–7.40(7H, m), 7.67(2H, d, J = 7.8 Hz). |
| 526 | $^1$H NMR(CDCl$_3$, ppm): 1.05(3H, d, J = 6.8 Hz), 1.07(3H, d, J = 6.8 Hz), 1.91–1.96 (1H, m), 2.40(3H, s), 3.47–3.50(1H, m), 3.74–3.78(2H, m), 5.26(1H, d, J = 7.6 Hz), 6.76(1H, br-s), 7.15–7.31(5H, m), 7.40–7.50(3H, m), 7.80(2H, d, J = 7.3 Hz). |
| 530 | $^1$H NMR(CDCl$_3$, ppm): 1.05(3H, d, J = 6.8 Hz), 1.07(3H, d, J = 6.8 Hz), 1.91–1.96 (1H, m), 2.40(3H, s), 3.47–3.50(1H, m), 3.74–3.78(2H, m), 5.26(1H, d, J = 7.6 Hz), 6.76(1H, br-s), 6.95(2H, d, J = 8.3 Hz), 7.15–7.31(5H, m), 7.68(2H, d, J = 8.3 Hz). |
| 596 | $^1$H NMR(CDCl$_3$, ppm): 0.99(3H, d, J = 6.8 Hz), 1.01(3H, d, J = 6.8 Hz), 1.85–1.90 (1H, m), 2.39(3H, s), 3.48–3.62(2H, m), 3.69–3.74(1H, m), 4.94(1H, d, J = 8.8 Hz), 5.06(2H, d, J = 7.1 Hz), 6.86(1H, br-s), 7.20–7.30(7H, m), 7.41–7.51(3H, m), 7.79(2H, d, J = 7.1 Hz). |
| 600 | $^1$H NMR(CDCl$_3$, ppm): 0.99(3H, d, J = 6.8 Hz), 1.01(3H, d, J = 6.8 Hz), 1.85–1.90 (1H, m), 2.39(3H, s), 3.48–3.62(2H, m), 3.69–3.74(1H, m), 4.94(1H, d, J = 8.8 Hz), 5.06(2H, d, J = 7.1 Hz), 6.86(1H, br-s), 7.20–7.30(7H, m), 7.65(2H, d, J = 8.1 Hz). |
| 636 | $^1$H NMR(CDCl$_3$, ppm): 3.48–3.62(2H, m), 3.69–3.74(1H, m), 4.94(1H, d, J = 8.8 Hz), 5.06(2H, d, J = 7.1 Hz), 6.86(1H, br-s), 7.20–7.40(14H, m), 7.82(2H, d, J = 7.1 Hz). |
| 674 | $^1$H NMR(CDCl$_3$, ppm): 1.10(3H, d, J = 6.8 Hz), 1.12(3H, d, J = 6.8 Hz), 1.94–2.01 (1H, m), 3.50–3.55(1H, m), 3.80–3.84(2H, m), 5.31(1H, d, J = 8.5 Hz), 6.78(1H, br-s), 7.10(1H, d, J = 8.8 Hz), 7.21(2H, d, J = 7.8 Hz), 7.37(1H, s), 7.41–7.56(2H, m), 7.60–7.90(5H, m). |
| 677 | $^1$H NMR(CDCl$_3$, ppm): 1.09(3H, d, J = 6.8 Hz), 1.10(3H, d, J = 6.8 Hz), 1.94–1.99 (1H, m), 2.40(3H, s), 3.47–3.51(1H, m), 3.80–3.84(2H, m), 5.30(1H, d, J = 8.5 Hz), 6.77(1H, br-s), 7.10(1H, d, J = 8.8 Hz), 7.21(2H, d, J = 7.8 Hz), 7.34(1H, s), 7.41–7.54(2H, m), 7.63–7.93(5H, m). |
| 739 | $^1$H NMR(CDCl$_3$, ppm): 1.00(6H, t, J = 7.3 Hz), 1.85–1.90(1H, m), 3.46–3.74(3H, m), 4.52(2H, d, J = 5.6 Hz), 4.93(1H, d, J = 8.3 Hz), 5.14(1H, d, J = 10.5 Hz), 5.25 (1H, d, J = 17.1 Hz), 4.79–5.88(1H, m), 6.88(1H, br-s), 7.39(2H, d, J = 8.1 Hz), 7.73(2H, d, J = 8.1 Hz). |
| 742 | $^1$H NMR(CDCl$_3$, ppm): 1.00(6H, t, J = 7.3 Hz), 1.85–1.90(1H, m), 2.39(3H, s), 3.46–3.74(3H, m), 4.52(2H, d, J = 5.6 Hz), 4.93(1H, d, J = 8.3 Hz), 5.14(1H, d, J = 10.5 Hz), 5.25(1H, d, J = 17.1 Hz), 4.79–5.88(1H, m), 6.88(1H, br-s), 7.22(2H, d, J = 8.1 Hz), 7.68(2H, d, J = 8.1 Hz). |
| 804 | $^1$H NMR(CDCl$_3$, ppm): 1.00(6H, t, J = 7.8 Hz), 1.86–1.91(1H, m), 2.36(1H, s), 3.47–3.74(3H, m), 4.63(2H, s), 5.01(1H, d, J = 9.0 Hz), 6.79(1H, br-s), 7.38(2H, d, J = 8.1 Hz), 7.73(2H, d, J = 8.1 Hz). |
| 807 | $^1$H NMR(CDCl$_3$, ppm): 1.00(6H, t, J = 7.8 Hz), 1.86–1.91(1H, m), 2.36(1H, s), 2.39 (3H, s), 3.47–3.74(3H, m), 4.63(2H, s), 5.01(1H, d, J = 9.0 Hz), 6.79(1H, br-s), 7.22 (2H, d, J = 8.1 Hz), 7.68(2H, d, J = 8.1 Hz). |
| 1049 | $^1$H NMR(CDCl$_3$, ppm): 0.98(3H, d, J = 7.1 Hz), 1.00(3H, d, J = 7.1 Hz), 1.84–1.89(1H, m), 2.31(3H, s), 3.49–3.57(2H, m), 3.69–3.75(1H, m), 4.92(1H, d, J = 9.0 Hz), 5.00 (1H, d, J = 12.2 Hz), 5.05(1H, d, J = 12.2 Hz), 7.00(1H, br-s), 7.07(2H, d, J = 8.1 Hz), 7.16(2H, d, J = 7.8 Hz), 7.24(2H, d, J = 8.1 Hz), 7.67(2H, d, J = 7.8 Hz). |
| 1050 | $^1$H NMR(CDCl$_3$, ppm): 0.98(3H, d, J = 7.1 Hz), 1.00(3H, d, J = 7.1 Hz), 1.84–1.89(1H, m), 2.31(3H, s), 2.40(3H, s), 3.49–3.57(2H, m), 3.69–3.75(1H, m), 4.92(1H, d, J = 9.0 Hz), 5.00(1H, d, J = 12.2 Hz), 5.05(1H, d, J = 12.2 Hz), 7.00(1H, br-s), 7.07 (2H, d, J = 8.1 Hz), 7.16(2H, d, J = 7.8 Hz), 7.22(2H, d, J = 8.1 Hz), 7.65(2H, d, J = 7.8 Hz). |
| 1063 | $^1$H NMR(CDCl$_3$, ppm): 1.00(6H, t, J = 7.1 Hz), 1.83–1.90(1H, m), 3.43–3.47(1H, m), 3.62–3.73(2H, m), 4.94(1H, d, J = 12.4 Hz), 4.95(1H, d, J = 9.0 Hz), 5.06(1H, d, J = 12.4 Hz), 6.73(1H, br-s), 7.17–7.22(6H, m), 7.59(2H, d, J = 8.1 Hz). |
| 1066 | $^1$H NMR(CDCl$_3$, ppm): 1.00(6H, t, J = 7.1 Hz), 1.83–1.90(1H, m), 2.41(3H, s), 3.43–3.47(1H, m), 3.62–3.73(2H, m), 4.94(1H, d, J = 12.4 Hz), 4.95(1H, d, J = 9.0 Hz), 5.06(1H, d, J = 12.4 Hz), 6.73(1H, br-s), 7.17–7.22(6H, m), 7.61(2H, d, J = 8.1 Hz). |
| 1078 | $^1$H NMR(CDCl$_3$, ppm): 0.95–1.02(6H, m), 1.39(3 × 1/2H, d, J = 6.6 Hz), 1.51(3H × 1/2, d, J = 6.6 Hz), 1.80–1.88(1H, m), 3.40–3.64(3H, m), 4.90(1H × 1/2, d, J = 8.5 Hz), 4.96(1H × 1/2, d, J = 9.0 Hz), 5.70–5.77(1H, m), 6.71(1H × 1/2, br-s), 6.78(1H × 1/2, br-s), 7.09–7.36(6H, m), 7.45(2H × 1/2, d, J = 8.3 Hz), 7.69(2H × 1/2, d, J = 8.3 Hz). |
| 1081 | $^1$H NMR(CDCl$_3$, ppm): 0.95–1.02(6H, m), 1.39(3H × 1/2, d, J = 6.6 Hz), 1.51(3H × 1/2, d, J = 6.6 Hz), 1.80–1.88(1H, m), 2.37(3H × 1/2, s), 2.40(3H × 1/2, s), 3.40–3.64(3H, m), 4.90(1H × 1/2, d, J = 8.5 Hz), 4.96(1H × 1/2, d, J = 9.0 Hz), 5.70–5.77(1H, m), 6.71(1H × 1/2, br-s), 6.78(1H × 1/2, br-s), 7.09–7.36(6H, m), 7.47(2H × 1/2, d, J = 8.3 Hz), 7.71(2H × 1/2, d, J = 8.3 Hz). |
| 1123 | $^1$H NMR(CDCl$_3$, ppm): 0.99(3H, d, J = 6.8 Hz), 1.02(3H, d, J = 6.8 Hz), 1.85–1.89(1H, m), 3.51–3.54(2H, m), 3.72–3.76(1H, m), 4.90(1H, d, J = 9.0 Hz), 5.02(2H, d, J = 4.9 Hz), 6.29(1H, d, J = 3.2 Hz), 6.31(1H, d, J = 3.2 Hz), 6.85(1H, br-s), 7.20(2H, d, J = 8.1 Hz), 7.33(1H, s), 7.66(2H, d, J = 8.1 Hz). |
| 1126 | $^1$H NMR(CDCl$_3$, ppm): 0.98(3H, d, J = 6.8 Hz), 1.00(3H, d, J = 6.8 Hz), 1.85–1.89(1H, m), 2.40(3H, s), 3.51–3.54(2H, m), 3.70–3.76(1H, m), 4.90(1H, d, J = 9.0 Hz), 5.02 (2H, d, J = 4.9 Hz), 6.29(1H, d, J = 3.2 Hz), 6.33(1H, d, J = 3.2 Hz), 6.87(1H, br-s), 7.23(2H, d, J = 8.1 Hz), 7.33(1H, s), 7.68(2H, d, J = 8.1 Hz). |

TABLE 2-continued

Analytical data

| Comp. No. | Analytical data |
|---|---|
| 1138 | $^1$H NMR(CDCl$_3$, ppm): 0.98(3H, d, J = 6.8 Hz), 1.00(3H, d, J = 6.8 Hz), 1.84–1.89(1H, m), 3.48–3.61(2H, m), 3.68–3.73(1H, m), 4.88(1H, d, J = 6.8 Hz), 4.92(2H, s), 6.34 (1H, s), 6.80(1H, br-s), 7.20(2H, d, J = 7.8 Hz), 7.29(1H, d, J = 2.0 Hz), 7.41(1H, d, J = 2.0 Hz), 7.63(2H, d, J = 7.8 Hz). |
| 1141 | $^1$H NMR(CDCl$_3$, ppm): 0.98(3H, d, J = 6.8 Hz), 1.00(3H, d, J = 6.8 Hz), 1.84–1.89(1H, m), 2.40(3H, s), 3.48–3.61(2H, m), 3.68–3.73(1H, m), 4.88(1H, d, J = 6.8 Hz), 4.92 (2H, s), 6.33(1H, s), 6.83(1H, br-s), 7.22(2H, d, J = 7.8 Hz), 7.31(1H, d, J = 2.0 Hz), 7.39(1H, d, J = 2.0 Hz), 7.65(2H, d, J = 7.8 Hz). |
| 1153 | $^1$H NMR(CDCl$_3$, ppm): 1.00(3H, d, J = 6.8 Hz), 1.01(3H, d, J = 6.8 Hz), 1.49–1.56(1H, m), 1.81–1.95(4H, m), 3.51–3.54(2H, m), 3.65–4.16(6H, m), 4.95(1H, d, J = 8.5 Hz), 6.91(1H, br-s), 7.24(2H, d, J = 8.1 Hz), 7.70(2H, d, J = 8.1 Hz). |
| 1156 | $^1$H NMR(CDCl$_3$, ppm): 0.99(3H, d, J = 6.8 Hz), 1.01(3H, d, J = 6.8 Hz), 1.49–1.56(1H, m), 1.81–1.95(4H, m), 2.39(3H, s), 3.51–3.55(2H, m), 3.67–4.16(6H, m), 4.95(1H, d, J = 8.5 Hz), 6.93(1H, br-s), 7.22(2H, d, J = 8.1 Hz), 7.68 (2H, d, J = 8.1 Hz). |
| 1168 | $^1$H NMR(CDCl$_3$, ppm): 0.98(3H, d, J = 6.8 Hz), 1.00(3H, d, J = 6.8 Hz), 1.85–1.89(1H, m), 3.51–3.56(2H, m), 3.70–3.75(1H, m), 4.91(1H, d, J = 8.8 Hz), 5.19(1H, d, J = 12.7 Hz), 5.22(1H, d, J = 12.7 Hz), 6.83(1H, br-s), 6.91(1H, dd, J = 1.7 Hz, 3.4 Hz), 7.01 (1H, dd, J = 1.7 Hz, 3.4 Hz), 7.21–7.25(3H, m), 7.68(2H, d, J = 8.1 Hz). |
| 1171 | $^1$H NMR(CDCl$_3$, ppm): 0.98(3H, d, J = 6.8 Hz), 1.00(3H, d, J = 6.8 Hz), 1.85–1.89 (1H, m), 2.40(3H, s), 3.51–3.56(2H, m), 3.70–3.75(1H, m), 4.92(1H, d, J = 8.8 Hz), 5.19(1H, d, J = 12.7 Hz), 5.22(1H, d, J = 12.7 Hz), 6.85(1H, br-s), 6.91(1H, dd, J = 1.7 Hz, 3.4 Hz), 7.01(1H, dd, J = 1.7 Hz, 3.4 Hz), 7.21–7.24(3H, m), 7.66 (2H, d, J = 8.1 Hz). |
| 1183 | $^1$H NMR(CDCl$_3$, ppm): 0.19–0.23(2H, m), 0.45–0.50(2H, m), 1.01(6H, t, J = 7.1 Hz), 1.86–1.93(1H, m), 3.48–3.64(2H, m), 3.67–3.75(1H, m), 3.85(2H, d, J = 7.3 Hz), 4.87(1H, d, J = 9.0 Hz), 6.96(1H, br-s), 7.23(2H, d, J = 8.5 Hz), 7.69(2H, d, J = 8.5 Hz). |
| 1186 | $^1$H NMR(CDCl$_3$, ppm): 0.19–0.23(2H, m), 0.45–0.49(2H, m), 1.01(6H, t, J = 7.1 Hz), 1.86–1.93(1H, m), 2.38(3H, s), 3.48–3.62(2H, m), 3.67–3.75(1H, m), 3.84 (2H, d, J = 7.3 Hz), 4.86(1H, d, J = 9.0 Hz), 6.96(1H, br-s), 7.21(2H, d, J = 8.5 Hz), 7.68(2H, d, J = 8.5 Hz). |
| 1198 | $^1$H NMR(CDCl$_3$, ppm): 0.86(9H, s), 1.03(6H, t, J = 5.6 Hz), 1.86–1.90(1H, m), 3.48–3.68(2H, m), 3.70–3.75(3H, m), 4.84(1H, d, J = 8.5 Hz), 6.92(1H, d, J = 6.6 Hz), 7.20(2H, d, J = 8.1 Hz), 7.65(2H, d, J = 8.1 Hz). |
| 1201 | $^1$H NMR(CDCl$_3$, ppm): 0.86(9H, s), 1.01(6H, t, J = 5.6 Hz), 1.86–1.91(1H, m), 2.39(3H, s), 3.48–3.68(2H, m), 3.70–3.76(3H, m), 4.84(1H, d, J = 8.5 Hz), 6.94 (1H, d, J = 6.6 Hz), 7.22(2H, d, J = 8.1 Hz), 7.67(2H, d, J = 8.1 Hz). |
| 1213 | $^1$H NMR(CDCl$_3$, ppm): 1.03(6H, t, J = 7.1 Hz), 1.68(3H, s), 1.84–1.90(1H, m), 3.46–3.75(3H, m), 4.45(2H, s), 4.83(1H, s), 4.90–4.95(2H, m), 6.87(1H, br-s), 7.22(2H, d, J = 8.1 Hz), 7.68(2H, d, J = 8.1 Hz). |
| 1216 | $^1$H NMR(CDCl$_3$, ppm): 1.01(6H, t, J = 7.1 Hz), 1.67(3H, s), 1.84–1.90(1H, m), 2.39(3H, s), 3.46–3.75(3H, m), 4.44(2H, s), 4.83(1H, s), 4.90–4.94(2H, m), 6.87 (1H, br-s), 7.21(2H, d, J = 8.1 Hz), 7.67(2H, d, J = 8.1 Hz). |
| 1228 | $^1$H NMR(CDCl$_3$, ppm): 0.75(3H, d, J = 6.6 Hz), 0.90(3H, d, J = 6.6 Hz), 1.01(6H + 3H × 1/2, t, J = 6.6 Hz), 1.13(3H × 1/2, d, J = 6.6 Hz), 1.82–1.91(1H, m), 3.45–3.65 (2H, m), 3.69–3.77(1H, m), 4.56–4.61(1H, m), 4.75(1H, t, J = 8.1 Hz), 6.94(1H, d, J = 9.0 Hz), 7.20–7.24(2H, m), 7.66(2H, t, J = 7.6 Hz). |
| 1231 | $^1$H NMR(CDCl$_3$, ppm): 0.75(3H, d, J = 6.6 Hz), 0.89(3H, d, J = 6.6 Hz), 1.01(6H + 3H × 1/2, t, J = 6.6 Hz), 1.14(3H × 1/2, d, J = 6.6 Hz), 1.82–1.91(1H, m), 2.38(3H, s), 3.45–3.65(2H, m), 3.69–3.76(1H, m), 4.56–4.62(1H, m), 4.75(1H, t, J = 8.1 Hz), 6.95(1H, d, J = 9.0 Hz), 7.20–7.23(2H, m), 7.68(2H, t, J = 7.6 Hz). |
| 1258 | $^1$H NMR(CDCl$_3$, ppm): 1.00(6H, t, J = 7.6 Hz), 1.86–1.92(1H, m), 2.05(3H, s), 2.62(2H, t, J = 6.8 Hz), 3.47–3.73(3H, m), 4.15–4.24(2H, m), 4.89(1H, d, J = 8.5 Hz), 6.84(1H, br-s), 7.22(2H, d, J = 8.1 Hz), 7.67(2H, d, J = 8.1 Hz). |
| 1261 | $^1$H NMR(CDCl$_3$, ppm): 1.00(6H, t, J = 7.6 Hz), 1.86–1.91(1H, m), 2.07(3H, s), 2.39(3H, s), 2.62(2H, t, J = 6.8 Hz), 3.47–3.72(3H, m), 4.15–4.23(2H, m), 4.89 (1H, d, J = 8.5 Hz), 6.81(1H, br-s), 7.23(2H, d, J = 8.1 Hz), 7.68(2H, d, J = 8.1 Hz). |
| 1273 | $^1$H NMR(CDCl$_3$, ppm): 0.98(3H, d, J = 6.8 Hz), 1.02(3H, d, J = 6.8 Hz), 1.83–1.90 (1H, m), 2.40(3H, s), 3.13–3.18(2H, m), 3.41–3.45(1H, m), 3.66–3.70(2H, m), 4.34–4.40(1H, m), 4.49–4.54(1H, m), 5.20(1H, d, J = 8.1 Hz), 6.64(1H, br-s), 7.26 (2H, d, J = 7.8 Hz), 7.65(2H, d, J = 7.8 Hz). |
| 1276 | $^1$H NMR(CDCl$_3$, ppm): 0.99(3H, d, J = 6.8 Hz), 1.01(3H, d, J = 6.8 Hz), 1.83–1.90 (1H, m), 2.40(3H, s), 2.81(3H, s), 3.13–3.16(2H, m), 3.41–3.45(1H, m), 3.66–3.70(2H, m), 4.34–4.40(1H, m), 4.49–4.55(1H, m), 5.19(1H, d, J = 8.1 Hz), 6.66(1H, br-s), 7.24(2H, d, J = 7.8 Hz), 7.66(2H, d, J = 7.8 Hz). |

Examples of Formulations and Tests

The examples of the formulations and the activity tests of the fungicides according to the invention will be shown below. In the following examples, the term "part" hereinafter used means "part by weight" or "% by weight".

Example of Formulation 1 Granules

Thirty parts of the compound of the invention (30), 22 parts of bentonite, 45 parts of talc, 3 parts of Sorpol 5060 (surfactant: Toho Chemical Industry Co., Ltd., brand name) and a small quantity of antifoamer were kneaded uniformly, granulated with a basket granulating machine, and dried to obtain 100 parts of granules.

Example of Formulation 2 Granules

Fifteen parts of the compound of the invention (241), 60 parts of bentonite, 21 parts of talc, 1 part of sodium dodecylbenzenesulfonate, 1 part of polyoxyethylenealkyl allyl ether and 2 parts of sodium ligninsulfonate were mixed, kneaded uniformly with the addition of a suitable quantity of water, granulated with a basket granulating machine, and dried to obtain 100 parts of granules.

Example of Formulation 3: Wettable Powder

Fifty parts of the compound of the invention (290), 40 parts of calcium carbonate, 5 parts of Sorpol 5039 (a mixture of anionic surfactant and white carbon: Toho Chemical Industry Co., Ltd., brand name) and 5 parts of white carbon were mixed and milled uniformly to obtain a wettable powder.

Example of Formulation 4 Wettable Powder

Thirty parts of the compound of the invention (526), 63 parts of kaolinite, 5 parts of Sorpol 5039 (a mixture of anionic surfactant and white carbon: Toho Chemical Industry Co., Ltd., brand name) and 2 parts of white carbon were mixed and milled uniformly to obtain wettable powder.

Example of Formulation 5 Emulsion

Twenty parts of the compound of the invention (674), 55 parts of xylene, 20 parts of N,N-dimethylformamide and 5 parts of Sorpol 2680 (surfactant) were mixed uniformly to obtain an emulsion concentrate.

Example of Formulation 6 Flowable

Of all the ingredients of 40 parts of the compound of the invention (742), 5 parts of Sorpol 3353 (a nonionic surfactant: Toho Chemical Industry Co., Ltd., brand name), 5 parts of 1% aqueous solution of xanthan gum, 40 parts of water and 10 parts of ethylene glycol, those except the active ingredient were dissolved uniformly, and then the compound of the invention was added. After fully stirred, the mixture was wet milled with a sand mill to obtain a flowable.

Example of Formulation 7 Powder

Five parts of the compound of the invention (807) and 95 parts of clay were admixed to obtain powder.

Test Example 1: Test of Rice Blast Controlling Effect (Spray Application Test)

A diluted solution of a wettable powder prepared at 500 ppm in accordance with formulation Example 4 was applied to a rice pot (variety: Koshihikari; 2-leaf stage) and air-dried. The plant was put into an artificial weather room (set conditions: 22° C., 12-hour dark light cycle) and spray-inoculated with a suspension of *Pyricularia oryzae* spores. The artificial weather room was kept at high humidity, and the plant was examined after 7 days. The preventive value was calculated by the following equation and the controlling effect was evaluated based on the criteria shown in the following table. The results are shown in Table 3.

Preventive value (%)=(1−the number of lesions in treated plot/the number of lesions in untreated plot)×100

| Effect | Preventive value |
|---|---|
| A | 100% |
| B | 80% or more and less than 100% |
| C | 50% or more and less than 80% |
| D | less than 50% |

As a control, the following chemicals were used.

General formulation (7):

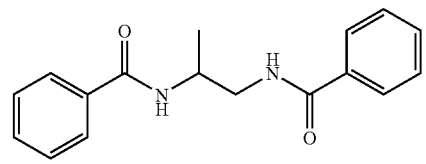

(7)

General formulation (8):

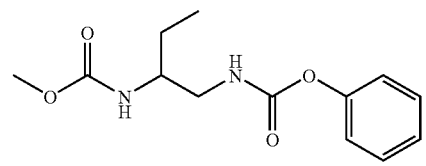

(8)

TABLE 3

Rice blast controlling effect test (Spray Application Test)

| Comp. No. | Grade of Effect |
|---|---|
| 4 | A |
| 26 | A |
| 30 | A |
| 66 | A |
| 215 | A |
| 216 | A |
| 236 | A |
| 237 | A |
| 238 | A |
| 239 | A |
| 240 | A |
| 241 | A |
| 242 | A |
| 243 | A |
| 245 | A |
| 246 | A |
| 247 | A |
| 279 | A |
| 284 | A |
| 289 | A |
| 290 | A |
| 384 | A |
| 387 | A |
| 464 | B |
| 469 | B |
| 470 | A |
| 471 | A |
| 504 | B |
| 526 | A |
| 530 | A |
| 596 | A |
| 600 | A |
| 636 | A |
| 674 | A |
| 677 | A |
| 739 | A |
| 742 | A |

TABLE 3-continued

Rice blast controlling effect test (Spray Application Test)

| Comp. No. | Grade of Effect |
|---|---|
| 804 | A |
| 807 | A |
| 1049 | A |
| 1050 | A |
| 1063 | A |
| 1066 | A |
| 1078 | A |
| 1081 | A |
| 1123 | A |
| 1126 | A |
| 1138 | A |
| 1141 | A |
| 1153 | A |
| 1156 | A |
| 1168 | A |
| 1171 | A |
| 1183 | A |
| 1186 | A |
| 1198 | A |
| 1201 | A |
| 1213 | A |
| 1216 | A |
| 1228 | A |
| 1231 | A |
| 1258 | A |
| 1261 | A |
| 1273 | A |
| 1276 | A |
| Formula (7) | D |
| Formula (8) | D |

Test Example 2: Test of Rice Blast Controlling Effect (Water Surface Application)

Rice seedlings (variety: Koshihikari; 3-leaf stage) were planted in 1/5000 are Wagner pots and grown for one week in a green house. Granules prepared in accordance with Formulation Example 2 were applied to water surface in each pot at a rate of 3 kg/10 ares. After 30 days from the application, a liquid suspension of *Pyricularia oryzae* spores was directly sprayed to the rice plants. The rice plants were placed under the conditions of 25° C. and high humidity for 1 week, and the number of lesions was checked. The preventive value was calculated by the following equation and the controlling effect was evaluated based on the following standard. The results are shown in Table 4. As a control, the same chemical as in Test Example 1 was used.

Preventive value (%)=(1−the number of lesions in treated plot/the number of lesions in untreated plot)×100

| Effect | Preventive value |
|---|---|
| A | From 80% to 100% |
| B | 50% or more and less than 80% |
| C | less than 50% |

TABLE 4

Rice blast controlling effect test (Water surface application)

| Comp. No. | Grade of Effect |
|---|---|
| 4 | A |
| 26 | A |
| 30 | A |
| 66 | A |
| 215 | A |
| 216 | A |
| 236 | A |
| 237 | A |
| 238 | A |
| 239 | A |
| 240 | A |
| 241 | A |
| 242 | A |
| 243 | A |
| 245 | A |
| 246 | A |
| 247 | A |
| 279 | A |
| 284 | A |
| 289 | A |
| 290 | A |
| 384 | A |
| 387 | A |
| 464 | B |
| 469 | B |
| 470 | A |
| 471 | A |
| 504 | B |
| 526 | A |
| 530 | A |
| 596 | A |
| 600 | A |
| 636 | A |
| 674 | A |
| 677 | A |
| 739 | A |
| 742 | A |
| 804 | A |
| 807 | A |
| 1049 | A |
| 1050 | A |
| 1063 | A |
| 1066 | A |
| 1078 | A |
| 1081 | A |
| 1123 | A |
| 1126 | A |
| 1138 | A |
| 1141 | A |
| 1153 | A |
| 1156 | A |
| 1168 | A |
| 1171 | A |
| 1183 | A |
| 1186 | A |
| 1198 | A |
| 1201 | A |
| 1213 | A |
| 1216 | A |
| 1228 | A |
| 1231 | A |
| 1258 | A |
| 1261 | A |
| 1273 | A |
| 1276 | A |
| Formula (7) | C |
| Formula (8) | C |

Test Example 3: Test of Rice Blast Controlling Effect (Nursery Box Treatment)

Rice seedlings (variety: Koshihikari; 2-leaf stage) raised in a nursery box for rice (30 cm×60 cm×3 cm) were treated with granules prepared in accordance with Formulation Example 1 in a quantity of 50 g per box. After 3 days, the rice seedlings were transplanted into a 1/5000 are Wagner in area and raised in a greenhouse. Thirty days after the transplantation, the plant was spray-inoculated with a suspension of *Pyricularia oryzae* spores, allowed to keep under the conditions of 25° C. and high humidity for 1 week, and the number of lesions was counted. The preventive value was calculated by the following equation and the controlling effect was evaluated based on the same criteria as in Test Example 2. The results are shown in Table 5. As a control, the same chemical as in Test Example 1 was used.

Preventive value (%)=(1−the number of lesions in treated plot/the number of lesions in untreated plot)×100

TABLE 5

Test of rice blast controlling effect (Nursery box treatment)

| Comp. No. | Grade of Effect |
|---|---|
| 4 | A |
| 26 | A |
| 30 | A |
| 66 | A |
| 215 | A |
| 216 | A |
| 236 | A |
| 237 | A |
| 238 | A |
| 239 | A |
| 240 | A |
| 241 | A |
| 242 | A |
| 243 | A |
| 245 | A |
| 246 | A |
| 247 | A |
| 279 | A |
| 284 | A |
| 289 | A |
| 290 | A |
| 384 | A |
| 387 | A |
| 464 | B |
| 469 | B |
| 470 | A |
| 471 | A |
| 504 | B |
| 526 | A |
| 530 | A |
| 596 | A |
| 600 | A |
| 636 | A |
| 674 | A |
| 677 | A |
| 739 | A |
| 742 | A |
| 804 | A |
| 807 | A |
| 1049 | A |
| 1050 | A |
| 1063 | A |
| 1066 | A |
| 1078 | A |
| 1081 | A |
| 1123 | A |
| 1126 | A |
| 1138 | A |
| 1141 | A |
| 1153 | A |
| 1156 | A |
| 1168 | A |
| 1171 | A |
| 1183 | A |
| 1186 | A |
| 1198 | A |
| 1201 | A |
| 1213 | A |
| 1216 | A |
| 1228 | A |
| 1231 | A |
| 1258 | A |
| 1261 | A |

TABLE 5-continued

Test of rice blast controlling effect (Nursery box treatment)

| Comp. No. | Grade of Effect |
|---|---|
| 1273 | A |
| 1276 | A |
| Formula (7) | C |
| Formula (8) | C |

INDUSTRIAL APPLICABILITY

The diamine derivative according to this invention exhibit an excellent rice blast controlling effect, but, on the other hand, does not injure useful crops; therefore, it is very useful as an agricultural and horticultural fungicide.

What is claimed is:

1. A diamine derivative, represented by the following general formula (1):

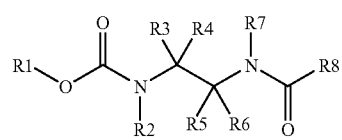

wherein

R1 represents an alkyl group with 1 to 6 carbon atoms provided that the alkyl group is not a tert-butyl, a cycloalkyl group with 3 to 6 carbon atoms, an alkenyl group with 2 to 6 carbon atoms, a cycloalkenyl group with 3 to 6 carbon atoms, an alkynyl group with 2 to 6 carbon atoms, an arylalkyl group which may be substituted, a heteroarylalkyl group which may be substituted, an aryl group which may be substituted, or a heteroaryl group which may be substituted;

R2 and R7 independently represent a hydrogen atom, an alkyl group with 1 to 6 carbon atoms, a cycloalkyl group with 3 to 6 carbon atoms, an alkenyl group with 2 to 6 carbon atoms, a cycloalkenyl group with 3 to 6 carbon atoms, an alkynyl group with 2 to 6 carbon atoms, an arylalkyl group which may be substituted, an aryl group which may be substituted, or an acyl group;

R3 and R4 independently represent a hydrogen atom, an alkyl group with 1 to 6 carbon atoms, a cycloalkyl group with 3 to 6 carbon atoms, an alkenyl group with 2 to 6 carbon atoms, a cycloalkenyl group with 3 to 6 carbon atoms, an alkynyl group with 2 to 6 carbon atoms, an arylalkyl group which may be substituted, a heteroarylalkyl group which may be substituted, an aryl group which may be substituted or a heteroaryl group which may be substituted, or a cycloalkyl group with 3 to 6 carbon atoms including an attached carbon atom;

R5 and R6 independently represent a hydrogen atom, an alkyl group with 1 to 6 carbon atoms, a cycloalkyl group with 3 to 6 carbon atoms, an alkenyl group with 2 to 6 carbon atoms, a cycloalkenyl group with 3 to 6 carbon atoms, an alkynyl group with 2 to 6 carbon atoms, an arylalkyl group which may be substituted, or an aryl group which may be substituted; provided that the case is excluded where R3, R4, R5 and R6 all represent a hydrogen atom or where any one of R3, R4, R5 and R6 represents a methyl group which may be substituted and the others represent a hydrogen atom, and R8 represents an aryl group which may be substituted or a heteroaryl group which may be substituted.

2. The diamine derivative according to claim 1, wherein

R1 represents an alkyl group with 1 to 6 carbon atoms provided that the alkyl group is not a tert-butyl, a cycloalkyl group with 3 to 6 carbon atoms, an alkenyl group with 2 to 6 carbon atoms, an arylalkyl group which may be substituted, a heteroarylalkyl group which may be substituted, an aryl group which may be substituted, or a heteroaryl group which may be substituted;

R2 and R7 independently represent a hydrogen atom, an alkyl group with 1 to 6 carbon atoms, a cycloalkyl group with 3 to 6 carbon atoms, an arylalkyl group which may be substituted, an aryl group which may be substituted, or an acyl group;

R3 and R4 independently represent a hydrogen atom, an alkyl group with 1 to 6 carbon atoms, a cycloalkyl group with 3 to 6 carbon atoms, an alkenyl group with 2 to 6 carbon atoms, an arylalkyl group which may be substituted, a heteroarylalkyl group which may be substituted, an aryl group which may be substituted or a heteroaryl group which may be substituted, or a cycloalkyl group with 3 to 6 carbon atoms including an attached carbon atom; and R5 and R6 independently represent a hydrogen atom, an alkyl group with 1 to 6 carbon atoms, a cycloalkyl group with 3 to 6 carbon atoms, an arylalkyl group which may be substituted, or an aryl group which may be substituted; provided that the case is excluded where R3, R4, R5 and R6 all represent a hydrogen atom or where any one of R3, R4, R5 and R6 represents a methyl group which may be substituted and the others represent a hydrogen atom.

3. The diamine derivative according to claim 2, wherein

R2 and R7 independently represent a hydrogen atom, an alkyl group with 1 to 6 carbon atoms, or an acyl group;

R3 and R4 independently represent a hydrogen atom, an alkyl group with 1 to 6 carbon atoms, a cycloalkyl group with 3 to 6 carbon atoms, an arylalkyl group which may be substituted, an aryl group which may be substituted, or a cycloalkyl group with 3 to 6 carbon atoms including an attached carbon atom; and R5 and R6 independently represent a hydrogen atom, an alkyl group with 1 to 6 carbon atoms, an arylalkyl group which may be substituted, or an aryl group which may be substituted; provided that the case is excluded where R3, R4, R5 and R6 all represent a hydrogen atom or where any one of R3, R4, R5 and R6 represents a methyl group which may be substituted and the others represent a hydrogen atom.

4. The diamine derivative according to claim 3, wherein R2 and R7 represent a hydrogen atom.

5. A diamine derivative, represented by the following general formula (9):

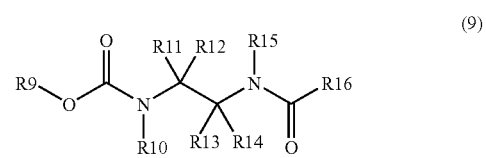

wherein R9 represents an alkyl group with 1 to 6 carbon atoms, a cycloalkyl group with 3 to 6 carbon atoms, an alkenyl group with 2 to 6 carbon atoms, a cycloalkenyl group with 3 to 6 carbon atoms, an alkynyl group with 2 to 6 carbon atoms, an arylalkyl group which may be substituted, a heteroarylalkyl group which may be substituted, a phenyl group, a phenyl group which is substituted at the fourth position, or a heteroaryl group which may be substituted;

R10 and R15 independently represent a hydrogen atom, an alkyl group with 1 to 6 carbon atoms, a cycloalkyl group with 3 to 6 carbon atoms, an alkenyl group with 2 to 6 carbon atoms, a cycloalkenyl group with 3 to 6 carbon atoms, an alkynyl group with 2 to 6 carbon atoms, an arylalkyl group which may be substituted, an aryl group which may be substituted, or an acyl group;

one of R11 and R12 represents a methyl group, and the other represents a hydrogen atom;

R13 and R14 represent a hydrogen atom, respectively; and

R16 represents a phenyl group, a phenyl group which is substituted at the fourth position, or a heteroaryl group which may be substituted.

6. The diamine derivative according to claim 5, wherein

R9 represents an alkyl group with 1 to 6 carbon atoms, a cycloalkyl group with 3 to 6 carbon atoms, an alkenyl group with 2 to 6 carbon atoms, an arylalkyl group which may be substituted, a heteroarylalkyl group which may be substituted, a phenyl group, a phenyl group which is substituted at the fourth position, or a heteroaryl group which may be substituted; and R10 and R15 represent a hydrogen atom, an alkyl group with ito 6 carbon atoms, a cycloalkyl group with 3 to 6 carbon atoms, an arylalkyl group which may be substituted, an aryl group which may be substituted, or an acyl group, independently.

7. The diamine derivative according to claim 6, wherein R10 and R15 independently represent a hydrogen atom, an alkyl group with 1 to 6 carbon atoms, or an acyl group.

8. The diamine derivative according to claim 7, wherein at R10 and R15 represent a hydrogen atom, respectively.

9. A fungicide, wherein it contains the diamine derivative according to claim 8 as an active ingredient.

10. A process for producing the diamine derivative according to claim 1, wherein a compound having the following general formula (2):

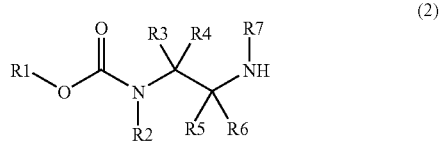

wherein

R1, R2, R3, R4, R5, R6 and R7 represent the same groups as those of the compounds according to claim 1, is reacted with a compound having the following general formula (3):

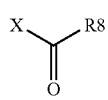
(3)

wherein

R8 represents the same group as that of the compound according to claim 1, and X represents a leaving group.

11. A process for producing the diamine derivative according to claim 1, wherein a compound of the general formula (2) is condensed with a compound having the following general formula (4):

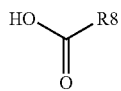
(4)

wherein

R8 represents the same group as that of the compounds according to claim 1.

12. A process for producing the diamine derivative according to claim 1, wherein a compound having the following general formula (5):

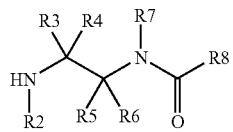
(5)

wherein

R2, R3, R4, R5, R6, R7 and R8 represent the same groups as those of the compound according to claim 1, is reacted with a compound having the following general formula (6):

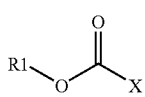
(6)

wherein

R1 represents the same group as that of the compound according to claim 1, and X represents a leaving group.

13. A process for producing the diamine derivative according to claim 5, wherein a compound having the following general formula (10):

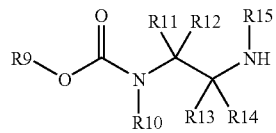
(10)

wherein

R9, R10, R11, R12, R13, R14 and R15 represent the same groups as those of the compounds according to claim 5, is reacted with a compound having the following general formula (11):

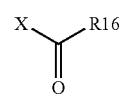
(11)

wherein

R16 represents the same group as that of the compound according to claim 5, and X represents a leaving group.

14. A process for producing the diamine derivative according to claim 5, wherein a compound of the general formula (10) is condensed with a compound having the following general formula (12):

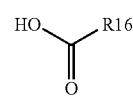
(12)

wherein

R16 represents the same group as that of the compounds according to claim 5.

15. A process for producing the diamine derivative according to claim 5, wherein a compound having the following general formula (13):

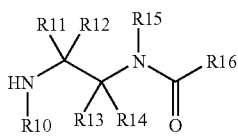
(13)

wherein

R10, R11, R12, R13, R14, R15 and R16 represent the same groups as those of the compound according to claim 5, is reacted with a compound having the following general formula (14):

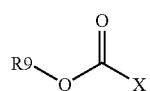
(14)

wherein

R9 represents the same group as that of the compound according to claim 5, and X represents a leaving group.

16. A fungicide, wherein it contains the diamine derivative according to claim 1 as an active ingredient.

17. A fungicide, wherein it contains the diamine derivative according to claim 5 as an active ingredient.

* * * * *